United States Patent [19]

Demerson et al.

[11] 4,066,780

[45] Jan. 3, 1978

[54] PYRANOINDOLE DERIVATIVES AS ANTIULCER AGENTS

[75] Inventors: Christopher A. Demerson, Montreal; Leslie G. Humber, Dollard des Ormeaux; Andre A. Asselin, Lemoyne; Ivo Jirkovsky, Montreal; Thomas A. Dobson, Roxboro, all of Canada

[73] Assignee: Ayerst McKenna and Harrison Ltd., Montreal, Canada

[21] Appl. No.: 736,606

[22] Filed: Oct. 28, 1976

Related U.S. Application Data

[60] Division of Ser. No. 555,906, March 5, 1975, Pat. No. 4,003,913, and a continuation-in-part of Ser. No. 377,837, July 9, 1973, Pat. No. 3,880,853, which is a continuation-in-part of Ser. No. 217,627, Jan. 13, 1972, Pat. No. 3,852,285.

[51] Int. Cl.$^2$ .................. A61K 31/40; A61K 31/535; A61K 31/495; A61K 31/445

[52] U.S. Cl. ............................... 424/274; 424/248.51; 424/248.54; 424/248.55; 424/250; 424/267

[58] Field of Search ................... 424/274, 248.54, 267, 424/250, 248.51, 248.55

[56] References Cited

PUBLICATIONS

Chem. Ber., 83 271 (1950).

*Primary Examiner*—Frederick E. Waddell
*Attorney, Agent, or Firm*—Adley F. Mandel

[57] ABSTRACT

Pyranoindole and thiopyranoindole derivatives characterized by having an amino(lower)alkyl radical attached to either or both the 1 and 9 position of a pyrano[3,4-b]indole or thiopyrano[3,4-b]indole nucleus or having said radical attached to the 1 position of a pyrano[4,3-b]indole or thiopyrano[4,3-b]indole nucleus are disclosed. The amino portion of the amino(lower)alkyl radical may be further substituted with one or two lower alkyl groups or incorporated into a heterocyclic amine radical. The derivatives having the amino(lower)alkyl radical only at position 1 are further substituted at position 1 and may be optionally substituted at positions 3,4,5,6,7,8, and 9. The pyrano[3,4-b]indole or thiopyrano[3,4-b]indole derivatives having the amino(lower)alkyl radical only at position 9 possess two substituents at position 1 and may be optionally substituted at position 3,4,5,6,7, and 8; the derivatives having an amino(lower)alkyl radical at both positions 1 and 9 are further substituted at position 1 and may be optionally substituted at positions 3,4,5,6,7 and 8. The pyrano-and thiopyranoindole derivatives of this invention are useful antidepressant and antiulcer agents. Methods for the preparation and use of these derivatives are also disclosed.

4 Claims, No Drawings

PYRANOINDOLE DERIVATIVES AS ANTIULCER AGENTS

This is a division, of application Ser. No. 555,906, filed Mar. 5, 1975 now U.S. Pat. No. 4,003,913 which is a continuation-in-part of each of our earlier filed applications, patent application Ser. No. 377,837, filed July 9, 1973 now U.S. Pat. No. 3,880,853 and patent application Ser. No. 217,627, filed Jan. 13, 1972 (now U.S. Pat. No. 3,852,285, issued Dec. 3, 1974).

BACKGROUND OF THE INVENTION

1. Field of Invention

This invention relates to novel pyranoindole and thiopyranoindole derivatives, to processes for their preparation and to intermediates used in these processes.

More specifically, the present invention relates to novel pyranoindole and thiopyranoindole derivatives possessing valuable pharmacologic properties. For example, these derivatives exhibit useful antidepressant properties at dosages which do not elicit undesirable side effects. Furthermore the present derivatives exhibit properties useful for the treatment and prevention of ulcers. The combination of these pharmacologic properties together with a low order of toxicity render the pyranoindoles and thiopyranoindoles of the invention therapeutically useful.

2. Description of the Prior Art

Only a rather limited number of reports dealing with pyranoindole derivatives are available. In the few that do exist, pyranoindoles are treated more in the manner of chemical curiosities. For the most part these reports discuss the preparation of pyranoindoles in which the pyran portion thereof exists as a lactone. For example, see H. Plieninger, Chem. Ber., 83, 271 (1950), S. Sakurai and T. Ito, Nippon Kagaku Zasshi, 78, 1665 (1957); [Chem Abstr., 54, 1488f (1960)], and J. Szmuszkovicz, J. Org. Chem., 27, 511 (1962).

The thiopyranoindoles of the prior art, for example, 5-(3-aminopropyl)-1,3,4,5-tetrahydrothiopyrano[4,3-b]indole, M.E. Freed, et al., J. Med. Chem., 7, 628 (1964) are distinguished from the present compounds of this invention by lacking substitutents on the thiopyran ring.

SUMMARY OF THE INVENTION

The pyranoindole and thiopyranoindole derivatives of this invention are characterized by having an amino(-lower)alkyl radical attached to a pyranoindole or thiopyranoindole nucleus. The preferred derivatives of this invention are represented by formula I and Ia

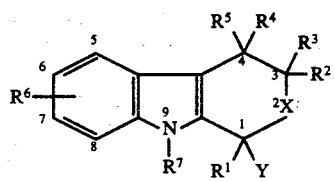

-continued

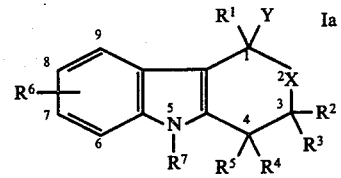

in which $R^1$ is lower alkyl or lower cycloalkyl; $R^2$, $R^3$, $R^4$ and $R^5$ are the same or different selected from the group consisting of hydrogen and lower alkyl; $R^6$ is hydrogen, lower alkyl hydroxy, lower alkoxy, lower alkanoyloxy, nitro or halo; $R^7$ is hydrogen, lower alkyl, lower alkenyl, propargyl, phenyl(lower)alkyl or an amino(lower)alkyl radical of formula —Alk—$NR^8R^9$ wherein Alk is an alkylene selected form the group consisting of $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are either the same or different selected from the group consisting of hydrogen and lower alkyl, or $R^8$ is lower alkyl and $R^9$ is p-chlorophenacyl or $R^8$ and $R^9$ together with the nitrogen atom to which they are joined form a heterocyclic amine radical selected from the group consisting of 1-pyrrolidinyl, piperidino, morpholino, piperazino, 4-(lower-alkyl)-1-piperazinyl and 4-[hydroxy(lower)alkyl-1-piperazinyl; X is oxy or thio; and Y is lower alkyl, phenyl(lower)alkyl or an amino(lower)alkyl radical of formula —Alk-$NR^8R^9$ wherein Alk is an alkylene selected from the group consisting of $CR^{10}R^{11}$, $CR^{10}R^{11}CR^{12}R^{13}$, $CR^{10}R^{11}CR^{12}R^{13}CR^{14}R^{15}$ and $CR^{10}R^{11}CR^{12}R^{13}CR^{14}R^{15}CR^{16}R^{17}$ wherein $R^{10}$, $R^{11}$, $R^{12}$, $R^{13}$, $R^{14}$, $R^{15}$, $R^{16}$ and $R^{17}$ are hydrogen or lower alkyl and $R^8$ and $R^9$ are as defined herein; with the provisos that at least one of $R^7$ and Y is -Alk-$NR^8R^9$ and that in the compounds of formula Ia, Y must be —Alk-$NR^8R^9$ as defined herein.

In the above definitions it is understood that Alk, $R^8$ and $R^9$ in each case are entitled to the full range of their definitions as listed above, so that Alk, $R^8$ and $R^9$ of Alk-$NR^8R^9$ linked to position 9 of formula I need not necessarily be the same as Alk, $R^8$ and $R^9$ of Alk-$NR^8R^9$ linked to position 1.

Various processes for the preparation of the compounds of formula I are disclosed.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, 2-methylpentyl and the like.

The term "lower alkyl" as used herein contemplates both straight and branched chain alkenyl radicals containing from two to six carbon atoms and includes vinyl, allyl, 1-propenyl, methallyl, 2-ethyl-2-butenyl and from one to six carbon atoms and includes methyl, ethyl, propyl, isopropyl, butyl, isobutyl, 2-methylpentyl and the like.

The term "lower alkenyl" as used herein contemplates both straight and branched chain alkenyl radicals containing from two to six carbon atoms and includes vinyl, allyl, 1-propenyl, methallyl, 2-ethyl-3-butenyl and the like.

The term "phenyl(lower)alkyl" as used herein contemplates a phenylalkyl radical in which the alkyl portion thereof contains from one to four carbon atoms and includes benzyl, phenethyl, α-methylphenethyl and the like.

The term "lower cycloalkyl" as used herein contemplates saturated cyclic hydrocarbon radicals containing from three to six carbon atoms and includes cyclopropyl, cyclobutyl, cyclopentyl and the like.

The term "lower alkoxy" as used herein contemplates both straight and branched chain alkoxy radicals containing from one to four carbon atoms and includes methoxy, ethoxy, isopropoxy and the like.

The term "lower alkanoyloxy" as used herein contemplates both straight and branched chain alkanoyloxy radicals containing from two to six carbon atoms and includes acetoxy, propionyloxy, hexanoyloxy and the like.

The term "halo" as used herein contamplates halogens and includes fluorine, chlorine, bromine and iodine.

The compounds of this invention are capable of forming acid addition salts with pharmaceutically acceptable acids. Such acid addition salts are included within the scope of this invention.

The acid addition salts are prepared by reacting the base form of the appropriate compound of formula I or Ia with either one to four equivalents, depending on the number of basic nitrogens in the compound, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formulae I and Ia which result from asymmetric centers, contained therein. These isomeric forms are prepared by different methods and are purified readily by crystallization or chromatography.

Individual optical isomers, which might be separated by fractional crystallization of the diastereoisomeric salts formed thereof, for instance, with d- or l- tartaric acid or D-(+)-α-bromocamphor sulfonic acid, are also included.

ANTIDEPRESSANT ACTIVITY

The useful antidepressant activity of the compounds of formulae I and Ia and their acid addition salts with pharmaceuticaly acceptable acids are demonstrated in standard pharmacologic tests, such as, for example, the tests described by F. Hafliger and V. Burckhart in "Psychopharmacological Agents", M. Gordon, Ed., Academic Press, New York and London, 1964, pp. 75 – 83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg. Several of the preferred compounds, for instance, 1-[(2-dimethylamino)ethyl]-1-methyl-1,3,4,9-tetrahydropyrano-[3,4-b]indole oxalate (Example 309), 1-methyl-[3-(methylamino)propyl]-1,3,4,9-tetrahydropyrano-[3,4-b]indole oxalate (Example310), 1-[3-(dimethylamino)propyl]-1-methyl-1,3,4,9-tetrahydropyrano-[3,4-b]indole oxalate (Example 312), 1-[2-(dimethylamino)ethyl]-1-propyl-1,3,4,9-tetrahydropyrano-[3,4-b]indole maleate (Example 330), 1-[2-(dimethylaminoethyl]-1-methyl-9-propyl-1,3,4,9-tetrahydropyrano-[3,4-b]indole maleate (Example 683), and 1-[2-dimethylamino)ethyl]-9-ethyl-1-methyl-1,3,4,9-tetrahydrothiopyrano[3,4-b]indole hydrochloride (Example 911), antagonize the effects of reserpine in mice at dose ranges from about 1 to 15 mg/kg.

When the compounds of this invention are used as antidepressants in warm-blooded mammals, e.g. rats and mice, they may be used aone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are given at a concentration level that will afford an effective dose without causing ay harmful or deleterious side effects and preferably at a level that is in a range of from about 0.1 mg to about 50 mg per kilo per day, although as aforementioned variations will occur. However, a dosage level that is in the range of from about 0.5 mg to about 25 mg per kilo per day is most desirably employed in order to achieve effective results.

ANTIULCER ACTIVITY

The compounds of this invention possess another useful pharmacologic property; that is, they are useful antiulcer agents. More particularly, the said compounds of this invention exhibit antiulcer activity in standard pharmacologic tests, for example, the test described by D. A. Brodie and L. S. Valitski, Proc. Soc. Exptl. Biol. Med., 113, 998 (1963), based on the prevention of stress-induced ulcers.

When these compounds are employed as antiulcer agents, they are formulated and administered in the same manner as described above for their use as antidepressant agents.

PROCESSES

For the preparation of the pyranoindole and thiopyranoindole derivatives of formula I we prefer to use as starting materials the compounds of general formula II,

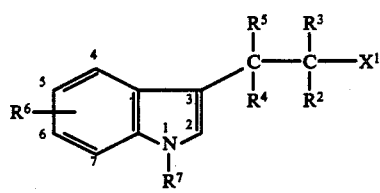

in which $R^2$, $R^3$, $R^4$, $R^5$, $R^6$ and $R^7$ are as defined in the first instance and $X^1$ is hydroxy, mercapto, —S—SO$_3$.—Na or —S—SO$_3$K.

The starting materials of formula II in which $X^1$ is hydroxy are either known, for example, tryptophol, described by H. R. Snyder and F. J. Pilgrim, J. Am. Chem. Soc. 70, 3770 (1948), or they are obtained by the following process:

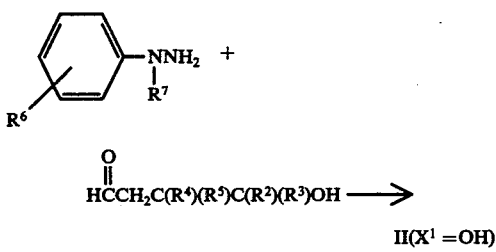

$$II(X^1 = OH)$$

With reference to this process phenylhydrazines of formula III and the hydroxyaldehyde of formula IV are reacted together according to the conditions of the "Fischer Indole Synthesis", for example, see P. L. Julian, E. N. Myer and H. C. Printy, "Heterocyclic Compounds", R. C. Elderfield, Ed., Vol. 3, John Wiley and Sons, Inc., New York, 1952, pp. 8 - 11, to form the desired starting material (II, $X^1$ = OH).

The phenylhydrazines of formula III are either known or are prepared according to known methods. A convenient method involves the diazotization of the appropriately substituted aniline to give the corresponding diazo derivative. The latter compound is then reduced with stannous chloride or sodium sulfite to give the corresponding phenylhydrazine, see L. F. Fieser and M. Fieser, "Advanced Organic Chemistry", Reinhold Publishing Corporation, New York, 1961, p. 734.

The hydroxyaldehydes of formula IV are either known, see for example, "Rodd's Chemistry of Carbon Compounds", S. Coffey, Ed., Vol. I d, 2nd ed., Elsevier Publishing Co., Amsterdam, 1965, pp. 44 - 49, or they are prepared according to known methods. A convenient method involves reduction of an appropriate lactone of formula

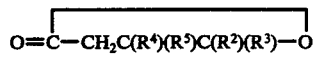

with bis-(3-methyl-2-butyl)borane, H. G. Brown and D. B. Bigley, J. Am. Chem. Soc., 83, 486 (1961), diisobutyl aluminum hydride, L. I. Zakharkkin and I. M. Khorlina, Tetrahedron Letters, 619 (1962) or sodium aluminum hydride, L. I. Zakharkin et al., Tetrahedron Letters, 2087 (1963). The appropriate lactones utilized in this condensation are either commercially available, for example, δ-valerolactone, α-methyl-butyrolactone, or they are described with a variety of methods for their preparation in organic chemistry textbooks; such as the textbooks, "Methoden der Organischen Chemie", Houben-Weyl, E. Muller, Ed., Vol. VI/2, Georg Thieme Verlag, Stuttgart, 1963, pp. 561 - 852 or L. F. Fieser and M. Fieser, "Advanced Organic Chemistry", cited above.

Alternatively, the starting materials of formula II in which $R^2$, $R^3$, $R^4$ and $R^7$ are hydrogen and $X^1$ is hydroxy are prepared by lithium aluminum hydride reduction (N. G. Gaylord, "Reduction with Complex Metal Hydrides", Interscience Publishers, Inc., New York, 1956, pp. 322 - 370) of compounds of formula V described by T. Y. Shen, U.S. Pat. No. 3,161,654, Dec. 15, 1964:

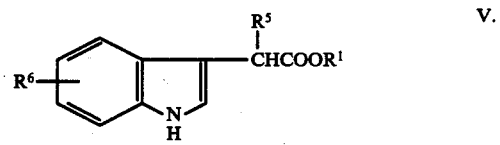

wherein $R^{18}$ is lower alkyl and $R^5$ and $R^6$ are as defined in the first instance.

In addition, convenient processes are available for the specific synthesis of certain starting materials of formula II. For example, starting materials of formula II in which $R^2$, $R^3$, $R^4$, $R^5$ and $R^7$ are hydrogen and $X^1$ is hydroxy are obtained by reduction of the appropriate ethyl 3-indoleglyoxylate with lithium aluminum hydride. British Patent 778,823 and T. Nogrady and T. W. Doyle, Can. J. Chem., 42, 485 (1964). Starting materials of formula II in which $R^2$ and $R^4$ are hydrogen, $R^3$, $R^5$ and $R^7$ are hydrogen or lower alkyl and $X^1$ is hydroxy are obtained by reacting indole or an appropriately substituted indole with ethylene oxide or lower alkyl substituted ethylene oxide according to the process of M. Julia et al., Bull. Soc. Chim. Fr., 2291 (1966).

The starging materials of formula II in which $X^1$ is mercapto, —S—SO$_3$Na or —S—SO$_3$K, and $R^2$, $R^3$, $R^4$, $R^5$, $R^6$ and $R^7$ are as defined in the first instance are obtained by the following process: The appropriate compound of formula 11 ($X^1$=OH) described above, is treated with phosphorus tribromide in an inert solvent, for example, ether or methylene chloride to afford the corresponding 3-(2-bromoethyl)-indole derivative. The latter compound is then converted to the desired starting material of formula II ($X^1$ = SH) by a procedure similar to that described by N. N. Suvorov and V. N. Buyanov, Khim.-Farm. Zh., 1, (1967), [Chem. Abstr. 67, 73474a (1967)], for converting 3-(2-bromethyl)-indole to indole-3-ethanethiol (II; $R^2$, $R^3$,$R^4$, $R^5$ and $R^6$ = H and $X^1$ = SH). Accordingly, the appropriate 3-(2-bromoethyl)-indole derivative is treated with sodium or potassium thiosulfate to afford the corresponding sodium or potassium β-(3-indolyl)ethyl thiosulfate derivative, respectively; namely the desired starting materials of formula II (X=—S—SO$_3$Na or —S—SO$_3$K). Treatment of the latter product with strong alkali, for example, sodium or potassium hydroxide, yields the corresponding bis[ω-(3-indolyl)ethyl]-disulfide derivative. Reduction of the latter compound with lithium aluminum hydride gives the desired compounds of formula II ($X^1$ = SH).

Alternatively, the preceding thiosulfate derivative is treated with acid, for example, dilute aqueous solutions of hydrochloric acid, sulfuric acid or phosphoric acid, to give directly the latter compound of formula II.

It should be noted that the preceding processes may not be entirely practical for the preparation of the compounds of formula II in which $X^1$ is mercapto, $-S-SO_3Na$ or $-S-SO_3K$, and $R^6$ is hydroxy or lower alkanoyloxy. For this reason, the preferred starting materials of formula II for the ultimate preparation of the compounds of formula I in which $R^6$ is hydroxy or lower alkanoyloxy and X is thio are the corresponding compounds of formula II in which $R^6$ is benzyloxy, i.e., a hydroxyl with a protecting benzyl group or other suitable protecting group, see J. F. McOmie, "Advances in Organic Chemistry", Vol. 3, R. A. Raphael, et al, Ed., Interscience Publishers, New York, 1963, pp. 191 – 294. When the latter compounds are used as starting materials in this manner, they are first subjected to the process (II + VI→VII), described below. Subsequently, the benzyloxy group is removed by hydrogenation, in the presence of a catalyst, for example, 10% palladium on carbon, just prior to affording the desired corresponding compound of formula I in which $R^6$ is hydroxy. The latter are converted, if desired, to the corresponding compound of formula I in which $R^6$ is lower alkanoyloxy by conventional means, for example, by treatment with the appropriate lower alkanoic anhydride preferably in the presence of pyridine. Likewise, it should be noted that similar use of the starting materials of formula II in which $X^1$ is hydroxy and $R^6$ is benzyloxy to obtain the corresponding compound of formula I in which $R^6$ is hydroxy or lower alkanoyloxy is also preferred.

The above described starting materials of formula II in which $R^2$, $R^3$, $R^4$, $R^5$, $R^6$, $R^7$ and $X^1$ are as defined in the first instance are now subjected to a key reaction comprising the treatment of said starting materials with a compound of formula

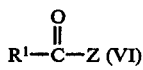

in which $R^1$ is as defined in the first instance and Z is selected from the group consisting of:

a. $COOR^{19}$ and $Alk^1 — COOR^{19}$ in which $R^{19}$ is hydrogen or lower alkyl and $Alk^1$ is an alkylene selected from the group consisting of $CR^{10}R^{11}$, $CR^{10}R^{11}CR^{12}R^{13}$ and $CR^{10}R^{11}CR^{12}R^{13}CR^{14}R^{15}$ wherein $R^{10}$, $R^{11}$, $R^{12}$, $R^{13}$, $R^{14}$ and $R^{15}$ are hydrogen or lower alkyl, b. $CONR^8R^9$ and $Alk^1—CONR^8R^9$ in which $Alk^1$, $R^8$ and $R^9$ are as defined above, c. $CH_2OCOR^{20}$ and $Alk^1—CH_2OCOR^{20}$ in which $R^{20}$ is hydrogen or lower alkyl and $Alk^1$ as as defined above, d. $Alk^2—L$ in which $Alk^2$ is an alkylene selected from the group consisting of $CR^{10}R^{11}CHR^{12}$, $CR^{10}R^{11}CR^{12}R^{13}CHR^{14}$ and $CR^{10}R^{11}CR^{12}R^{13}CR^{14}R^{15}CHR^{16}$ wherein $R^{10}$, $R^{11}$, $R^{12}$, $R^{13}$, $R^{14}$, $R^{15}$ and $R^{16}$ are as defined above and L is halo, e. $Alk NR^8COR^{21}$ in which Alk and $R^8$ are as defined in the first instance and $R^{21}$ is hydrogen or lower alkyl containing from one to five carbon atoms, f. $Alk - NO_2$ in which Alk is as defined in the first instance, g. Lower alkyl and phenyl(lower)alkyl., and h. $Alk — NR^8R^9$ in which Alk, $R^8$ and $R^9$ are as defined in the first instance, in the presence of an acid catalyst to yield the compounds of formula VII in which $R^1$, $R^2$, $R^3$, $R^4$, $R^5$, $R^6$, $R^7$, X and Z are as defined above.

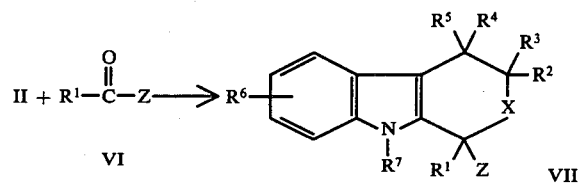

Thereafter the appropriate compound of formula VII is converted to the desired pyranoindole of formula I according to the process described hereinafter or is actually the desired compound of formula I in the case where Z is $Alk-NR^8R^9$, as described above.

In practising the condensation (II + VI → VII) a solvent is used generally as a reaction medium. Any solvent inert to the reaction conditions may be used. Suitable solvents include aromatic hydrocarbon, for example benzene, or toluene, ethers and cyclic ethers, for example diethyl ether, dioxan, or tetrahydrofuran, halogenated hydrocarbons, for example methylene dichloride, or carbon tetrachloride and the like. Benzene and tetrahydrofuran are especially convenient and practical for this use. A variety of suitable acid catalysts may be used for this condensation, for example, the type of catalyst used in a Friedel-Crafts reaction, i.e. p-toluenesulfonic acid, aluminum chloride, phosphorus pentoxide, boron trifluoride, zinc chloride, hydrochloric acid, perchloric acid, trifluoroacetic acid, sulfuric acid and the like. p-Toluenesulfonic acid, aluminum chloride, boron trifluoride and phosphorus pentoxide are included among the preferred acid catalysts. The amount of acid catalyst used is not espcially critical and may range from 0.01 molar equivalents to 100 molar equivalents; however, a range of from 0.1 to 10 molar equivalents is generally preferred; however, note that the amount of acid catalyst should be in excess with respect to the basic nitrogens that may be present in $R^7$ of the starting material of compound II or the compound of formula

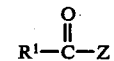

when Z is $Alk-NR^8R^9$. The time of the reaction may range from 10 minutes to 60 hours, with the preferred range being from one-half to 24 hours. The temperature of the reaction may range from 20° C. to the boiling point of the reaction mixture. Preferred temperature ranges include 20° to 120° C.

A more detailed description of the preparation of the above intermediate compounds of formula VII and a description of their subsequent conversion to pyranoindole and thiopyranoindole derivatives of formula I are disclosed below. For convenience these descriptions are categorized into sections according to the group selected for Z for the intermediate.

a. Preparation and Conversion of Intermediates of Formula VII (Z = $COOR^{19}$ and $Alk^1—COOR^{19}$)

Intermediates of formula VII (Z = $COOR^{19}$ and $Alk^1—COOR^{19}$ in which $R^{19}$ is hydrogen or lower alkyl and $Alk^1$ is as defined in the first instance, $R^7$ is hydrogen and $R^1$, $R^2$, $R^3$, $R^4$, $R^5$, $R^6$ and X are as defined in the first instance) are readily obtained by the condensation (II←VI→VII) by using ketoacids or ketoesters of formula

in which $R^1$ is as defined in the first instance and Z is $COOR^{19}$ or $Alk^1$ — $COOR^{19}$ as defined above together with the starting material of formula II ($R^7 = H$).

Generally comparable yields of product are obtained in this process when either the ketoacid or the corresponding ketoester is used. However, in the case where it is desired to prepare an acid compond of formula VII($R^7 = H$) in which Z is $Alk^1COOR^{19}$ wherein $Alk^1$ is $CR^{10}R^{11}$ and $R^{19}$ is hydrogen (i.e., an acid intermediate of formula VII), it is preferable to first condense the appropriate β-ketoester of formula VI rather than the corresponding β-ketoacid and then hydrolyze the resulting ester product to give the desired acid compound.

Moreover, in the general practise of this invention it is often more convenient to prepare the acid compounds of formula VII($R^7 = H$) by using the ketoester instead of the ketoacid in this process and then hydrolyze the resulting ester product to the desired acid, the reason being simply that the ketoesters are generally more readily available either commercially or by synthesis.

The hydrolysis of compounds of formula VII($R^7 = H$) in which Z is $COOR^{19}$ or $Alk^1$ $COOR^{19}$ wherein $Alk^1$ is as defined in the first instance and $R^{19}$ is lower alkyl, i.e. ester intermediates of formula VII($R^7 = H$), to their corresponding acids of formula VII ($R^7 = H$) is readily effected by treatment with a suitable alkali, for example, potassium hydroxide or sodium carbonate, in aqueous methanol or aqueous ethanol or by treatment with lithium iodide in a suitable organic solvent, for example, collidine, see L. F. Fieser and M. Fieser, "Reagents for Organic Synthesis", John Wiley and Sons, Inc., New York, 1967, pp. 615 - 617.

The α-, β-, γ- and δ- ketoacids and -ketoesters of formula VI are either known, for example, ethyl pyruvate, levulinic acid, ethyl α,α-dimethylacetoacetate, and β,β-dimethyllevulic acid, or they are prepared by known methods described in general organic chemistry textbooks. For example, a comprehensive review on the properties and preparation of such α-, β-, γ- and δ-ketoacids and -ketoesters may be found in "Rodd's Chemistry of the Carbon Compounds", cited above, Vol. Id, pp. 226 - 274.

Thereafter these itermediate acids and esters of formula VII ($R^7 = H$) are converted to compounds of formula I in which $R^1$, $R^2$, $R^3$, $R^4$, $R^5$, $R^6$, $R^7$ and X are as defined in the first instance and Y is —Alk—$NR^8R^9$ in which Alk is $CH_2$ or $Alk^1$—$CH_2$ wherein $Alk^1$ is as defined in the first instance and $R^8$ and $R^9$ are as defined in the first instance. This conversion is accomplished by amidation, reduction and if desired N-alkylation of the indolic nitrogen. The order of these steps is not critical. However, we have found the following sequence of these steps to be both convenient and practical.

First, when it is desired to prepare the derivatives of the latter group of compounds of formula I in which $R^7$ is H, i.e., N-alkylation of the indolic nitrogen is not desired, either the above acid intermediate or ester intermediate may be employed.

In the case where the acid intermediate of formula VII($R^7 = H$) is employed, said acid is subjected to amidation by treatment with a lower alkyl chloroformate, preferably ethyl chloroformate, in the presence of triethylamine, affording the corresponding mixed anhydride, which is converted by treatment with the appropriate amine of formula $HNR^8R^9$ in which $R^8$ and $R^9$ are as defined in the first instance, for example, ammonia, methylamine or dimethylamine, to yield the corresponding amide of formula VII in which Z is $CONR^8R^9$ or $Alk^1CONR^8R^9$ in which $Alk^1$, $R^8$ and $R^9$ are as described in the first instance.

Alternatively, the latter amides are also obtained by treating the ester intermediates of formula VII ($R^7 = H$) with the appropriate amine according to known amidation methods, for example, see A. L. F. Beckwith in "The Chemistry of Amides", J. Zalicky, Ed., Interscience Publishers, New York, 1970, pp. 96 - 105.

Secondly, the amides so obtained are reduced with a suitable complex metal hydride to yield the desired pyranoindoles and thiopyranoindoles. Examples of suitable complex metal hydrides are lithium aluminum hydride, lithium aluminum hydride-aluminum chloride, aluminum hydride-aluminum chloride, diborane an sodium borohydride-aluminum chloride. Lithium aluminum hydride is preferred.

On the other hand when it is desired to prepare the compounds of formula I of the above group in which $R^1$, $R^2$, $R^3$, $R^4$, $R^5$, $R^6$ and X are as defined in the first instance, $R^7$ is lower alkyl, or lower alkenyl, propargyl, phenyl(lower)alkyl or amino(lower)alkyl and Y is —Alk—N $R^8R^9$ in which Alk is $CH_2$ or $Alk^1CH_2$ wherein $Alk^1$ is as defined in the first instance and $R^8$ and $R^9$ are as defined in the first instance, the acid or ester intermediate of formula VII ($R^7 = H$) are first subjected to N-alkylation by treatment with a molar excess of the appropriate organic halide, namely a lower alkyl halide, lower alkenyl halide, propargyl halide, phenyl(lower)alkyl halide or amino(lowe)alkyl halide, respectively, in an inert solvent in the presence of a proton acceptor. Suitable inert solvents include tetrahydrofuran, benzene, toluene and dimethylformamide. Suitable proton acceptors include sodium hydride, alkali metal carbonate and triethylamine. Preferred conditions for effecting this N-alkylation include the use of sodium hydride as a proton acceptor and tetrahydrofuran as an inert solvent. Although the optimum temperature and reaction time will vary depending on the reactants employed, the reaction is generally performed at the boiling point of the reaction mixture for a period of 30 minutes to 48 hours.

The lower alkyl halides, lower alkenyl halides, propargyl halide, phenyl(lower)alkyl halides and aminoalkyl(lower)halides employed herein are either known, for example, ethyl bromide, allyl bromide and dimethylaminoethyl chloride, or they are prepared by known methods, usually by the treatment of the corresponding alcohols with a halogenating agent, for instance, thionyl chloride, see D. J. Collins and J. J. Hobbs, Aust. J. Chem., 20, 1413 (1967) and R. B. Moffett, J. Org. Chem., 14, 862 (1949).

In this manner, the corresponding N-alkylated derivatives of the above acid and ester derivatives of formula VII are obtained. Thereafter these derivatives are subjected to the amidation and reduction steps according to the conditions described hereinabove in this section, to afford the desired compounds of formula I in which $R^7$ is lower alkyl, lower alkenyl, propargyl, phenyl(lower)alkyl, or amino(lower)alkyl.

Although the above sequence of steps for the conversion of the acid and ester intermediates of formula VII ($R^7 =$ H) to the above desired pyranoindoles is convenient and efficacious, a change in the order of the steps whereby the amides of formula VII ($R^7 =$ H) are treated with the appropriate organic halide according to the N-alkylation conditions described above, followed by reduction with a complex metal hydride, as described above, also affords the above desired compounds of formula I, in which $R^7$ is lower alkyl, lower alkenyl, propargyl, phenyl(lower)alkyl or amino(lower)alkyl. Treatment as decribed above, of the resulting corresponding amide derivative in which the indolic nitrogen is alkylated, also affords the above desired compounds of formula I, in which $R^7$ is lower alkyl, lower alkenyl, propargyl, phenyl(lower)alkyl or amino(lower)alkyl.

Furthermore, another change in the order of the steps for preparing the latter compounds of formula I is realized by N-alkylation, as described above, of the corresponding compounds of formula I in which $R^7$ is hydrogen, described above. In this case when the starting material employed is a pyranoindole or thiopyranoindole of formula I in which Y is —Alk—$NR^8R^9$ in which Alk is $CH_2$ or $Alk^1CH_2$ wherein $Alk^1$ is as defined in the first instance and $R^8$ is hydrogen and $R^9$ is hydrogen or lower alkyl, i.e., a primary or secondary amine function is present in the molecule in addition to the indolic nitrogen, it is expedient to use only one molar equivalent of the appropriate organic halide to avoid alkylation of the primary or secondary amine if so desired.

Another aspect of the present intermediates of formula VII relates to their conversion to compounds of formula I in which $R^1$, $R^2$, $R^3$, $R^4$, $R^5$, $R^6$, $R^7$ and X are as described in the first instance and Y is —Alk—$NR^8R^9$ in which Alk is $CH_2$ or $Alk^1CH_2$ wherein $Alk^1$ is as defined in the first instance and $R^8$ is hydrogen and $R^9$ is lower alkyl, i.e. secondary amines. When it is desired to prepare the latter compounds a modification involving the protection of the secondary amine with a benzyl group or other suitable protecting group, see J. F. McOmie, cited above is especially convenient. For example, the aforementioned acid or ester intermediate of formula VII is reacted with an amine of formula $HNR^8R^9$ in which $R^8$ is benzyl and $R^9$ is lower alkyl according to the amidation step described above. The resulting media is N-alkylated on the indolic nitrogen, if desired, and then reduced with a complex metal hydride according to the above procedures. Thereafter the benzyl group is removed by hydrogenolysis in the presence of a catalyst, preferably 10% palladium on carbon, to afford the desired secondary amine compounds of formula I.

Still another modification relates to a more general reduction of the above amides of formula VII in which Z is $CONR^8R^9$ or $Alk^1$-$CONR^8R^9$ wherein $Alk^1$, $R^8$ and $R^9$ are as defined in the first instance. In other words this modification is applicable to the reduction of tertiary, secondary and primary amides, described herein, and is a preferred modification for the reduction of the latter two. In practising this modification, the aforementioned amide of formula VII is treated with triethyloxonium fluoroborate or dimethyl sulfate, see H. Bredereck, et al., Chem. Ber., 98, 2754 (1965), in an inert solvent, for example, methylene dichloride, whereby the corresponding iminoether fluoroborate or methyl sulfate salt is obtained, respectively. Subsequent reduction of the salt thus obtained with a complex metal hydride, similar to the reduction described peviously for the amides, yields the corresponding compounds of formula I. Alternatively, the above fluoroborate or methyl sulfate salt derived from a secondary or primary amide is decomposed by base treatment, for example, with 10% sodium hydroxide or triethylamine, to give the corresponding iminoether which is then reduced in a like manner to the desired compound of formula I.

When applying the aforementioned steps in the preparation of compounds of formula I in which $R^6$ is hydroxy or lower alkanoyloxy, it is preferable to use corresponding intermediates in which $R^6$ is benzyloxy followed by the appropriate transformations as noted previously to yield the desired-compounds of formula I.

b. Preparation and Conversion of Intermediates of Formula VII (Z = $CONR^8R^9$ and $Alk^1$—$CONR^8R^9$).

The intermediates of formula VII in which $R^7$ is hydrogen and Z is $CONR^8R^9$ and $Alk^1$-$CONR^8R^9$ wherein $R^8$, $R^9$ and $Alk^1$ are as defined in the first instance, described in the previous section, are also obtained directly by utilizing the appropriate starting materials of formula II and α-, β-, γ- or δ-ketoamides of formula

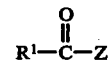

in which $R^1$ is as defined above and Z is $CONR^8R^9$ or $Alk^1$—$CONR^8R^9$ in which $Alk^1$, $R^8$ and $R^9$ are as defined above. The ketoamides required for this condensation are either known, for example, pyruvamide or α,α-dimethylacetoacetamide, or they are prepared by know methods, for instance, see "Rodd's Chemistry of the Carbon Compounds," cited above, Vol. 1d, pp. 226–274.

Thereafter these amides are converted by the reduction process, described above, to the compounds of formula I in which $R^1$, $R^2$, $R^3$, $R^4$, $R^5$, $R^6$, and X are as defined in the first instance, $R^7$ is hydrogen and Y is —Alk-$NR^8R^9$ in which Alk is $CH_2$ or $Alk^1$—$CH_2$ wherein $Alk^1$ is as defined in the first instance and $R^8$ and $R^9$ are as defined in the first instance.

c. Preparation and Conversion of Intermediates of Formula VII (Z = $CH_2OCOR^{20}$ and $Alk^1$—$CH_2OCOR^{20}$)

Intermediates of formula VII in which $R^7$ is hydrogen and Z is $CH_2OCOR^{20}$ and $Alk^1$-$CH_2OCOR^{20}$ in which $Alk^1$ and $R^{20}$ are as defined in the first instance, are obtained when a starting material of formula II ($R^7 =$ H) is condensed with a ketoalcohol lower alkanoic acid ester of formula $R^1COCH_2OCOR^{20}$ or $R^1CO$-$Alk^1$-$CH_2OCOR^{20}$ in which $R^1$, $Alk^1$ and $R^{20}$ are as defined in the first instance in the presence of a suitable acid catalyst according to the conditions described above for the condensation (II + VI→VII). The ketoalcohol lower alkanoic acid esters are either known, for example, acetonyl acetate or 5-acetoxypentan-2-one, or are prepared by known methods, for instance, see "Rodd's Chemistry of the Carbon Compounds," cited above, Vol. 1d, pp. 49–54.

These intermedites of formula VII may then be utilized for the preparation of compounds of formula I of this invention in the following manner. The intermediate is hydrolyzed with an aqueous alcoholic solution of a suitable alkali, for example, sodium hydroxide in aqueous methanol to afford the corresponding primary alcohol. The primary alcohol is then oxidized to the corresponding aldehyde. Although a variety of methods are known for the oxidation of a primary alcohol to its corresponding aldehyde, see for example, "Rodd's Chemistry of the Carbon Compounds," cited above, Vol. 1c, pp. 4 – 10, we have found that the method of K. E. Pfitzner and J. G. Moffat, J. Am. Chem. Soc., 87, 5670 (1965), using N,N-dicyclohexylcarbodiimide and dimethyl sulfoxide in the presence of a suitable acid, for example, trifluoroacetic acid, is both efficacious and convenient. Thereafter the aldehyde is reacted with an amine of formula $HNR^8R^9$ in which $R^8$ and $R^9$ are as defined in the first instance according to the method of K. N. Campbell, et al., J. Amer. Chem. Soc., 70, 3868 (1948) in the case when the amine used is ammonia or a primary amine or according to the method of N. J. Leonard and J. V. Paukstelis, J. Org. Chem., 28, 1397 (1963) when the amine is a secondary amine to give the corresponding Schiff base of ammonium salt, respectively. The product so obtained is reduced with sodium borohydride, see E. Schenker, Angew. Chem., 73, 81 (1961), to yield compounds of formula I in which $R^1$, $R^2$, $R^3$, $R^4$, $R^5$, $R^6$ and X are as defined in the first instance, $R^7$ is hydrogen and Y is $-Alk-NR^8R^9$ in which Alk is $CH_2$ or $Alk^1-CH_2$ and $R^8$ and $R^9$ are as defined in the first instance.

Alternatively, the latter compounds of formula I are obtained by converting the above corresponding alcohol to a reactive intermediate such as the corresponding halide, mesylate or tosylate, which are then reacted with a two molar excess of an amine of formula $HNR^8R^9$ in which $R^8$ and $R^9$ are as defined in the first instance. Preferably this reaction is performed in a suitable inert solvent, for example, tetrahydrofuran, at the boiling point of the reaction mixture for a period of eight to 24 hours. In connection with alkylations of amines of formula $HNR^8R^9$ in which $R^8$ is hydrogen and $R^9$ is lower alkyl as disclosed herein, it is generally preferable to perform the alkylation with the corresponding N-benzyl derivative of said amine, i.e., an amine of formula $HNR^8R^9$ in which $R^8$ is benzyl and $R^9$ is lower alkyl. Thereafter, when all appropriate transformation have been performed, the N-benzyl group is removed by hydrogenolysis with a catalyst, preferably 10% palladium on carbon, to give the desired compounds of formula I.

Thereafter, and if desired, these latter compounds of formula I are converted to their corresponding derivatives in which $R^7$ is lower alkyl, lower alkenyl, propargyl phenyl(lower)alkyl or amino(lower)alkyl by N-alkylation with one molar equivalent of the appropriate organic halide in the manner described for the N-alkylation in section (a).

Alternatively, the above aldehyde is oxidized with a suitable oxidizing agent to yield the corresponding acid intermedates of formula VII ($R^7$ = H) described in section (a). Although a variety of suitable oxidizing agents may be used for this purpose, for example, silver oxide, alkaline permanganate, hydrogen peroxide, we prefer to use silver oxide according to the method of M. Delepine and P. Bonnet, Compt. rend., 149, 39 (1909).

Again alternatively, the above aldehyde is converted to its oxime which on reduction with a complex metal hydride yields the corresponding primary amine of formula I in which $R^1$, $R^2$, $R^3$, $R^4$, $R^5$, $R^6$ and X are as defined in the first instance, $R^7$ is hydrogen and Y is $-Alk-NR^8R^9$ in which Alk is $CH_2$ or $Alk^1-CH_2$ wherein $Alk^1$ is as defined in the first instance and $R^8$ and $R^9$ are hydrogen.

If desired these latter primary amine compounds of formula I may be N-alkylated on the indolic nitrogen in the manner described above with a molar equivalent of the appropriate organic halide to give the corresponding compounds of formula I in which $R^7$ is lower alkyl, lower alkenyl, propargyl, phenyl(lower)alkyl or Alk-$NR^8R^9$ wherein Alk, $R^8$ and $R^9$ are as defined in the first instance.

In turn these latter compounds of formula I may be further N-alkylated on the nitrogen of the primary amine with the appropriate lower alkyl halide to the corresponding compounds of formula I in which Y is $-Alk-NR^8R^9$ wherein Alk is $CH_2$ or $Alk^1-CH_2$ wherein $Alk^1$ is as defined in the first instance and $R^8$ is hydrogen or lower alkyl and $R^9$ is lower alkyl (i.e. secondary or tertiary amines with respect to Y). In this case depending on the particular derivative desired the N-alkylation is effected with one or two moles of the alkyl halide to give respectively the secondary ($R^8$ = H and $R^9$ = lower alkyl with respect to Y) or tertiary amine ($R^8$ = $R^9$ = lower alkyl with respect to Y). On the other hand the N-alkylation may be effected in two steps introducing a different alkyl group each time to afford the corresponding tertiary amine in which $R^8$ and $R^9$ are different lower alkyls with respect to Y.

When it is desired to prepare the above tertiary amine compounds in which $R^8$ or $R^9$ are either or both methyl, an alternative alkylation method comprises reacting the appropriate corresponding primary or secondary amine with an aqueous mixture of a substantial excess of formaldehyde and formic acid according to the conditions of the Eschweiler-Clarke reaction, see M. L. Moore, Organic Reactions, 5, 301 (1949), whereby N-methylation is effected.

Another N-alkylation method which is applied to the above primary and secondary amines involve acylation with a lower alkanoic anhydride or acid halide and subsequent reduction of the resulting amide.

Furthermore, the above primary amines are used to prepare compounds of formula I in which Y is $-Alk-NR^8R^9$ wherein Alk is $CH_2$ or $Alk^1-CH_2$ and $R^8$ and $R^9$ together with the nitrogen atom to which they are joined form a heterocyclic amine radical as defined in the first instance. When used in this manner the primary amines are subjected to known N-alkylation methods, for example, see method J in Moffett, cited above, with the appropriate $\alpha,\omega$-dibromides, or $\alpha,\omega$-dibromides, for example, tetramethylene dibromide, pentamethylene dibromide bis(2-chloroethyl)ether, bis(2-chloroethyl)-benzylamine followed by hydrogenation in the presence of 10% palladium on carbon to remove the protecting benzyl group, a bis(2-chloroethyl)lower alkylamine or a bis(2-chloroethyl)-N-[hydroxy(lower)alkyl]amine, to give the corresponding, desired compound of formula I wherein Y is an amino(lower)alkyl in which the amino portion thereof is pyrrolidino, piperidino, morpholino, piperazino, 4-(lower)alkyl-1-piperazinyl or 4-[hydroxy(lower)alkyl]-1-piperazinyl, respectively.

If during the above N-alkylations it is desired to protect primary or secondary amine functions that are present in the $R^7$ portion of compounds of formula I, such protection may be afforded by the use of appropriate protecting groups, for example, a benzyl group; see also, J. F. W. McOmie in "Advances in Organic Chemistry," Vol. 3, R. A. Raphael, et al., Ed., Interscience Publishers, New York, 1963, pp. 191-294.

d. Preparation and Conversion of Intermediates of Formula VII (Z = Alk²—L).

Intermediates of formula VII in which R⁷ is hydrogen and Z is Alk²-L wherein Alk² and L are as defined in the first instance, are obtained when a starting material of formula II (R⁷ = H) is condensed with a β,γ- or δ-haloketone of formula R¹CO—Alk²—L in which R¹, Alk² and L are as defined in the first instance in the presence of a suitable acid catalyst according to the conditions described above for the condensation (II + VI→VII). The haloketones are either known, for example, 4-chlorobutan-2-one, or they are prepared by known methods, for instance, see "Rodd's Chemistry of Carbon Compounds," cited above, Vol. 1 c, pp. 70-71 and "Methoden der Organischen Chemie," Houben-Weyl, E. Muller, Ed., Vol. V/3, Georg Thieme Verlag, Stuttgart, 1962, pp. 511-1076.

Thereafter these intermediates of formula VII are treated with a two molar excess of amine of formula HNR⁸R⁹ in which R⁸ and R⁹ are as defined in the first instance to yield the compounds of formula I in which R¹, R², R³, R⁴, R⁵, R⁶ and X are as described in the first instance, R⁷ is hydrogen and Y is —Alk—NR⁸R⁹ in which Alk is Alk² as defined in the first instance and R⁸ and R⁹ are as defined in the first instance. Preferred conditions for this reaction include the use of a suitable inert solvent, for example, tetrahydrofuran, temperatures ranging from 40° - 100° C. or at the boiling point of the reaction mixture and a reaction time of from eight to 24 hours.

If desired the latter pyranoindoles and thiopyranoindoles may be N-alkylated on the indolic nitrogen with an appropriate lower alkyl halide or aminoalkyl halide according to the method described for the N-alkylation of the pyranoindoles and thiopyranoindoles in section (a).

e. Preparation and Conversion of Intermediates of Formula VII (Z = AlkNR⁸COR²¹)

Intermediates of formula VII in which R⁷ is hydrogen and Z is AlkNR⁸COR²¹ wherein Alk, R⁸ and R²¹ are as defined in the first instance are readily obtained by the condensation (II + VI→VII) by using ketoamides of formula

in which R¹, Alk, R⁸ and R²¹ are as defined in the first instance together with the appropriate starting material of formula II (R⁷ = H).

The ketoamides used herein are either known, for example, formamidoacetone [A. Treibs and W. Sutter, Chem. Ber., 84, 96 (1951)] and see [R. H. Wiley and O. H. Borum, J. Amer. Chem. Soc., 70, 2005 (1948)] or they are prepared by known procedures, for example, see "Methoden der Organischen Chemie", cited above, Vol. XI/1, 1957, especially pp. 58-62, 285-289 and 508-509, and F. F. Blicke, Organic Reactions, 1, 303 (1942).

Thereafter, reduction with a complex metal hydride and if desired N-alkylation of the indolic nitrogen as described in secton (a) converts the instant intermediates of formula VII to pyranoindoles of formula I in which R¹, R², R³, R⁴, R⁵, R⁶, R⁷, X are as defined in the first instance and Y is AlkNR⁸R⁹ in which Alk and R⁸ are as defined in the first instance and R⁹ is lower alkyl.

f. Preparation and Conversion of Intermediates of Formula VII (Z = Alk — NO₂)

Intermediates of formula VII in which R⁷ is hydrogen and Z is Alk-NO₂ wherein Alk is as defined in the first instance, are obtained by the condensation (II+VI→VII) when the starting materials of formula II(R⁷ = H) and appropriate α-, β-, γ-, and δ-nitroketones of formula

in which R¹ and Alk are as defined in the first instance are employed therein in the presence of a suitable acid catalyst. In this case trifluoroacetic acid is the preferred acid catalyst.

The nitroketones used herein are either known, for example, 1-nitro-2-propanone, N. Levy and C. W. Scaife, J. Chem. Soc., 1100, (1946) and 5-nitro-2-hexanone, H. Schechter, et al., J. Amer. Chem. Soc. 74, 3664 (1952) or they are prepared by known methods, for example, see Levy, and Scaife, cited above, Shechter, et al. cited above, "Rodd's Chemistry of Carbon Compounds", cited above, Vol. 1c, pp. 71-72 and "Methoden der Organischen Chemie", cited above, Vol. X/1, 1971, p. 203.

Thereafter, these intermediates of formula VII are reduced with a complex metal hydride, preferably lithium aluminum hydride, to afford the pyranoindoles of formula I in which R¹, R², R³, R⁴, R⁵, R⁶ and X are as defined in the first instance, Y is hydrogen and Z is —Alk—NR⁸R⁹ in which Alk is defined in the first instance and R⁸ and R⁹ are hydrogen.

If desired the latter compounds may be N-alkylated according to the methods described in section (c) to give the compounds of formula I in which R¹, R², R³, R⁴, R⁵, R⁶, R⁷ and X are as defined in the first instance and Y is Alk-NR⁸R⁹ in which Alk, R⁸ and R⁹ are as defined in the first instance.

g. Preparation and Conversion of Intermediates of Formula VII (Z = lower alkyl or phenyl(lower)alkyl.

Intermediates of formula VII (Z = lower alkyl or phenyl(lower)alkyl, R⁷ is hydrogen and R¹, R², R³, R⁴, R⁵, R⁶ and X are as defined in the first instance) are readily obtained by the condensation (II+VI→VII) by using the starting materials of formula II and the ketones of formula

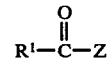

in which R¹ is as defined in the first instance and Z is lower alkyl or phenyl(lower)alkyl.

The ketones used herein are either available commercially, for example, acetone or phenylacetone, or they are prepared by conventional methods, for example, see P. Karrer, "Organic Chemistry", 2nd. ed., Elsevier Publishing Co., Inc., New York, 1946, pp. 149-169 and V. Migrdichian, "Organic Synthesis", Vol. 1, Reinhold Publishing Corp., New York, 1957, pp. 100-129.

These intermediates of formula VII are converted to the compounds of formula I in which R¹, R², R³, R⁴, R⁵, R⁶ and X are as defined in the first instance, R⁷ is —(Alk)—NR⁸R⁹ in which Alk, R⁸ and R⁹ are as defined in the first instance and Y is lower alkyl or phenyl(lower)alkyl by N-alkylation of the indolic nitrogen with the appropriate amino(lower)alkyl halide according to the method of N-alkylation described in section (a).

h. Preparation of Compounds of Formula VII (Z = Alk—NR⁸R⁹) ≡ Compounds of Formula I (Y = Alk—NR⁸R⁹)

The above described starting materials of formula II in which R², R³, R⁴, R⁵, R⁶, R⁷ and X¹ are as defined in the first instance are condensed in the presence of an acid catalyst with an aminoketone of formula R¹CO—Alk—NR⁸R⁹ in which R¹, Alk, R⁸ and R⁹ are as defined in the first instance to give directly the pyrano- and thiopyranoindole derivatives of formula I of this invention.

The requisite aminoketones for this reaction are either known, for example, 1-dimethylamino-3-butanone, 1-methylamino-3-pentanone, see F. F. Blicke, cited above, or they may be prepared by known procedures, for example, see "Methoden der Organischen Chemie", cited above, Vol. XI/1, 1957, pp. 58–62, 285–289 and 508–509.

In practicing this present condensation it is generally advantageous to utilize substantially equimolar amounts of the starting material of formula II and the aminoketone in the presence of an acid catalyst. In this particular condensation the amount of the aforementioned acid catalyst to employ ranges generally from about 1.01 to 100 molar equivalents with respect to the amount of aminoketone reactant, a range of from 1.05 to 10 molar equivalents being preferred. If more than one basic nitrogen is present in the reactants, for example, when R⁸ and R⁹ together with the nitrogen atom to which they are attached represent a piperazino radical, then additional acid catalyst is added to compensate for such basic nitrogens. Optionally, one may employ the acid addition salts of the aforementioned aminoketones and starting materials of formula II if R⁷ is an amino(lower)alkyl radical, for example the hydrochloride or the sulfate salt. In this case the amount of acid catalyst may range from 0.01 to 100 molar equivalents, preferably 0.1 to 10 molar equivalents. Boron trifluoride is a preferred acid catalyst for the present condensation. The reaction may be performed conveniently and advantageously without a solvent, although a high boiling solvent, for example, toluene, o-xylene or isobutyl ether, may be used. When the solvent is omitted, it is desirable to heat the reactants to a melt and stir the melt in an inert atmosphere, for example, nitrogen or helium. Reaction time and temperature depends on the particular reactants employed and may be varied. The most convenient reaction time is from one-half to 48 hours, preferably one-half to four hours, and reaction temperatures from 20° to 200° C, preferably 60° to 140° C. The reaction in each individual case is performed preferably at the lowest temperature at which the reaction proceeds smoothly and expeditiously with a minimum of decomposition.

In the case where the starting material is one of formula II in which Y is —S—SO₃Na or —S—SO₃K, it is preferable to have at least one equivalent of water present in the reaction mixture. This water may be added directly to the reaction or it may be included as part of the acid catalyst. Examples of the latter instance would be when p-toluenesulfonic acid containing water of crystallization or concentrated hydrochloric acid are employed as the acid catalyst.

With reference to the preparation of the pyranoindole and thiopyranoindole derivatives of formula Ia, the replacement of the starting material of formula II in any of the aforementioned processess (a) to (g) with the starting material of formula IIa,

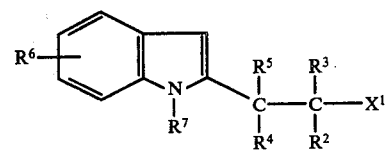

IIa in which R², R³, R⁴, R⁵, R⁶ and R⁷ are as defined in the first instance and X¹ is as defined in the first instance, gives the corresponding intermediate of formula VIIa,

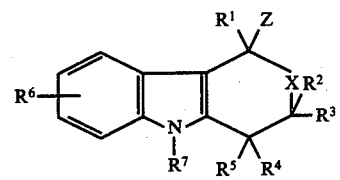

VIIa in which R¹, R², R³, R⁴, R⁵, R⁶, R⁷, X and Z are as defined hereinbefore. In the case where Z of said intermediate is Alk—NR⁸R⁹, the intermediate is the pyranoindole or thiopyranoindole of formula Ia. In the case where Z of said intermediate is other than —Alk—NR⁸R⁹, the intermediate is transformed to the corresponding pyranoindole or thiopyranoindole of formula Ia by the application of steps described hereinbefore for effecting the corresponding transformation of intermediates of formula VII to the compounds of formula I.

In other words the treatment of the starting material of formula IIa with a comound of formula

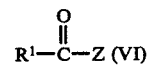

R¹—C—Z (VI)

in which R¹ and Z are as defined in the first instance according to the conditions of the condensation (II + VI → VII), described hereinbefore, gives the corresponding intermediate of formula VIIa, the latter compound being the corresponding compound of formula Ia or an intermediate therefor.

The requisite starting material of formula IIa in which X¹ is hydroxy and R², R³, R⁴, R⁵, R⁶, and R⁷ is hydrogen is obtained by treating 2-(2-indolyl)ethyl tosylate, described by T. Sakan, Tetrahedron Letters, 4925 (1968) with 10% sodium hydroxide solution. Optionally, the latter tosylate may be used in the condensation reaction in place of the starting material of formula IIa in which X¹ is hydroxy and R⁷ is hydrogen. The requisite starting material of formula IIa in which X¹ is hydroxy and R⁷ is defined in the first instance other than hydrogen is obtained by reacting the appropriately substituted indole, for example, N-methylindole, or N-ethylindole, with ethylene oxide or an appropriately substituted ethylene oxide according to the precedure of Julia, et al., cited above. The requisite starting material of formula IIa in which X¹ is mercapto, —S—SO₃—Na or —S—SO₃—K, are prepared from the above corresponding compounds of formula IIa in which X¹ is hydroxy according to the procedure described previously for the similar transformation of starting materials of formula II ($X^1$ = hydroxy) to starting materials of formula II ($X^1$ = mercapto —S—SO$_3$Na or —S—SO$_3$—K).

Finally, it is the intention to cover all changes and modifications of the embodiment of the invention herein chosen for the purpose of disclosure which are within the scope and spirit of this invention. Such changes and modification include those variations which depend on well known interconversions of amines, amides, acids and esters or alternation of the order of the steps in the processes disclosed herein.

For example, the act of subjecting the corresponding derivative of the starting material of formula II or IIa in which the indolic nitrogen is alkylated with a lower alkyl, lower alkenyl, propargyl, phenyl(lower)alkyl or amino(lower)alkyl, to condensation with an appropriate compound of formula VI according to the conditions of the key reaction taught in this present disclosure to yield the corresponding intermediate compound of formula VII or VIIa in which the indolic nitrogen is so alkylated would not depart from the scope or spirit of this invention.

More specifically exemplified, the compounds of formula I in which $R^7$ is lower alkyl are prepared conveniently and generally in good yields by using the starting material of formula II in which $R^7$ is lower alkyl and subjecting the starting material to treatment with the appropriate compound of formula

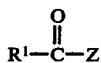

and subsequent conversions, if necessary, according to the teachings of the present disclosure.

The following examples illustrate further this invention.

EXAMPLE I

1-Methyl-1,3,4,9-tetrahydropyrano[3,4-b]indole-1-acetic acid (VII: $R^1$ = CH$_3$, $R^2$, $R^3$, $R^4$, $R^5$, $R^6$ and $R^7$ = H, X = O and Z = CH$_2$COOH)

Ethyl acetoacetate (23.4 g., 0.18 moles) is added to a solution of the starting material of formula II, tryptophol (10.0 g., 0.06 moles), in 200 ml. of benzene. After standing for 10 minutes, p-toluenesulfonic acid (1.3 g.) and about 5 g. of hydrated alkali-aluminum silicate (Molecular Sieves No. 4) are added. The mixture is subjected to reflux for thirty minutes, 600 mg. more of p-toluenesulfonic acid is added and refluxing continued for 2½ hours. The molecular sieves are collected and the benzene solution washed successively with 5% sodium bicarbonate and water, dried over sodium sulfate, and evaporated under reduced pressure to dryness affording an oil. The oil is subjected to chromatography on silica gel. Elution with 5% ether in benzene yields the ester, 1-methyl-1,3,4,9-tetrahydropyrano-[3,4-b]indole-1-acetic acid ethyl ester, as an oil, $\nu_{max}^{CHCl_3}$ 1715 cm$^{-1}$.

Hydrolysis of this ester to the title compound is effected as follows: The ester is dissolved in 230 ml. of methanol. To this is added 10 g. of KOH in 30 ml. of H$_2$O and the solution is allowed to stand at room temperature overnight. The methanol is evaporated, water added and the solution washed with benzene. The aqueous phase is acidified with 6N HCl, and extracted with benzene. This organic phase is washed with water, dried over sodium sulfate and evaporated to dryness to give an oil, which is crystallized from benzene containing a trace of petroleum ether to afford the title compound, m.p. 150 – 152° C., $\nu_{max}^{CHCl_3}$ 3325 and 1705 cm$^{-1}$.

An equivalent amount of methyl acetoacetate may replace ethyl acetoacetate in the procedure of this Example. In this case, 1-methyl-1,3,4,9-tetrahydropyrano[3,4-b]indoleacetic acid methyl ester, m.p. 87° – 90° C. after recrystallization from benzene-hexane, is obtained as the ester.

An equivalent amount of propyl acetoacetate may replace ethyl acetoacetate in the procedure of this Example. In this case, 1-methyl-1,3,4,9-tetrahydropyrano[3,4-b]indole-1-acetic acid propyl ester is obtained as the ester.

EXAMPLE 2

1-Methyl-1,3,4,9-tetrahydropyrano[3,4-b]indole-1-propionic acid (VII; $R^1$ = CH$_3$, $R^2$, $R^3$, $R^4$, $R^5$, $R^6$ and $R^7$ = H, X = O and Z = CH$_2$CH$_2$COOH)

A mixture of the starting material of formula II, tryptophol (500 mg.), levulinic acid (580 mg.), 75 ml. of benzene, 1.7 g. of phosphorus pentoxide and about 0.5 g. of diatomaceous earth (Celite) is stirred magnetically at room temperature for 15 minutes and then at 70° C. for 1½ hr. The reaction mixture is filtered. The filtrate is washed three times with 5N NaOH; the combined aqueous phase is washed twice with ether and then rendered acidic with cold 50% HCl. The aqueous phase is extracted with chloroform. The chloroform extract is dried (Na$_2$SO$_4$) and evaporated to dryness. The residue is crystallized from ethyl acetate-petroleum ether to afford the title compound, m.p. 104° – 110° C., nmr (CDCl$_3$) $\delta$1.47 (3H), 2.18 (4H), 2.74 (2H), 3.96 (2H), 7.18 (1H), 9.60 (1H).

The above title compound is also obtained by following the procedure of Example 1 but replacing ethyl acetoacetate with an equivalent amount of ethyl levulinate. In this case 1-methyl-1,3,4,9-tetrahydropyrano[3,4-b]indole-1-propionic acid ethyl ester, m.p. 116° – 118° C., $\nu_{max}^{CHCl_3}$ 1716 cm$^{-1}$, after crystallization from benzene-petroleum ether, is obtained as the ester prior to hydrolysis.

EXAMPLE 3

1-Methyl-1,3,4,9-tetrahydrothiopyrano[3,4-b]indole-1-acetic acid (VII; $R^1$ = CH$_3$, $R^2$, $R^3$, $R^4$, $R^5$, $R^6$ and $R^7$ = H, X = S and Z = CH$_2$COOH)

Indole-3-ethanethiol (1.5 g.) and methyl acetoacetate are mixed with 50 ml. of benzene and the solution heated for 30 min. (bath temperature 70° – 80° C.). p-Toluenesulfonic acid (0.15 g.) is added and the reaction mixture is subjected to reflux and stirring for 12 hours. Water formed in the reaction mixture during this period is collected by a water separator. After cooling the benzene solution is washed with 10% solution of sodium bicarbonate, water, saturated brine and dried over sodium sulfate. Evaporation of the benzene solution yields the ester, 1-methyl-1,3,4,9-tetrahydrothiopyrano[3,4-b]indole-1-acetic acid methyl ester as a semi-solid, $\nu_{max}^{CHCl_3}$ 1715 cm$^{-1}$.

This ester is then treated with aqueous alcoholic KOH in the manner described for the esters in Examples 1 and 2 to afford the title compound, m.p. 147° – 149° C., nmr (CDCl$_3$) $\delta$1.86 (S, 3H), 3.06, 8.12 (6H), 7.35

(multiplet, 4H), 8.71 (1H), 10.31 (1H), after recrystallization from benzene-hexane.

The procedures of Examples 1, or 3 are followed to prepared other compounds of formula VII in which $R^1$, $R^2$, $R^3$, $R^4$, $R^5$, $R^6$ and X are as defined in the first instance, $R^7$ is hydrogen and Z is $COOR^{19}$ or $Alk^1$—$COOR^{19}$ wherein $R^{19}$ and $Alk^1$ are as defined in the first instance. Examples of such compounds of formula VII are listed in Tables I and II. In each of these examples an equivalent amount of the starting material of formula II listed therein is used instead of the starting material of formula II described in the procedures of Examples 1 and 3. Note that in each of these examples the ester obtained prior to hydrolysis is a corresponding ester compound of formula VII.

Similarly, the procedure of Example 2 is used to prepare the products listed in Tables 1 and II. In this case an equivalent amount of the starting material of formula II, listed therein, is used instead of the starting material of formula II described in Example 2 and an equivalent amount of the corresponding ketoacid of formula VI is used instead of the ketoester of formula VI listed therein.

TABLE I

| | STARTING MATERIAL OF FORMULA II | | | | | KETOESTER OF FORMULA VI $R^1-\overset{\overset{O}{\|}}{C}-Alk^1-COOR^{19}$ | | | PRODUCT: [(prefix listed below)-1,3,4,9-Tetrahydropyrano-[3,4-b]indole-1-(suffix listed below] |
|---|---|---|---|---|---|---|---|---|---|
| Ex. | $R^2$ | $R^3$ | $R^4$ | $R^5$ | $R^6$ | X | $R^1$ | $Alk^1$-$CO$ | $R^{19}$ | PREFIX//SUFFIX |
| 4 | H | H | H | H | H | O | $CH_3$ | CO | $C_2H_5$ | 1-methyl//carboxylic acid |
| 5 | $CH_3$ | H | H | H | H | O | $C_2H_5$ | CO | $C_2H_5$ | 1-ethyl-3-methyl//carboxylic acid |
| 6 | n-$C_3H_7$ | H | H | H | 5-$CH_3$ | O | n-$C_3H_7$ | CO | $CH_3$ | 1,3-diisopropyl-6-methyl//carboxylic acid |
| 7 | $CH_3$ | $CH_3$ | H | H | 5-OH | O | $CH_3$ | CO | $CH_3$ | 1,3,3-trimethyl-6-hydroxy//carboxylic acid |
| 8 | H | H | H | H | 7-$C_2H_5$ | O | n-$C_3H_7$ | CO | $CH_3$ | 8-ethyl-1-propyl//carboxylic acid |
| 9 | H | H | i-$C_3H_7$ | H | H | O | ▷ | CO | $CH_3$ | 1-cyclopropyl-4-isopropyl//carboxylic acid |
| 10 | $CH_3$ | $CH_3$ | $C_2H_5$ | $C_2H_5$ | H | O | ⬠ | CO | $CH_3$ | 1-cyclopentyl-4,4-diethyl-3,3-dimethyl//carboxylic acid |
| 11 | H | H | $CH_3$ | H | H | O | $CH_3$ | $CH_2CO$ | $C_2H_5$ | 1,4-dimethyl//acetic acid |
| 12 | H | H | H | H | H | O | $C_2H_5$ | $CH_2CO$ | $C_2H_5$ | 1-ethyl//acetic acid, m.p. 137 – 140° C. |
| 13 | H | H | H | H | H | O | n-$C_3H_7$ | $CH_2CO$ | $C_2H_5$ | 1-propyl//acetic acid, m.p. 148 – 151° C. |
| 14 | H | H | H | H | H | O | i-$C_3H_7$ | $CH_2CO$ | $C_2H_5$ | 1-isopropyl//acetic acid, m.p. 150 – 152° C. |
| 15 | $CH_3$ | H | H | H | H | O | n-$C_3H_7$ | $CH_2CO$ | $C_2H_5$ | 3-methyl-1-propyl//acetic acid; m.p. 75 – 80° C. (Isomer A), m.p. 146 – 148° C. (Isomer B). |
| 16 | $CH_3$ | H | $C_2H_5$ | $CH_3$ | H | O | $C_2H_5$ | $CH_2CO$ | $C_2H_5$ | 1,4-diethyl-3-methyl//acetic acid, |
| 17 | H | H | H | H | H | O | $CH_3$ | $CH(CH_3)CO$ | $C_2H_5$ | α,1-dimethyl//acetic acid; m.p. 154 – 156° C (Isomer A), m.p. 163–165° C. (Isomer B). |
| 18 | H | H | H | H | H | O | ⬡ | $C(CH_3)_2CO$ | $C_2H_5$ | 1-cyclohexyl-α,α-dimethyl//acetic acid |
| 19 | H | H | H | H | H | O | t-$C_4H_9$ | $CH_2CO$ | $C_2H_5$ | 1-t-butyl//acetic acid m.p. 210 – 212° C. |
| 20 | H | H | H | H | H | O | n-$C_4H_9$ | $CH_2CO$ | $C_2H_5$ | 1-butyl//acetic acid, m.p. 124 – 127° C. |
| 21 | H | H | H | H | 7-$CH_3$ | O | n-$C_3H_7$ | $CH_2CO$ | $C_2H_5$ | 8-methyl-1-propyl//acetic acid m.p. 127 – 128° C. |
| 22 | H | H | H | H | 5-Br | O | $C_2H_5$ | $CH_2CO$ | $C_2H_5$ | 6-bromo-1-ethyl//acetic acid m.p. 182 – 184° C. |
| 23 | H | H | H | H | 5-$OCH_3$ | O | $CH_3$ | $CH_2CO$ | $CH_3$ | 6-methoxy-1-methyl//acetic acid, m.p. 142 – 143° C. |
| 24 | H | H | H | H | 5-$OCOCH_3$ | O | $CH_3$ | $CH_2CO$ | $C_2H_5$ | 6-acetoxy-1-methyl//acetic acid, m.p. 142 – 143° C. |
| 25 | H | H | H | H | 5-benzyloxy | O | $CH_3$ | $CH_2CO$ | $C_2H_5$ | 6-benzyloxy-1-methyl//acetic acid, m.p. 163.5° C. |
| 26 | H | H | H | H | 4-$CH_3$ | O | n-$C_3H_7$ | $CH_2CO$ | $C_2H_5$ | 5-methyl-1-propyl//acetic acid, m.p. 177 – 178° C. |
| 27 | H | H | H | H | 6-$CH_3$ | O | n-$C_3H_7$ | $CH_2CO$ | $C_2H_5$ | 7-methyl-1-propyl//acetic acid, m.p. 157 – 158° C. |
| 28 | H | H | H | H | 5-$NO_2$ | O | n-$C_3H_7$ | $CH_2CO$ | $C_2H_5$ | 6-nitro-1-propyl//acetic acid, m.p. 119 – 120° C. |
| 29 | H | H | $CH_3$ | $CH_3$ | H | O | n-$C_3H_7$ | $CH_2CO$ | $C_2H_5$ | 4,4-dimethyl-1-propyl//acetic acid, |

TABLE I-continued

| | STARTING MATERIAL OF FORMULA II | | | | | | KETOESTER OF FORMULA VI $R^1-\overset{O}{\underset{\|}{C}}-Alk^1-COOR^{19}$ | | | PRODUCT: [(prefix listed below)-1,3,4,9-Tetrahydropyrano-[3,4-b]indole-1-(suffix listed below] |
|---|---|---|---|---|---|---|---|---|---|---|
| Ex. | $R^2$ | $R^3$ | $R^4$ | $R^5$ | $R^6$ | X | $R^1$ | $Alk^1$-CO | $R^{19}$ | PREFIX//SUFFIX |
| 30 | $CH_3$ | $CH_3$ | H | H | 5-$OC_2H_5$ | O |  | $CH(C_2H_5)CO$ | $C_2H_5$ | m.p. 184 – 185° C. 1-cyclopropyl-α,α-diethyl-3,3-dimethyl-6-ethoxy//acetic acid |
| 31 | $CH_3$ | $CH_3$ | $C_2H_5$ | $C_2H_5$ | 6-$C_2H_5$ | O |  | $C(CH_3)_2CO$ | $C_2H_5$ | 1-cyclohexyl-α,α,3,3-tetramethyl-4,4,7-triethyl//acetic acid |
| 32 | $CH_3$ | H | n-$C_3H_7$ | n-$C_3H_7$ | 4-n-$C_3H_7$ | O | $C_2H_5$ | $CH(CH_3)CO$ | $C_2H_5$ | α,3-dimethyl-1-ethyl-4,4,5-tripropyl//acetic acid |
| 33 | H | H | H | H | H | O | n-$C_3H_7$ | $C(CH_3)_2CO$ | $C_2H_5$ | α,α-dimethyl-1-propyl//acetic acid |
| 34 | $C_2H_5$ | $C_2H_5$ | $C_2H_5$ | $C_2H_5$ | 4-$C_2H_5$ | O | t-$C_4H_9$ | $C(i-C_3H_7)_2CO$ | $C_2H_5$ | 1-t-butyl-α,α-diisopropyl-3,3,4,4,5-pentaethyl//acetic acid |
| 35 | H | H | H | H | 4-I | O | i-$C_3H_7$ | $CH_2CH_2CO$ | $C_2H_5$ | 5-iodo-1-isopropyl//propionic acid |
| 36 | $CH_3$ | $CH_3$ | $CH_3$ | $CH_3$ | 7-O$\overset{O}{\underset{\|}{C}}$CH$_3$ | O | $C_2H_5$ | $CH_2CH(CH_3)CO$ | $C_2H_5$ | 8-acetoxy-1-ethyl-α,3,3,4,4,-pentamethyl//propionic acid |
| 37 | H | H | H | H | 6-OH | O | n-$C_3H_7$ | $CH_2C(C_2H_5)_2CO$ | $C_2H_5$ | β,β-diethyl-7-hydroxy 1-propyl//propionic acid |
| 38 | $CH_3$ | H | H | H | 7-$NO_2$ | O |  | $CH(n-C_3H_7)CH_2CO$ | $C_2H_5$ | 1-cyclobutyl-3-methyl-8-nitro-α-propyl//propionic acid |
| 39 | H | H | $CH_3$ | H | 5-$CH_3$ | O |  | $C(CH_3)_2C(CH_3)_2CO$ | $C_2H_5$ | 1-cyclopropyl-α,α,β,β,4,6-hexamethyl//propionic acid |
| 40 | $CH_3$ | H | H | H | H | O | $CH_3$ | $CH_2C(n-C_3H_7)_2CO$ | $C_2H_5$ | 1,3-dimethyl-α,α-dipropyl//propionic acid |
| 41 | $CH_3$ | H | $C_2H_5$ | $C_2H_5$ | H | O | $C_2H_5$ | $CH(CH_3)C(CH_3)_2CO$ | $CH_3$ | α,α,β,3-tetramethyl-1,4,4-triethyl//propionic acid |
| 42 | H | H | $CH_3$ | $CH_3$ | H | O | $C_2H_5$ | $C(CH_3)_2CH_2CO$ | $CH_3$ | 1-ethyl-β,β,4,4-tetramethyl//propionic acid |
| 43 | H | H | n-$C_3H_7$ | H | 4—$\overset{O}{\underset{\|}{O}}$O$C_2H_5$ | O |  | $C(C_2H_5)_2C(C_2H_5)CO$ | $CH_3$ | 1-cyclopentyl-5-propionoxy-4-propyl-α,β,β-triethyl// propionic acid |
| 44 | n-$C_3H_7$ | H | H | H | 4-$OCH_3$ | O | n-$C_3H_7$ | $CH_2CH(CH_3)CO$ | $C_2H_5$ | 1,3-dipropyl-5-methoxy α-methyl//propionic acid |
| 45 | $C_2H_5$ | H | H | H | 5-$NO_2$ | O | $CH_3$ | $C(C_2H_5)_2C(C_2H_5)_2CO$ | $C_2H_5$ | 1-methyl-6-nitro-α,α,-β,β,3-pentaethyl//propionic acid |
| 46 | $C_2H_5$ | $C_2H_5$ | H | H | 4-$C_2H_5$ | O | n-$C_3H_7$ | $CH(n-C_3H_7)CH_2CO$ | $CH_3$ | β,1-dipropyl-3,3,5-triethyl//propionic acid |
| 47 | H | H | H | H | 6-$OC_2H_5$ | O |  | $CH(C_2H_5)CH(C_2H_5)CO$ | $C_2H_5$ | 1-cyclopropyl-α,β-diethyl-7-ethoxy//propionic acid |
| 48 | H | H | H | H | H | O | $CH_3$ | $CH_2CH_2CH_2CO$ | $C_2H_5$ | 1-methyl//butyric acid m.p. 132 – 135° C. |
| 49 | $CH_3$ | H | H | H | H | O | $C_2H_5$ | $CH(CH_3)CH_2CH_2CO$ | $C_2H_5$ | γ,3-dimethyl-1-ethyl//butyric acid |
| 50 | $CH_3$ | $CH_3$ | H | H | H | O | n-$C_3H_7$ | $C(C_2H_5)_2CH_2CH_2CO$ | $C_2H_5$ | γ,γ-diethyl-3,3-dimethyl-1-propyl//butyric acid |
| 51 | $CH_3$ | $CH_3$ | n-$C_3H_7$ | H | H | O |  | $C(n-C_3H_7)_2CH(n-C_3H_7)CH_2CO$ | $C_2H_5$ | 1-cyclobutyl-3,3-dimethyl-β,γ,γ,4-tetrapropyl//butyric acid |
| 52 | H | H | $C_2H_5$ | $C_2H_5$ | 6-Cl | O | $CH_3$ | [C($C_2H_5$)$_2$]$_2$—CCO $H_5C_2$ H | $C_2H_5$ | 7-chloro-α,β,β,γ,γ,4,-heptaethyl-1-methyl//butyric acid |
| 53 | H | H | $CH_3$ | H | 4-$CH_3$ | O | $C_2H_5$ | [C($CH_3$)$_2$]$_3$CO | $C_2H_5$ | 1-ethyl-α,α,β,β,γ,γ,4-4,5-octamethyl//butyric acid |
| 54 | $C_2H_5$ | $C_2H_5$ | $C_2H_5$ | H | 5-O$\overset{O}{\underset{\|}{C}}$CH$_3$ | O | n-$C_3H_7$ | $CH(C_2H_5)[C(C_2H_5)]_2CO$ | $C_2H_5$ | 6-acetoxy-α,α,β,β,γ,3,-3,4-octaethyl-1-propy-butyric acid |
| 55 | H | H | $CH_3$ | $CH_3$ | 7-$OCH_3$ | O |  | $CH_2[C(CH_3)_3]_2CO$ | $C_2H_5$ | 1-cyclobutyl-α,α,β,β,4,4-hexamethyl-8-methoxy//butyric acid |
| 56 | H | H | H | H | 4-Br | O |  | $CH_2CH(CH_3)C(CH_3)_2CO$ | $C_2H_5$ | 5-bromo-1-cyclopentyl-α,α,β-trimethyl//butyric acid |
| 57 | $CH_3$ | $CH_3$ | H | H | 4-n-$C_3H_7$ | O |  | $CH_2CH_2C(C_2H_5)_2CO$ | $C_2H_5$ | 1-cyclopropyl-α,α-diethyl-3,3-dimethyl-5-propyl//butyric acid |
| 58 | H | H | H | H | 7-$C_2H_5$ | O | $C_2H_5$ | $CH_2CH_2CH(CH_3)CO$ | $C_2H_5$ | 1,8-diethyl-α-methyl// |

TABLE I-continued

| Ex. | STARTING MATERIAL OF FORMULA II | | | | | | KETOESTER OF FORMULA VI $R^1-\overset{O}{\overset{\|}{C}}-Alk^1-COOR^{19}$ | | | PRODUCT: [(prefix listed below)-1,3,4,9-Tetrahydropyrano-[3,4-b]indole-1-(suffix listed below] |
|---|---|---|---|---|---|---|---|---|---|---|
| | $R^2$ | $R^3$ | $R^4$ | $R^5$ | $R^6$ | X | $R^1$ | $Alk^1$-CO | $R^{19}$ | PREFIX//SUFFIX |
| 59 | $CH_3$ | $CH_3$ | $CH_3$ | H | 5-F | O | n-$C_4H_9$ | $[CH(CH_3)]_3CO$ | $C_2H_5$ | butyric acid 1-butyl-6-fluoro-$\alpha,\beta$, $\gamma$,3,3,4-hexamethyl// butyric acid |
| 60 | $CH_3$ | $CH_3$ | H | H | 4-$CH_3$ | O | n-$C_3H_7$ | $CH(C_2H_5)CH_2CH(C_2H_5)CO$ | $C_2H_5$ | $\alpha,\gamma$-diethyl-1-propyl-3,3,5-trimethyl// butyric acid |
| 61 | $C_2H_5$ | H | H | H | 6-$NO_2$ | O | n-$C_4H_9$ | $[C(CH_3)_2]_3CO$ | $C_2H_5$ | 1-butyl-3-ethyl-7-nitro-$\alpha,\beta,\gamma$-trimethyl//butyric acid |
| 62 | $CH_3$ | $CH_3$ | H | H | 4-n-$C_3H_7$ | O | n-$C_3H_7$ | $CH_2[CH(C_2H_5)]_2CO$ | $C_2H_5$ | $\alpha,\beta$-diethyl-3,3-dimethyl-1,5-dipropyl// butyric acid |
| 63 | H | H | H | H | 7-OH | O | $C_2H_5$ | $C(CH_3)_2CH_2C(CH_3)_2CO$ | $C_2H_5$ | 1-ethyl-8-hydroxy-$\alpha,\alpha,\gamma,\gamma$-tetramethyl// butyric acid |
| 64 | $CH_3$ | H | $CH_3$ | H | 4-$OC_2H_5$ | O | $C_2H_5$ | $[C(CH_3)_2]_3CO$ | $C_2H_5$ | 5-ethoxy-1-ethyl-$\alpha,\alpha,$-$\beta,\beta,\gamma,\gamma$,3,4-octomethyl//butyric acid |
| 64a | H | H | H | H | 4-$CH_3$ | O | $CH_3$ | $CH_2CO$ | $C_2H_5$ | 1,5-dimethyl//acetic acid, m.p. 150–152° C. |
| 64b | H | H | H | H | 4-Cl | O | $CH_3$ | $CH_2CO$ | $CH_3$ | 5-chloro-1-methyl// acetic acid, m.p. 183–184° C. |

TABLE II

| EX. | STARTING MATERIAL OF FORMULA II | | | | | | KETOESTER OF FORMULA VI $R^1-\overset{O}{\overset{\|}{C}}-Alk^1-COOR^{19}$ | | | PRODUCT: [(PREFIX LISTED BELOW)-1,3,4,9-TETRAHYDRO-THIOPYRANO-[3,4-b] INDOLE-1-(SUFFIX LISTED BELOW)] |
|---|---|---|---|---|---|---|---|---|---|---|
| | $R^2$ | $R^3$ | $R^4$ | $R^5$ | $R^6$ | X | $R^1$ | $Alk^1$-CO | $R^1$ | PREFIX//SUFFIX. |
| 65 | H | H | H | H | H | S | $CH_3$ | CO | $C_2H_5$ | 1-methyl//carboxylic acid |
| 66 | $CH_3$ | H | H | H | H | S | $C_2H_5$ | CO | $C_2H_5$ | 1-ethyl-3-methyl// carboxylic acid |
| 67 | i-$C_3H_7$ | H | H | H | 5-$CH_3$ | S | i-$C_3H_7$ | CO | $CH_3$ | 1,3-diisopropyl-6-methyl//carboxylic acid |
| 68 | $CH_3$ | $CH_3$ | H | H | 5-OH | S | $CH_3$ | CO | $CH_3$ | 1,3,3-trimethyl-6-hydroxy-1-(1-propyl)// carboxylic acid |
| 69 | H | H | H | H | 7-$C_2H_5$ | S | n-$C_3H_7$ | CO | $CH_3$ | 8-ethyl-1-propyl// carboxylic acid |
| 70 | H | H | i-$C_3H_7$ | H | H | S | cyclopropyl | CO | $CH_3$ | 1-cyclopropyl-4-isopropyl//carboxylic acid |
| 71 | $CH_3$ | $CH_3$ | $C_2H_5$ | $C_2H_5$ | H | S | cyclopentyl | CO | $CH_3$ | 1-cyclopentyl-4,4-diethyl-3,3-dimethyl// carboxylic acid |
| 72 | H | H | $CH_3$ | H | H | S | $CH_3$ | $CH_2CO$ | $C_2H_5$ | 1,4-dimethyl//acetic acid |
| 73 | H | H | H | H | H | S | $C_2H_5$ | $CH_2CO$ | $C_2H_5$ | 1-ethyl//acetic acid, m.p. 138° C. |
| 74 | H | H | H | H | H | S | n-$C_3H_7$ | $CH_2CO$ | $C_2H_5$ | 1-propyl//acetic acid, m.p. 127 – 129° C. |
| 75 | H | H | H | H | H | S | i-$C_3H_7$ | $CH_2CO$ | $C_2H_5$ | 1-isopropyl//acetic acid |
| 76 | $CH_3$ | H | H | H | H | S | n-$C_3H_7$ | $CH_2CO$ | $C_2H_5$ | 3-methyl-1-propyl// acetic acid |
| 77 | $CH_3$ | H | $C_2H_5$ | $CH_3$ | H | S | $C_2H_5$ | $CH_2CO$ | $C_2H_5$ | 1,4-diethyl-3-methyl// acetic acid |
| 78 | H | H | H | H | H | S | $CH_3$ | $CH(CH_3)CO$ | $C_2H_5$ | $\alpha$,1-dimethyl//acetic acid |
| 79 | H | H | H | H | H | S | cyclohexyl | $C(CH_3)_2CO$ | $C_2H_5$ | 1-cyclohexyl-$\alpha,\alpha$-dimethyl//acetic acid |
| 80 | H | H | H | H | H | S | t-$C_4H_9$ | $CH_2CO$ | $C_2H_5$ | 1-t-butyl//acetic acid |
| 81 | H | H | H | H | H | S | n-$C_4H_9$ | $CH_2CO$ | $C_2H_5$ | 1-butyl//acetic acid |
| 82 | H | H | H | H | 7-$CH_3$ | S | n-$C_3H_7$ | $CH_2CO$ | $C_2H_5$ | 8-methyl-1-propyl// acetic acid |
| 83 | H | H | H | H | 5-Br | S | n-$C_3H_7$ | $CH_2CO$ | $C_2H_5$ | 6-bromo-1-propyl// acetic acid |
| 84 | H | H | H | H | 5-$OCH_3$ | S | $CH_3$ | $CH_2CO$ | $CH_3$ | 6-methoxy-1-methyl// acetic acid |
| 85 | H | H | H | H | 5-$OCOCH_3$ | S | $CH_3$ | $CH_2CO$ | $C_2H_5$ | 6-acetoxy-1-methyl// acetic acid |

TABLE II-continued

| EX. | STARTING MATERIAL OF FORMULA II | | | | | X | KETOESTER OF FORMULA VI $R^1-\overset{O}{\overset{\|}{C}}-Alk^1-COOR^{19}$ | | PRODUCT: [(PREFIX LISTED BELOW)-1,3,4,9-TETRAHYDRO-THIOPYRANO-[3,4-b]INDOLE-1-(SUFFIX LISTED BELOW)] | |
|---|---|---|---|---|---|---|---|---|---|---|
| | $R^2$ | $R^3$ | $R^4$ | $R^5$ | $R^6$ | | $R^1$ | $Alk^1$-CO | $R^1$ | PREFIX//SUFFIX |
| 86 | H | H | H | H | 5-benzyloxy | S | $CH_3$ | $CH_2CO$ | $C_2H_5$ | 6-benzyloxy-1-methyl//acetic acid |
| 87 | H | H | H | H | 4-$CH_3$ | S | n-$C_3H_7$ | $CH_2CO$ | $C_2H_5$ | 5-methyl-1-propyl//acetic acid |
| 88 | H | H | H | H | 6-$CH_3$ | S | n-$C_3H_7$ | $CH_2CO$ | $C_2H_5$ | 7-methyl-1-propyl//acetic acid |
| 89 | H | H | H | H | 7-F | S | $CH_3$ | $C(C_2H_5)_2CO$ | $C_2H_5$ | $\alpha,\alpha$-diethyl-8-fluoro-1-methyl//acetic acid |
| 90 | $CH_3$ | $CH_3$ | H | H | 5-Cl | S | n-$C_3H_7$ | $CH(iC_3H_7)CO$ | $C_2H_5$ | 6-chloro-3,3-dimethyl-$\alpha$-isopropyl-1-propyl//acetic acid |
| 91 | $CH_3$ | $CH_3$ | H | H | 5-$OC_2H_5$ | S |  | $CH(C_2H_5)CO$ | $C_2H_5$ | 1-cyclopropyl-$\alpha,\alpha$-diethyl-3,3-dimethyl-6-ethoxy//acetic acid |
| 92 | $CH_3$ | $CH_3$ | $C_2H_5$ | $C_2H_5$ | 6-$C_2H_5$ | S |  | $C(CH_3)_2CO$ | $C_2H_5$ | 1-cyclohexyl-$\alpha,\alpha$,3,3-tetramethyl-4,4,7-triethyl//acetic acid |
| 93 | $CH_3$ | H | n-$C_3H_7$ | n-$C_3H_7$ | 4-n-$C_3H_7$ | S | $C_2H_5$ | $CH(CH_3)CO$ | $C_2H_5$ | $\alpha$,3-dimethyl-1-ethyl-4,4,5-tripropyl//acetic acid |
| 94 | H | H | H | H | H | S | n-$C_3H_7$ | $C(CH_3)_2CO$ | $C_2H_5$ | $\alpha,\alpha$-dimethyl-1-propyl//acetic acid |
| 95 | $C_2H_5$ | $C_2H_5$ | $C_2H_5$ | $C_2H_5$ | 4-$C_2H_5$ | S | t-$C_4H_9$ | $C(i-C_3H_7)_2CO$ | $C_2H_5$ | 1-t-butyl-$\alpha,\alpha$-diisopropyl-3,3,4,4-5-pentaethyl//acetic acid |
| 96 | H | H | H | H | H | S | $CH_3$ | $CH_2CH_2CO$ | $C_2H_5$ | 1-methyl//propionic acid |
| 97 | $CH_3$ | $CH_3$ | $CH_3$ | $CH_3$ | 7-$OCCH_3$ ($\overset{O}{\overset{\|}{}}$) | S | $C_2H_5$ | $CH_2CH(CH_3)CO$ | $C_2H_5$ | 8-acetoxy-1-ethyl-$\alpha$,3,3,4,4-pentamethyl//propionic acid |
| 98 | H | H | H | H | 6-OH | S | n-$C_3H_7$ | $CH_2C(C_2H_5)_2CO$ | $C_2H_5$ | $\beta,\beta$-diethyl-7-hydroxy-1-propyl//propionic acid |
| 99 | $CH_3$ | H | H | H | 7-$NO_2$ | S |  | $CH(n-C_3H_7)CH_2CO$ | $C_2H_5$ | 1-cyclobutyl-3-methyl-8-nitro-$\alpha$-propyl//propionic acid |
| 100 | H | H | $CH_3$ | H | 5-$CH_3$ | S |  | $C(CH_3)_2C(CH_3)_2CO$ | $C_2H_5$ | 1-cyclopropyl-$\alpha,\alpha,\beta,\beta$-4,6-hexamethyl//propionic acid |
| 101 | $CH_3$ | H | H | H | H | S | $CH_3$ | $CH_2C(n-C_3H_7)_2CO$ | $C_2H_5$ | 1,3-dimethyl-$\alpha,\alpha$-dipropyl//propionic acid |
| 102 | $CH_3$ | H | $C_2H_5$ | $C_2H_5$ | H | S | $C_2H_5$ | $CH(CH_3)C(CH_3)_2CO$ | $CH_3$ | 1,4,4-triethyl-$\alpha,\alpha,\beta$-3-tetramethyl//propionic acid |
| 103 | H | H | $CH_3$ | $CH_3$ | H | S | $C_2H_5$ | $C(CH_3)_2CH_2CO$ | $CH_3$ | 1-ethyl-$\beta,\beta$,4,4-tetramethyl//propionic acid |
| 104 | H | H | n-$C_3H_7$ | H | 4-$OCC_2H_5$ ($\overset{O}{\overset{\|}{}}$) | S |  | $C(C_2H_5)_2C(C_2H_5)CO$ | $CH_3$ | 1-cyclopentyl-5-propionoxy-4-propyl-$\alpha,\beta,\beta$-triethyl//propionic acid |
| 105 | n-$C_3H_7$ | H | H | H | 4-$OCH_3$ | S | n-$C_3H_7$ | $CH_2CH(CH_3)CO$ | $C_2H_5$ | 1,3-dipropyl-5-methoxy-$\alpha$-methyl//propionic acid |
| 106 | $C_2H_5$ | H | H | H | 5-$NO_2$ | S | $CH_3$ | $C(C_2H_5)_2C(C_2H_5)_2CO$ | $C_2H_5$ | 1-methyl-6-nitro-$\alpha,\alpha,\beta,\beta$,3-pentaethyl//propionic acid |
| 107 | $C_2H_5$ | $C_2H_5$ | H | H | 4-$C_2H_5$ | S | n-$C_3H_7$ | $CH(n-C_3H_7)CH_2CO$ | $CH_3$ | $\beta$,1-dipropyl-3,3,5-triethyl//propionic acid |
| 108 | H | H | H | H | 6-$OC_2H_5$ | S |  | $CH(C_2H_5)CH(C_2H_5)CO$ | $C_2H_5$ | 1-cyclopropyl-$\alpha,\beta$-diethyl-7-ethoxy//propionic acid |
| 109 | H | H | H | H | H | S | $CH_3$ | $CH_2CH_2CH_2CO$ | $C_2H_5$ | 1-methyl//butyric acid |
| 110 | $CH_3$ | H | H | H | H | S | $C_2H_5$ | $CH(CH_3)CH_2CH_2CO$ | $C_2H_5$ | $\gamma$,3-dimethyl-1-ethyl//butyric acid |
| 111 | $CH_3$ | $CH_3$ | H | H | H | S | n-$C_3H_7$ | $C(C_2H_5)_2CH_2CH_2CO$ | $C_2H_5$ | $\gamma,\gamma$-diethyl-3,3-dimethyl-1-propyl//butyric acid |
| 112 | $CH_3$ | $CH_3$ | n-$C_3H_7$ | H | H | S |  | $C(n-C_3H_7)_2CH(n-C_3H_7)CH_2CO$ | $C_2H_5$ | 1-cyclobutyl-3,3-dimethyl-$\beta,\gamma,\gamma$,4-tetrapropyl//butyric acid |
| 113 | H | H | $C_2H_5$ | $C_2H_5$ | 6-Cl | S | $CH_3$ | $[C(C_2H_5)_2]_2CH(C_2H_5)CO$ | $C_2H_5$ | 7-chloro-$\alpha,\beta,\beta,\gamma,\gamma$-4,4-heptaethyl-1-methyl//butyric acid |
| 114 | H | H | $CH_3$ | H | 4-$CH_3$ | S | $C_2H_5$ | $[C(CH_3)_2]_3CO$ | $C_2H_5$ | 1-ethyl-$\alpha,\alpha,\beta,\beta,\gamma,\gamma$,4,5-octamethyl// |

TABLE II-continued

| | STARTING MATERIAL OF FORMULA II | | | | | | KETOESTER OF FORMULA VI $R^1-\overset{O}{\underset{\|}{C}}-Alk^1-COOR^{19}$ | | PRODUCT: [(PREFIX LISTED BELOW)-1,3,4,9-TETRAHYDRO-THIOPYRANO-[3,4-b]INDOLE-1-(SUFFIX LISTED BELOW)] | |
|---|---|---|---|---|---|---|---|---|---|---|
| EX. | $R^2$ | $R^3$ | $R^4$ | $R^5$ | $R^6$ | X | $R^1$ | $Alk^1$-CO | $R^1$ | PREFIX//SUFFIX. |
| 115 | $C_2H_5$ | $C_2H_5$ | $C_2H_5$ | H | 5-OCCH$_3$ (O=) | S | n-$C_3H_7$ | $CH(C_2H_5)[C(C_2H_5)_3]_2CO$ | $C_2H_5$ | butyric acid 6-acetoxy-$\alpha,\alpha,\beta,\beta,\gamma$,3,3,4-octaethyl-1-propyl//butyric acid |
| 116 | H | H | $CH_3$ | $CH_3$ | 7-$OCH_3$ | S | ☐ (cyclobutyl) | $CH_2[C(CH_3)_3]_2CO$ | $C_2H_5$ | 1-cyclobutyl-$\alpha,\alpha,\beta,\beta$,4,4-hexamethyl-8-methoxy//butyric acid |
| 117 | H | H | H | H | 4-Br | S | ⬠ (cyclopentyl) | $CH_2CH(CH_3)C(CH_3)_2CO$ | $C_2H_5$ | 5-bromo-1-cyclopentyl $\alpha,\alpha,\beta$-trimethyl// butyric acid |
| 118 | $CH_3$ | $CH_3$ | H | H | 4-n-$C_3H_7$ | S | △ (cyclopropyl) | $CH_2CH_2C(C_2H_5)_2CO$ | $C_2H_5$ | 1-cyclopropyl-$\alpha,\alpha$-diethyl-3,3-dimethyl-5-propyl//butyric acid |
| 119 | H | H | H | H | 7-$C_2H_5$ | S | $C_2H_5$ | $CH_2CH_2CH(CH_3)CO$ | $C_2H_5$ | 1,8-diethyl-$\alpha$-methyl//butyric acid |
| 120 | $CH_3$ | $CH_3$ | $CH_3$ | H | 5-F | S | n-$C_4H_9$ | $[CH(CH_3)]_3CO$ | $C_2H_5$ | 1-butyl-6-fluoro-$\alpha,\beta,\gamma$,3,3,4-hexamethyl//butyric acid |
| 121 | $CH_3$ | $CH_3$ | H | H | 4-$CH_3$ | S | n-$C_3H_7$ | $CH(C_2H_5)CH_2CH(C_2H_5)CO$ | $C_2H_5$ | $\alpha,\gamma$-diethyl-1-propyl-3,3,5-trimethyl butyric acid |
| 122 | $C_2H_5$ | H | H | H | 6-$NO_2$ | S | n-$C_4H_9$ | $[C(CH_3)_2]_3CO$ | $C_2H_5$ | 1-butyl-3-ethyl-7-nitro-$\alpha,\beta,\gamma$-trimethyl//butyric acid |
| 123 | $CH_3$ | $CH_3$ | H | H | 4-n-$C_3H_7$ | S | n-$C_3H_7$ | $CH_2[CH(C_2H_5)]_2CO$ | $C_2H_5$ | $\alpha,\beta$-diethyl-3,3-dimethyl-1,5-dipropyl//butyric acid |
| 124 | H | H | H | H | 7-OH | S | $C_2H_5$ | $C(CH_3)_2CH_2C(CH_3)_2CO$ | $C_2H_5$ | 1-ethyl-8-hydroxy-$\alpha,\alpha,\gamma,\gamma$-tetramethyl//butyric acid |
| 125 | $CH_3$ | H | $CH_3$ | H | 4-$OC_2H_5$ | S | $C_2H_5$ | $[C(CH_3)_2]_3CO$ | $C_2H_5$ | 5-ethoxy-1-ethyl-$\alpha,\alpha,\beta,\beta,\gamma,\gamma$,3,4-octomethyl//butyric acid |

EXAMPLE 126

N,N,1-Trimethyl-1,3,4,9-Tetrahydropyrano[3,4-b]Indole-1-Acetamide [VII; $R^1 = CH_3$, $R^2$, $R^3$, $R^4$, $R^5$, $R^6$ and $R^7 =$ H, X = O and Z = $CH_2CON(CH_3)_2$]

To a stirred solution of 1-methyl-1,3,4,9-tetrahydropyrano[3,4-b]indole-1-acetic acid (15 g, 0.061 mole), prepared as described in Example 1, in dry tetrahydrofuran (300 ml), cooled to −5° C., is added triethylamine (18.5 g, 0.183 mole), followed by ethyl chloroformate (16.6 g, 0.153 mole). The mixture is stirred at −5° C. for 2 hr. This mixture, which now contains the mixed anhydride of the above starting material, is added dropwise to a cooled 40% aqueous solution of the amine, dimethylamine (225 ml). The resulting mixture is stirred at room temperature for one-half hour. Most of the tetrahydrofuran is evaporated, and the residue partitioned between chloroform and water. The organic phase is washed with water, dried over sodium sulfate, and evaporated under reduced pressure. The residue is subjected to chromatography on silica gel. Elution with 20% ethyl acetate in benzene, followed by crystallization of the eluate from ethyl acetate affords the title compound, m.p. 149° – 151° C., $\nu_{max}^{CHCl_3}$ 3375, 1634 cm$^{-1}$.

In the same manner but replacing the 40% aqueous solution of dimethylamine with an equivalent amount of ammonium hydroxide (concentrated), methylamine (30% aqueous solution), n-hexylamine (20% aqueous solution), diethylamine (30% aqueous solution), isopropylamine (40% aqueous solution), ethylamine (70% aqueous solution), pyrrolidine (50% aqueous solution), piperidine, morpholine, N-methylpiperazine, 1-methyl-1,3,4,9-tetrahydropyrano[3,4-b]indole-1-acetamide, m.p. 158° – 160° C.,
N,1-dimethyl-1,3,4,9-tetrahydropyrano[3,4-b]indole-1-acetamide, m.p. 138° – 140° C.,
N-hexyl-1-methyl-1,3,4,9-tetrahydropyrano[3,4-b]indole-1-acetamide,
N,N-diethyl-1-methyl-1,3,4,9-tetrahydropyrano[3,4-b]indole-1-acetamide, m.p. 99° C., $\nu_{max}^{CHCl_3}$ 3350, 1620 cm$^{-1}$,
N-isopropyl-1-methyl-1,3,4,9-tetrahydropyrano[3,4-b]indole-1-acetamide, m.p. 151° – 153° C.,
N-ethyl-1-methyl-1,3,4,9-tetrahydropyrano[3,4-b]indole-1-acetamide, m.p. 152° – 153° C.,
1-[(1-methyl-1,3,4,9-tetrahydropyrano[3,4-b]indol-1-yl)acetyl]-pyrrolidine, m.p. 119° – 120° C.,
1-[(1-methyl-1,3,4,9-tetrahydropyrano[3,4-b]indol-1-yl)acetyl]-piperidine, m.p. 148° – 149° C.,
1-[(1-methyl-1,3,4,9-tetrahydropyrano[3,4-b]indol-1-yl)acetyl]-morpholine, m.p. 141° – 142° C., and
1-methyl-4-[(1-methyl-1,3,4,9-tetrahydropyrano[3,4-b]indol-1-yl)-acetyl]piperazine, are obtained respectively.

By following the procedure of Example 126 but using as starting material an equivalent amount of one of the acid compounds of formula VII, described in Examples 2 to 125, instead of 1-methyl-1,3,4,9-tetrahydropyrano[3,4-b]indole-1-acetic acid, and using an equivalent amount of an appropriate amine such as ammonia or a primary or secondary amine described in Example 126, then the corresponding amide compound of formula VII is obtained. Examples of such amides are listed as products in Tables III, IV, V and VI together with the appropriate starting material and amine used for the preparation of the amide. In each case the starting material is noted by the example in which it is prepared.

TABLE III

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 127 | 2 | $CH_3NH_2$ | N,1-dimethyl//propionamide, m.p. 149 – 150° C. |
| 128 | 2 | $NH_3$ | 1-methyl//propionamide |
| 129 | 2 | $(CH_3)_2NH$ | N,N,1-trimethyl//propionamide |
| 130 | 2 | $n-C_6H_{13}NH_2$ | N-hexyl-1-methyl//propionamide |
| 131 | 2 | $(C_2H_5)_2NH$ | N,N-diethyl-1-methyl//propionamide |
| 132 | 4 | $CH_3NH_2$ | N,1-dimethyl//carboxamide |
| 133 | 4 | $NH_3$ | 1-methyl//carboxamide, m.p. 188 – 189° C. |
| 134 | 4 | $(CH_3)_2NH$ | N,N,1-trimethyl//carboxamide |
| 135 | 4 | $n-C_6H_{13}NH_2$ | N-hexyl-1-methyl//carboxamide |
| 136 | 4 | $C_2H_5NH_2$ | N-ethyl-1-methyl//carboxamide |
| 137 | 5 | $CH_3NH_2$ | N,3-dimethyl-1-ethyl//carboxamide |
| 138 | 9 | $(CH_3)_2NH$ | 1-cyclopropyl-N,N-dimethyl-4-isopropyl//carboxamide |
| 139 | 11 | $(CH_3)_2NH$ | N,N,1,4-tetramethyl//acetamide |
| 140 | 12 | $CH_3NH_2$ | 1-ethyl-N-methyl//acetamide |
| 141 | 12 | $NH_3$ | 1-ethyl//acetamide |
| 142 | 12 | $(CH_3)_2NH$ | N,N-dimethyl-1-ethyl//acetamide |
| 143 | 12 | $n-C_{16}H_{13}NH_2$ | 1-ethyl-N-hexyl//acetamide |
| 144 | 12 | $(C_2H_5)_2NH$ | N,N,1-triethyl//acetamide |
| 145 | 13 | $CH_3NH_2$ | N-methyl-1-propyl//acetamide |
| 146 | 13 | $NH_3$ | 1-propyl//acetamide |
| 147 | 13 | $(CH_3)_2NH$ | N,N-dimethyl-1-propyl//acetamide, m.p. 159 – 162° C. |
| 148 | 13 | $n-C_6H_{13}NH_2$ | N-hexyl-1-propyl//acetamide |
| 149 | 13 | $(C_2H_5)_2NH$ | N,N-diethyl-1-propyl//acetamide |
| 150 | 14 | $CH_3NH_2$ | 1-isopropyl-N-methyl//acetamide |
| 151 | 14 | $NH_3$ | 1-isopropyl//acetamide |
| 152 | 14 | $(C_2H_5)_2NH$ | N,N-diethyl-1-isopropyl//acetamide |
| 153 | 15 | $CH_3NH_2$ | N,3-dimethyl-1-propyl//acetamide |
| 154 | 15 | $(CH_3)_2NH$ | 1-propyl-N,N,3-trimethyl//acetamide |
| 155 | 15 | $n-C_6H_{13}NH_2$ | n-hexyl-3-methyl-1-propyl//acetamide |
| 156 | 15 | $(C_2H_5)_2NH$ | N,N-diethyl-3-methyl-1-propyl//acetamide |
| 157 | 17 | $CH_3NH_2$ | N,α,1-trimethyl//acetamide |
| 158 | 17 | $NH_3$ | α,1-dimethyl//acetamide |
| 159 | 17 | $(CH_3)_2NH$ | N,N,α,1-tetramethyl//acetamide |
| 160 | 17 | $n-C_6H_{13}NH_2$ | α,1-dimethyl-N-hexyl//acetamide |
| 161 | 17 | $(C_2H_5)_2NH$ | N,N-diethyl-α,1-dimethyl//acetamide |
| 162 | 18 | $CH_3NH_2$ | 1-cyclohexyl-N,α,α-trimethyl//acetamide |
| 163 | 21 | $CH_3NH_2$ | N,8-dimethyl-1-propyl//acetamide |
| 164 | 25 | $NH_2$ | 6-benzyloxy-1-methyl//acetamide |
| 165 | 26 | $(CH_3)_2NH$ | 1-propyl-N,H,5-trimethyl//acetamide |
| 166 | 30 | $n-C_6H_{13}NH_2$ | 1-cyclopropyl-α,α-diethyl-3,3-dimethyl-6-ethoxy-N-hexyl//acetamide |
| 167 | 35 | $CH_3NH_2$ | 5-iodo-1-isopropyl-N-methyl//propionamide |
| 168 | 38 | $NH_2$ | 1-cyclobutyl-3-methyl-8-nitro-α-propyl//propionamide |
| 169 | 41 | $(CH_3)_2NH$ | N,N,α,α,β,3-hexamethyl-1,4,4-triethyl//propionamide |
| 170 | 44 | $(C_2H_5)_2NH$ | N,N-diethyl-1,3-dipropyl-5-methoxy-α-methyl//propionamide |
| 171 | 46 | $CH_3NH_2$ | N-methyl-β,1-dipropyl-3,3,5-triethyl//propionamide |
| 172 | 48 | $(CH_3)_2NH$ | N,N,1-trimethyl//butyramide |
| 173 | 48 | $CH_3NH_2$ | N,1-dimethyl//butyramide |
| 174 | 48 | $NH_2$ | 1-methyl//butyramide |
| 175 | 48 | $n-C_6H_{13}NH_2$ | N-hexyl-1-methyl//butyramide |
| 176 | 51 | $CH_3NH_2$ | 1-cyclobutyl-β,γ,γ,4-tetrapropyl-N,3,3-trimethyl//butyramide |
| 177 | 53 | $(CH_3)_2NH$ | N,N,α,α,β,β,γ,γ,4,5-decamethyl-1-ethyl//butyramide |
| 178 | 56 | $NH_2$ | 5-bromo-1-cyclopentyl-α,α,β-trimethyl//butyramide |
| 179 | 58 | $CH_3NH_2$ | 1,8-diethyl-N,α-dimethyl//butyramide |
| 180 | 60 | $(C_2H_5)_2NH$ | 1-propyl-N,N,α,γ-tetraethyl-3,3,5-trimethyl//butyramide |
| 181 | 62 | $n-C_6H_{13}NH_2$ | α,β-diethyl-3,3-dimethyl-1,5-dipropyl-N-hexyl//butyramide |

TABLE IV

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 182 | 2 | pyrrolidine | 1-[(1-methyl//propionyl]pyrrolidine |
| 183 | 2 | piperidine | 1-[(1-methyl//propionyl]piperidine |
| 184 | 2 | morpholine | 4-[(1-methyl//propionyl]morpholine |
| 185 | 2 | piperazine | 1-[(1-methyl//propionyl]piperazine |
| 186 | 2 | N-methyl-piperazine | 1-methyl-4-[1-methyl//propionyl]-piperazine |
| 187 | 2 | N-piperazine-ethanol | 1-(2-hydroxyethyl)-4-[(1-methyl//propionyl]piperazine |
| 188 | 4 | pyrrolidine | 1-[(1-methyl//carbonyl]pyrrolidine |
| 189 | 4 | morpholine | 4-[(1-methyl//carbonyl]morpholine |
| 190 | 5 | N-ethyl-piperazine | 1-ethyl-4-[(1-ethyl-3-methyl//carbonyl]piperazine |
| 191 | 11 | piperidine | 1-[(1,4-dimethyl//acetyl]-piperidine |
| 192 | 12 | morpholine | 4-[(1-ethyl//acetyl]morpholine |
| 193 | 12 | N-piperazine-propanol | 1-(3-hydroxypropyl)-4-[(1-ethyl//acetyl]piperazine |
| 194 | 13 | pyrrolidine | 1-[(1-propyl//acetyl]pyrrolidine |
| 195 | 13 | morpholine | 4-[(1-propyl//acetyl]morpholine |
| 196 | 14 | piperidine | 1-[(1-isopropyl//acetyl]piperidine |
| 197 | 15 | piperazine | 1-[(3-methyl-1-propyl//acetyl]-piperazine |
| 198 | 17 | N-ethyl-piperazine | 1-ethyl-4-[(α,1-dimethyl//acetyl]-piperazine |
| 199 | 25 | pyrrolidine | 1-[(6-benzyloxy-1-methyl//acetyl]-pyrrolidine |
| 200 | 26 | piperidine | 1-[(5-methyl-1-propyl//acetyl]piperidine |
| 201 | 30 | morpholine | 4-[(1-cyclopropyl-α,α-diethyl-3,3-dimethyl-6-ethoxy//acetyl]-morpholine |
| 202 | 36 | piperazine | 1-[8-acetoxy-1-ethyl-α,3,3,4,4-pentamethyl//propionyl]piperazine |
| 203 | 39 | N-piperazine-ethanol | 1-(2-hydroxyethyl)-4-[(1-cyclopropyl-α,α,β,β,4,6-hexamethyl//propionyl]piperazine |
| 204 | 40 | pyrrolidine | 1-[(1,3-dimethyl-α,α-dipropyl//propionyl]pyrrolidine |
| 205 | 42 | morpholine | 4-[(1-ethyl-β,β,4,4-tetramethyl//propionyl]morpholine |
| 206 | 47 | N-propyl-piperazine | 1-propyl-4-[(1-cyclopropyl-α,β-diethyl-6-ethoxy//propionyl]-piperazine |
| 207 | 48 | pyrrolidine | 1-[(1-methyl//butyryl]pyrrolidine |
| 207a | 48 | N-piperazine-methanol | 1-(hydroxymethyl)-4-[(1-methyl//butyryl]piperazine |
| 208 | 50 | piperidine | 1-[γ,γ-diethyl-3,3-dimethyl-1-propyl//butyryl]piperidine |
| 209 | 52 | morpholine | 4-[(7-chloro-α,β,β,γ,γ,4,4-heptaethyl-1-methyl//butyryl]-morpholine |
| 210 | 59 | piperazine | 1-[(1-butyl-6-fluoro-α,β,γ,3,3,4-hexamethyl//butyryl]piperazine |

TABLE V

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]-INDOLE-1-(SUFFIX LISTED BELOW)] PREFIX//SUFFIX |
|---|---|---|---|
| 211 | 3 | $CH_3NH_2$ | N,1-dimethyl//acetamide |
| 212 | 3 | $NH_3$ | 1-methyl//acetamide |
| 213 | 3 | $n-C_6H_{13}NH_2$ | N-hexyl-1-methyl//acetamide |
| 214 | 3 | $(CH_3)_2NH$ | N,N,1-trimethyl//acetamide, m.p. 182° C. |
| 215 | 3 | $(C_2H_5)_2NH$ | N,N-diethyl-1-methyl//acetamide |
| 216 | 96 | $CH_3NH_2$ | N,1-dimethyl//propionamide |
| 217 | 96 | $NH_3$ | 1-methyl//propionamide |
| 218 | 96 | $(CH_3)_2NH$ | N,N,1-trimethyl//propionamide |
| 219 | 96 | $n-C_6H_{13}NH_2$ | N-hexyl-1-methyl//propionamide |
| 220 | 96 | $(C_2H_5)_2NH$ | N,N-diethyl-1-methyl//propionamide |
| 221 | 65 | $CH_3NH_2$ | N,1-dimethyl//carboxamide |
| 222 | 65 | $NH_3$ | 1-methyl//carboxamide |
| 223 | 65 | $(CH_3)_2NH$ | N,N,1-trimethyl//carboxamide |
| 224 | 65 | $n-C_6H_{13}NH_2$ | N-hexyl-1-methyl//carboxamide |
| 225 | 65 | $(C_2H_5)_2NH$ | N,N-diethyl-1-methyl//carboxamide |
| 226 | 66 | $CH_3NH_2$ | N,3-dimethyl-1-ethyl//carboxamide |
| 227 | 69 | $NH_3$ | 8-ethyl-propyl//carboxamide |
| 228 | 70 | $(CH_3)_2NH$ | 1-cyclopropyl-N,N-dimethyl-4-isopropyl//carboxamide |
| 229 | 72 | $(CH_3)_2NH$ | N,N,1,4-tetramethyl//acetamide |
| 230 | 73 | $CH_3NH_2$ | 1-ethyl-N-methyl//acetamide |
| 231 | 73 | $NH_3$ | 1-ethyl//acetamide |
| 232 | 73 | $(CH_3)_2NH$ | N,N-dimethyl-1-ethyl//acetamide |
| 233 | 73 | $n-C_{16}H_{13}NH_2$ | 1-ethyl-N-hexyl//acetamide |

TABLE V-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO-[3,4-b]-INDOLE-1-(SUFFIX LISTED BELOW)] PREFIX//SUFFIX |
|---|---|---|---|
| 234 | 73 | $(C_2H_5)_2NH$ | N,N,1-triethyl//acetamide |
| 235 | 74 | $CH_3NH_2$ | N-methyl-1-propyl//acetamide |
| 236 | 74 | $NH_3$ | 1-propyl//acetamide |
| 237 | 74 | $(CH_3)_2NH$ | N,N-dimethyl-1-propyl//acetamide |
| 238 | 74 | $n-C_6H_{13}NH_2$ | N-hexyl-1-propyl//acetamide |
| 239 | 74 | $(C_2H_5)_2NH$ | N,N-diethyl-1-propyl//acetamide |
| 240 | 75 | $CH_3NH_2$ | 1-isopropyl-N-methyl//acetamide |
| 241 | 75 | $NH_3$ | 1-isopropyl//acetamide |
| 242 | 75 | $(C_2H_5)_2NH$ | N,N-diethyl-1-isopropyl//acetamide |
| 243 | 76 | $CH_3NH_2$ | N,3-dimethyl-1-propyl//acetamide |
| 244 | 76 | $NH_3$ | 3-methyl-1-propyl//acetamide |
| 245 | 76 | $(CH_3)_2NH$ | 1-propyl-N,N,3-trimethyl//acetamide |
| 246 | 76 | $n-C_6H_{13}NH_2$ | N-hexyl-3-methyl-1-propyl//acetamide |
| 247 | 76 | $(C_2H_5)_2NH$ | N,N-diethyl-3-methyl-1-propyl//acetamide |
| 248 | 78 | $CH_3NH_2$ | N,α,1-trimethyl//acetamide |
| 249 | 78 | $NH_3$ | α,1-dimethyl//acetamide |
| 250 | 78 | $(CH_3)_2NH$ | N,N,α,1-tetramethyl//acetamide |
| 251 | 78 | $n-C_6H_{13}NH_2$ | α,1-dimethyl-N-hexyl//acetamide |
| 252 | 78 | $(C_2H_5)_2NH$ | N,N-diethyl-α,1-dimethyl//acetamide |
| 253 | 79 | $CH_3NH_2$ | 1-cyclohexyl-N,α,α-trimethyl//acetamide |
| 254 | 82 | $CH_3NH_2$ | N,8-dimethyl-1-propyl//acetamide |
| 255 | 83 | $NH_2$ | 6-bromo-1-propyl//acetamide |
| 256 | 89 | $(CH_3)_2NH$ | α,α-diethyl-8-fluoro-N,N,1-trimethyl//acetamide |
| 257 | 91 | $n-C_6H_{13}NH_2$ | 1-cyclopropyl-α,α-diethyl-3,3-dimethyl-6-ethoxy-N-hexyl//acetamide |
| 258 | 99 | $NH_2$ | 1-cyclobutyl-3-methyl-8-nitro-α-propyl//propionamide |
| 259 | 102 | $(CH_3)_2NH$ | N,N,α,α,β,3-hexamethyl-1,4,4-triethyl//propionamide |
| 260 | 105 | $(C_2H_5)_2NH$ | N,N-diethyl-1,3-dipropyl-5-methoxy-α-methyl//propionamide |
| 261 | 107 | $CH_3NH_2$ | β,1-dipropyl-N-methyl-3,3,5-triethyl//propionamide |
| 262 | 108 | $CH_3NH_2$ | 1-cyclopropyl-α,β-diethyl-6-ethoxy-N-methyl//propionamide |
| 263 | 109 | $(CH_3)_2NH$ | N,N,1-trimethyl//butyramide |
| 264 | 109 | $CH_3NH_2$ | N,1-dimethyl//butyramido |
| 265 | 109 | $n-C_6H_{13}NH_2$ | N-hexyl-1-methyl//butyramide |
| 266 | 112 | $CH_3NH_2$ | 1-cyclobutyl-β,γ,γ,4-tetrapropyl-N,3,3-trimethyl//butyramide |
| 267 | 113 | $(CH_3)_2NH$ | 7-chloro-α,β,β,γ,γ,4,4-heptaethyl-N,N,1-trimethyl//butyramide |
| 268 | 117 | $NH_2$ | 5-bromo-1-cyclopentyl-α,α,β-trimethyl//butyramide |
| 269 | 119 | $CH_3NH_2$ | 1,8-diethyl-N,α-dimethyl//butyramide |
| 270 | 121 | $(C_2H_5)_2NH$ | 1-propyl-N,N,α,γ-tetraethyl-3,3,5-trimethyl//butyramide |
| 271 | 123 | $n-C_6H_{13}NH_2$ | α,β-diethyl-3,3-dimethyl-1,5-dipropyl-N-hexyl//butyramide |

TABLE VI

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROXYTHIOPYRANO-[3,4-b]INDOLE-1-(SUFFIX LISTED BELOW)] PREFIX//SUFFIX |
|---|---|---|---|
| 272 | 3 | pyrrolidine | 1-[(1-methyl//acetyl]pyrrolidine |
| 273 | 3 | piperidine | 1-[(1-methyl//acetyl]piperidine |
| 274 | 3 | morpholine | 4-[(1-methyl//acetyl]morpholine |
| 275 | 3 | piperazine | 1-[(1-methyl//acetyl]piperazine |
| 276 | 3 | N-methyl-piperazine | 1-methyl-4-[1-methyl//acetyl]-piperazine |
| 277 | 3 | N-piperazine-ethanol | 1-(2-hydroxyethyl)-4-[(1-methyl//acetyl]piperazine |
| 278 | 96 | pyrrolidine | 1-[(1-methyl//propionyl]-pyrrolidine |
| 279 | 96 | piperidine | 1-[(1-methyl//propionyl]piperidine |
| 280 | 96 | morpholine | 4-[(1-methyl//propionyl]morpholine |
| 281 | 96 | piperazine | 1-[(1-methyl//propionyl]piperazine |
| 282 | 96 | N-methyl-piperazine | 1-methyl-4-[1-methyl//propionyl]-piperazine |
| 283 | 96 | N-piperazine-ethanol | 1-(2-hydroxyethyl)-4-[(1-methyl//propionyl]piperazine |
| 284 | 65 | pyrrolidine | 1-[(1-methyl//carbonyl]pyrrolidine |
| 285 | 65 | morpholine | 4-[(1-methyl//carbonyl]morpholine |
| 286 | 66 | N-ethyl-piperazine | 1-ethyl-4-[(1-ethyl-3-methyl//carbonyl]piperzine |

TABLE VI-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROXYTHIOPYRANO-[3,4-b]INDOLE-1-(SUFFIX LISTED BELOW)] PREFIX//SUFFIX |
|---|---|---|---|
| 287 | 72 | piperidine | 1-[(1,4-dimethyl//acetyl]-piperidine |
| 288 | 73 | morpholine | 4-[(1-ethyl//acetyl]morpholine |
| 289 | 73 | N-piperazine-propanol | 1-(3-hydroxypropyl)-4-[(1-ethyl//acetyl]piperazine |
| 290 | 74 | pyrrolidine | 1-[(1-propyl//acetyl//acetyl]pyrrolidine |
| 291 | 74 | morpholine | 4-[(1-propyl//acetyl]morpholine |
| 292 | 75 | piperdine | 1-[(1-isopropyl//acetyl]piperidine |
| 293 | 76 | piperazine | 1-[(3-methyl-1-propyl//acetyl]-piperazine |
| 294 | 78 | N-ethyl-piperazine | 1-ethyl-4-[(α,1-dimethyl//acetyl]-piperazine |
| 295 | 78 | N-methyl-piperazine | 1-methyl-4-[(α,1-dimethyl//acetyl)]-piperazine |
| 296 | 86 | pyrrolidine | 1-[(6-benzyloxyl-1-methyl//acetyl]pyrrolidine |
| 297 | 87 | piperidine | 1-[(5-methyl-1-propyl//acetyl]-piperidine |
| 298 | 91 | morpholine | 4-[(1-cyclopropyl-α,α-diethyl-3,3-dimethyl-6-ethoxy//acetyl]-morpholine |
| 299 | 97 | piperazine | 1-[(8-acetoxy-1-ethyl-α,3,3,4,4-pentamethyl//propionyl]piperazine |
| 300 | 100 | N-piperazine-ethanol | 1-(2-hydroxyethyl)-4-[(1-cyclopropyl-α,α,β,β,4,6-hexamethyl//propionyl]piperazine |
| 301 | 101 | pyrrolidine | 1-[(1,3-dimethyl-α,α-dipropyl//propionyl]pyrrolidine |
| 302 | 103 | morpholine | 4-[(1-ethyl-β,β,4,4-tetramethyl//propionyl]morpholine |
| 303 | 108 | N-propyl-piperazine | 1-propyl-4-[(1-cyclopropyl-α,β-diethyl-6-ethoxy//propionyl]-piperazine |
| 304 | 109 | pyrrolidine | 1-[(1-methyl//butyryl]pyrrolidine |
| 305 | 109 | N-piperazine-methanol | 1-(hydroxymethyl)-4-[(1-methyl//butyryl]piperazine |
| 306 | 111 | piperidine | 1-[(γ,γ-diethyl-3,3-dimethyl-1-propyl//butyryl]piperidine |
| 307 | 113 | morpholine | 4-[(7-chloro-α,β,β,γ,γ,4,4-heptaethyl-1-methyl//butyryl]-morpholine |
| 308 | 120 | piperazine | 1-[(1-butyl-6-fluoro-α,β,γ,3,3,4-hexamethyl//butyryl]piperazine |

EXAMPLE 309

1-[2-(Dimethylamino)ethyl]-1-methyl-1,3,4,9-tetrahydropyrano[3,4-b]indole [I; $R^1 = CH_3$, $R^2$, $R^3$, $R^4$, $R^5$, $R^6$ and $R^7 = H$, $X = O$ and $Y = CH_2CH_2N(CH_3)_2$]

A solution of N,N,1-trimethyl-1,3,4,9-tetrahydropyrano-[3,4-b]indole-1-acetamide (5.0 g, 0.018 mole), prepared as described in Example 126, is added dropwise to a cooled, well-stirred mixture of lithium aluminum hydride (1.4 g, 0.036 mole) in 200 ml of ether. Stirring is continued for one hour at room temperature, then the mixture is heated under reflux for 2 hr.

After cooling in an ice-water bath, 6.2 ml of water is added dropwise to destroy the excess hydride. Then 100 ml more of water is added and the ether phase decanted. The aqueous phase is extracted once with benzene. The combined organic phases are washed with water, dried over sodium sulfate, and evaporated to dryness to afford 5 g of oil which crystallized on standing. The crystallized product is recrystallized from ether to afford the pure title comound, m.p. 133° – 135° C., nmr(CDCl$_3$)δ1.53 (s, 3H), 2.07 (2H), 9.74 (1H), 10.55 (6H).

The corresponding oxalic acid addition salt (oxalate), 1-](2-dimethylamino)ethyl]-1-methyl-1,3,4,9-tetrahydropyrano-[3,4-b]indole oxalate, has m.p. 181° – 183° C. after crystallization from methanol-ether.

In the same manner but replacing lithium aluminum hydride with an equivalent amount of lithium aluminum hydride-aluminum chloride, aluminum hydride-aluminum chloride, diborane and sodium borohydride-aluminum chloride, the title compound is also obtained.

In the same manner but replacing N,N,1-trimethyl-1,3,4,9-tetrahydropyrano[3,4-b]indole-1-acetamide with an equivalent amount of the following amides described in Example 126, 1-methyl-1,3,4,9-tetrahydropyrano[3,4-b]indole-1-acetamide, N,1-dimethyl-1,3,4,9-tetrahydropyrano[3,4-b]indole-1-acetamide, N-hexyl-1-methyl-1,3,4,9-tetrahydropyrano[3,4-b]indole-1-acetamide, N,N-diethyl-1-methyl-1,3,4,9-tetrahydropyrano[3,4-b]indole-1-acetamide, N-isopropyl-1-methyl-1,3,4,9-tetrahydropyrano[3,4-b]indole-1-acetamide, N-ethyl-1-methyl-1,3,4,9-tetrahydropyrano[3,4-b]indole-1-acetamide, 1-[(1-methyl-1,3,4,9-tetrahydropyrano[3,4-b]indol-1-yl)acetyl]-pyrrolidine, 1-[(1-methyl-1,3,4,9-tetrahydropyrano[3,4-b]indol-1-yl)acetyl]-piperidine, 1-[(1-methyl-1,3,4,9-tetrahydropyrano[3,4-b]indol-1-yl)acetyl]-morpholine, and 1-methyl-4-[(1-methyl-1,3,4,9-tetrahydropyrano[3,4-b]indol-1-yl)acetyl]piperazine, then there are obtained, 1-(2-aminoethyl)-1-methyl-1,3,4,9-tetrahydropyrano[3,4-b]indole, m.p. 80° – 84° C., $\nu_{max}^{CHCl_3}$ 3455, 3280cm$^{-1}$, 1-methyl-1-[2-(methylamino)ethyl]-1,3,4,9-tetrahydropyrano[3,4-b]indole, m.p. 160° – 163° C., (m.p. of corresponding oxalic acid addition salt, 140° – 144° C.), 1-[2-(hexylamino)ethyl]-1-methyl-1,3,4,9-tetrahydropyrano[3,4-b]indole, 1-[2-(diethylamino)ethyl]-1-methyl-1,3,4,9-tetrahydropyrano[3,4-b]indole, m.p. 74°–76° C, m.p. of corresponding maleic acid addition salt, 98°–100° C., 1-[2-(isopropylamino)ethyl]-1-methyl-1,3,4,9-tetrahydropyrano[3,4-b]indole, 1-[2-(ethylamino)ethyl]-1-methyl-1,3,4,9-tetrahydropyrano[3,4-b]indole, 1-methyl-1-[2-(1-pyrrolidinyl)ethyl]-1,3,4,9-tetrahydropyrano[3,4-b]indole,
nmr (CDCl$_3$) δ1.62 (3H), 2.00 (m, 4H), 4.05 (m, 2H), m.p. of corresponding maleic acid addition salt (maleate), 192° – 193° C., 1-methyl-1-(2-piperidinoethyl)-1,3,4,9-tetrahydropyrano[3,4-b]indole, m.p. 146° – 148° C., m.p. of corresponding maleic acid addition salt, 147° – 149° C., 1-methyl-1-(2-morpholinoethyl)-1,3,4,9-tetrahydropyrano[3,4-b]indole, nmr (DMSO-d$_6$) δ1.50 (3H), 6.07 (2H), 6.87 – 7.65 (m, 4H), 10.86 (1H), m.p. of corresponding maleic acid addition salt, 192° – 193° C., and 1-methyl-1-[2-(4-methyl-1-piperazinyl)ethyl]-1,3,4,9-tetrahydropyrano[3,4-b]indole, nmr (CDCl$_3$) δ1.47 (3H), 2.58 (3H), 3.87 (t, 2H), [m.p. of corresponding maleic acid addition salt (i.e. dimaleate), 208° – 210° C.], respectively.

By following the procedure of Example 309 but using as starting material an equivalent amount of one of the amido compounds of formula VII, described in Examples 127 to 308 instead of N,N,1-trimethyl-1,3,4,9-tetrahydropyrano[3,4-b]indole-1-acetamide, then the corresponding compounds of formula I in which $R^7$ is hydrogen are obtained. Examples of such compounds of formula I are listed as products in Tables VII and VIII together with the appropriate starting material, amides of formula VII. In each case the starting material is noted by the example in which it is prepared.

TABLE VII

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]-INDOLE |
|---|---|---|
| 310 | 127 | 1-methyl-1-[3-(methylamino)propyl], nmr (CDCl$_3$) δ1.48 (3H), 1.87 (4H), 2.47 (3H), corresponding oxalic acid addition salt has m.p. 110° C. |
| 311 | 128 | 1-(3-aminopropyl)-1-methyl |
| 312 | 129 | 1-methyl-1-[3-(dimethylamino)propyl], m.p. 114 – 116° C., corresponding oxalic acid addition salt has m.p. 168 – 172° C. |
| 313 | 130 | 1-[3-(hexylamino)propyl]-1-methyl |
| 314 | 131 | 1-[3-(diethylamino)propyl]-1-methyl |
| 315 | 132 | 1-methyl-1-[(methylamino)methyl] |
| 316 | 133 | 1-(aminomethyl)-1-methyl, $\gamma_{max}^{CHCl_3}$ 3465, 3400, 3180, 2930, corresponding hydrochloric acid addition salt (hydrochloride) has m.p. 251 – 252°C. |
| 317 | 134 | 1-[(dimethylamino)methyl]-1-methyl |
| 318 | 135 | 1-[(hexylamino)methyl]-1-methyl |
| 319 | 136 | 1-[(ethylamino)methyl]-1-methyl, nmr (DMSO-d$_6$) δ1.18 (3H), 1.62 (3H), 2.80 (2H); corresponding hydrochloride acid addition salt has m.p. 245 – 243°C. |
| 320 | 137 | 1-ethyl-3-methyl-1-[(methylamino)methyl] |
| 321 | 138 | 1-cyclopropyl-1-[(dimethylamino)methyl]-4-isopropyl |
| 322 | 139 | 1,4-dimethyl-1-[2-(dimethylamino)ethyl] |
| 323 | 140 | 1-ethyl-1-[2-(methylamino)ethyl] |
| 324 | 141 | 1-(2-aminoethyl)-1-ethyl |
| 325 | 142 | 1-[2-(dimethylamino)ethyl]-1-ethyl |
| 326 | 143 | 1-ethyl-1-[2-(hexylamino)ethyl] |
| 327 | 144 | 1-[2-(diethylamino)ethyl]-1-ethyl |
| 328 | 145 | 1-[2-(methylamino)ethyl]-1-propyl |
| 329 | 146 | 1-(aminoethyl)-1-propyl |
| 330 | 147 | 1-[2-(dimethylamino)ethyl]-1-propyl, nmr (CDCl$_3$) 0.84 (t,3H), 1.21 (3, 6H), 2.79 (t, 5 = 5.5 cps, 2H) corresponding maleic acid addition salt has m.p. 152 – 154° C) |
| 331 | 148 | 1-[2-(hexylamino)ethyl]-1-propyl |
| 332 | 149 | 1-[2-(diethylamino)ethyl]-1-propyl |
| 333 | 150 | 1-isopropyl-1-[2-(methylamino)ethyl] |
| 334 | 151 | 1-(2-aminoethyl)-1-isopropyl |
| 335 | 152 | 1-[2-(diethylamino)ethyl]-1-isopropyl |
| 336 | 153 | 3-methyl-1-[2-(methylamino)ethyl]-1-propyl |
| 337 | 154 | 1-[2-(dimethylamino)ethyl]-3-methyl-1-propyl |
| 338 | 155 | 1-[2-(hexylamino)ethyl]-3-methyl- |

TABLE VII-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]-INDOLE |
|---|---|---|
| | | 1-propyl |
| 339 | 156 | 1-[2-(diethylamino)ethyl]-3-methyl-1-propyl |
| 340 | 157 | 1-[1-methyl-2-(methylamino)ethyl]-1-methyl |
| 341 | 158 | 1-(2-amino-1-methyl-ethyl)-1-methyl |
| 342 | 159 | 1-[2-(dimethylamino)-1-methyl-ethyl]-1-methyl |
| 343 | 160 | 1-[2-(hexylamino)-1-methyl-ethyl]-1-methyl |
| 344 | 161 | 1-[2-(diethylamino)-1-methyl-ethyl]-1-methyl |
| 345 | 162 | 1-cyclohexyl-1-[1,1-dimethyl-2-(methylamino)ethyl] |
| 346 | 163 | 8-methyl-1-[2-(methylamino)ethyl]-1-propyl |
| 347 | 164 | 1-(2-aminoethyl)-6-benzyloxy-1-methyl |
| 348 | 165 | 1-[2-(dimethylamino)ethyl]-5-methyl-1-propyl |
| 349 | 166 | 1-cyclopropyl-1-[1,1-diethyl-2-(hexylamino)ethyl]-3,3-dimethyl-6-ethoxy |
| 350 | 167 | 5-iodo-1-isopropyl-1-[3-(methyl-amino)propyl] |
| 351 | 168 | 1-(3-amino-2-propyl-propyl)-1-cyclobutyl-3-methyl-8-nitro |
| 352 | 169 | 1-[3-(dimethylamino)-1,2,2-trimethyl-propyl]-1,4,4-triethyl |
| 353 | 170 | 1-[3-(diethylamino)-2-methyl-propyl]-1,3-dipropyl-5-methoxy |
| 354 | 171 | 1-[1-propyl-3-(methylamino)-propyl]-1-propyl-3,3,5-trimethyl |
| 355 | 172 | 1-[4-(dimethylamino)butyl]-1-methyl |
| 356 | 173 | 1-[4-(methylamino)butyl]-1-methyl |
| 357 | 174 | 1-(4-aminobutyl)-1-methyl |
| 358 | 175 | 1-[4-(hexylamino)butyl]-1-methyl |
| 359 | 176 | 1-cyclobutyl-3,3-dimethyl-1-[4-(methylamino)-1,1,2-tripropyl-butyl]-4-propyl |
| 360 | 177 | 4,5-dimethyl-1-ethyl-1-[4-dimethylamino)-1,1,2,2,3,3-hexamethylbutyl] |
| 361 | 178 | 1-(4-amino-2,3,3-trimethyl-butyl)-5-bromo-1-cyclopentyl |
| 362 | 179 | 1,8-diethyl-1-[3-methyl-4-(methylamino)butyl] |
| 363 | 180 | 1-[1,3-diethyl-4-(diethylamino)-butyl]-1-propyl-3,3,5-trimethyl |
| 364 | 181 | 1-[2,3-diethyl-4-(hexylamino)-butyl]-3,3-dimethyl-1,5-dipropyl |
| 365 | 182 | 1-methyl-1-[3-(1-pyrrolidinyl)-propyl], m.p. 124 – 127° C. |
| 366 | 183 | 1-methyl-1-(3-piperidinopropyl) |
| 367 | 184 | 1-methyl-1-(3-morpholinopropyl) |
| 368 | 185 | 1-methyl-1-(3-piperazinopropyl) |
| 369 | 186 | 1-methyl-1-[3-(4-methyl-1-piperazinyl)propyl] |
| 370 | 187 | 1-{3-[4-(2-hydroxyethyl)-1-piperazinyl]propyl}-1-methyl |
| 371 | 188 | 1-methyl-1-[(1-pyrrolidinyl)-methyl] |
| 372 | 189 | 1-methyl-1-(morpholinomethyl) |
| 373 | 190 | 1-ethyl-3-methyl-1-[(4-methyl-1-piperazinyl)methyl] |
| 374 | 191 | 1,4-dimethyl-1-(2-piperidinoethyl) |
| 375 | 192 | 1-ethyl-1-(2-morpholinoethyl) |
| 376 | 193 | 1-ethyl-1-{2-[4-(3-hydroxypropyl)-1-piperazinyl]ethyl} |
| 377 | 194 | 1-propyl-1-[2-(1-pyrrolidinyl)-ethyl] |
| 378 | 195 | 1-propyl-1-(2-morpholinoethyl) |
| 379 | 196 | 1-isopropyl-1-(2-piperidinoethyl) |
| 380 | 197 | 3-methyl-1-(2-piperazinoethyl)-1-propyl |
| 381 | 198 | 1-ethyl-1-[1-methyl-2-(4-methyl-1-piperazinyl)ethyl] |
| 382 | 199 | 6-benzyloxy-1-methyl-1-[2-(1-pyrrolidinyl)ethyl] |
| 383 | 200 | 5-methyl-1-(2-piperidinoethyl)-1-propyl |
| 384 | 201 | 1-cyclopropyl-1-(1,1-diethyl-2-morpholinoethyl)-3,3-dimethyl-6-ethoxy |
| 385 | 202 | 8-acetoxy-1-ethyl-3,3,4,4-tetramethyl-1-(2-methyl-3-piperazinopropyl) |
| 386 | 203 | 1-cyclopropyl-4,6-dimethyl-1- |

TABLE VII-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]-INDOLE |
|---|---|---|
| 387 | 204 | {3-[4-(2-hydroxyethyl)-1-piperazinoyl]1,1,2,2-tetramethylpropyl} 1,3-dimethyl-1-[2,2-dipropyl-3-(1-pyrrolidinyl)propyl] |
| 388 | 205 | 4,4-dimethyl-1-ethyl-1-(1,1-dimethyl-3-morpholinopropyl) |
| 389 | 206 | 1-cyclopropyl-1-[1,2-diethyl-3-(4-propyl-1-piperazinyl)propyl]-6-ethoxy |
| 390 | 207 | 1-methyl-1-[4-(1-pyrrolidinyl)-butyl] |
| 391 | 207a | 1-{4-[4-(hydroxymethyl)-1-piperazinyl]butyl}-1-methyl |
| 392 | 208 | 1-[(1,1-diethyl-4-piperidino)butyl]-3,3-dimethyl-1-propyl |
| 393 | 209 | 7-chloro-4,4-diethyl-1-methyl-1-(4-morpholino-1,1,2,2,3-pentaethylbutyl) |
| 394 | 210 | 1-butyl-6-fluoro-1-(4-piperazino-1,2,3-trimethylbutyl)-3,3,4-trimethyl |

TABLE VIII

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO-[3,4-b]INDOLE |
|---|---|---|
| 395 | 211 | 1-methyl-1-[2-(methylamino)ethyl] |
| 396 | 212 | 1-(2-aminoethyl)-1-methyl |
| 397 | 213 | 1-[(2-hexylamino)ethyl]-1-methyl |
| 398 | 214 | 1-[2-(dimethylamino)ethyl]-1-methyl, m.p. 119 – 121° C. |
| 399 | 215 | 1-[2-(diethylamino)ethyl]-1-methyl |
| 400 | 216 | 1-methyl-1-[3-(methylamino)propyl] |
| 401 | 217 | 1-(3-aminopropyl)-1-methyl |
| 402 | 218 | 1-[3-(dimethylamino)propyl]-1-methyl |
| 403 | 219 | 1-[3-(hexylamino)propyl]-1-methyl |
| 404 | 220 | 1-[3-(diethylamino)propyl]-1-methyl |
| 405 | 221 | 1-methyl-1-[(methylamino)methyl] |
| 406 | 222 | 1-(aminomethyl)-1-methyl |
| 407 | 223 | 1-[(dimethylamino)methyl]-1-methyl |
| 408 | 224 | 1-[(hexylamino)methyl[-1-methyl |
| 409 | 225 | 1-[(diethylamino)methyl]-1-methyl |
| 410 | 226 | 1-ethyl-3-methyl-1-[(methylamino)-methyl] |
| 411 | 228 | 1-cyclopropyl-1-[(dimethylamino)-methyl]-4-isopropyl |
| 412 | 229 | 1,4-dimethyl-1-[2-(dimethylamino)-ethyl] |
| 413 | 230 | 1-ethyl-1-[2-(methylamino)ethyl] |
| 414 | 231 | 1-(2-aminoethyl)-1-ethyl |
| 415 | 232 | 1-[2-(dimethylamino)ethyl]-1-ethyl |
| 416 | 233 | 1-ethyl-1-[2-(hexylamino)ethyl] |
| 417 | 234 | 1-[2-(diethylamino)ethyl]-1-ethyl |
| 418 | 235 | 1-[2-(methylamino)ethyl]-1-propyl |
| 419 | 236 | 1-(aminoethyl)-1-propyl |
| 420 | 237 | 1-[2-(dimethylamino)ethyl]-1-propyl |
| 421 | 238 | 1-[2-(hexylamino)ethyl]-1-propyl |
| 422 | 239 | 1-[2-(diethylamino)ethyl]-1-propyl |
| 423 | 240 | 1-isopropyl-1-[2-(methylamino)-ethyl] |
| 424 | 241 | 1-(2-aminoethyl)-1-isopropyl |
| 425 | 242 | 1-[2-(diethylamino)ethyl]-1-isopropyl |
| 426 | 243 | 3-methyl-1-[2-(methylamino)ethyl]-1-propyl |
| 427 | 245 | 1-[2-(dimethylamino)ethyl]-3-methyl-1-propyl |
| 428 | 246 | 1-[2-(hexylamino)ethyl]-3-methyl-1-propyl |
| 429 | 247 | 1-[2-(diethylamino)ethyl]-3-methyl-1-propyl |
| 430 | 248 | 1-[1-methyl-2-(methylamino)ethyl]-1-methyl |
| 431 | 249 | 1-(2-amino-1-methylethyl)-1-methyl |
| 432 | 250 | 1-[2-(dimethylamino)-1-methylethyl]-1-methyl |
| 433 | 251 | 1-[2-(hexylamino)-1-methyl-ethyl]-1-methyl |

TABLE VIII-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO-[3,4-b]INDOLE |
|---|---|---|
| 482 | 303 | dimethyl-3-morpholinopropyl) 1-cyclopropyl-6-ethoxy-1-[1,2-diethyl-3-(4-propyl-1-piperazinyl)propyl] |
| 483 | 304 | 1-methyl-1-[4-(1-pyrrolidinyl)-butyl] |
| 484 | 305 | 1-{4-[4-(hydroxymethyl)-piperazinyl]butyl}-1-methyl |
| 485 | 306 | 1-[(1,1-diethyl-4-piperidino)-butyl]-3,3-dimethyl-1-propyl |
| 486 | 307 | 7-chloro-4,4-diethyl-1-methyl-1-(4-morpholino-1,1,2,2,3-pentaethylbutyl) |
| 487 | 308 | 1-butyl-6-fluoro-1-(4-piperazino-1,2,3-trimethylbutyl)-3,3,4-trimethyl |

EXAMPLE 488

1,9-Dimethyl-1,3,4,9-tetrahydropyrano[3,4-b]indole-1-acetic acid (VII; $R^1$ and $R^7$ = $CH_3$, $R^2$, $R^3$, $R^4$, $R^5$ and $R^6$ = H, X = O and Z = $CH_2COOH$ 1-Methyl-1,3,4,9-tetrahydropyrano[3,4-b]indole-1-acetic acid (10 g., 0.04 mole), prepared as described in Example 1, in 150 ml. of tetrahydrofuran is added dropwise to a stirred suspension of sodium hydride (4.4 g. of 55% dispersion) in 200 ml. of tetrahydrofuran. This mixture is heated at 50° C. with stirring for 2 hr. Methyl iodide (14.2 g. 0.1 mole) is added dropwise and heating and stirring is continued for a further 2 hr.

After cooling, water is added until the solution is clear. The tetrahydrofuran is evaporated off under reduced pressure, the residue is partitioned between water and benzene. The aqueous phase is washed once with benzene, made acidic with HCl, and extracted with benzene (3x). The organic phase is washed with water, dried over sodium sulfate and treated with charcoal. The organic layer is evaporated. The residue is crystallized from benzene and then ether-petroleum ether to afford the title compound, m.p. 105° - 108° C., nmr (CDCl$_3$) δ1.73 (S, 3H), 2.83 (t, J = 5.5, 2H), 3.0 (2H), 3.68 (3H), 4.08 (t, J = 5.5, 2H), 7.34 (4H), 9.47 (1H).

In the same manner but replacing methyl iodide with an equivalent amount of ethyl iodide, or propyl iodide, the N-ethyl analog of the title compound, 9-ethyl-1-methyl-1,3,4,9-tetrahydropyrano[3,4-b]indole-1-acetic acid, m.p. 134° - 136° C., and the N-propyl analog of the title compound, 1-methyl-9-propyl-1,3,4,9-tetrahydropyrano[3,4-b]indole-1-acetic acid, m.p. 120° - 122° C., are obtained, respectively.

By following the procedure of Example 488 but using as starting material an equivalent amount of the acid compounds of formula VII, in which $R^7$ is hydrogen, described in Examples 1 to 125, inclusive, instead of 1-methyl-1,3,4,9-tetrahydropyrano[3,4-b]indole-1-acetic acid, and using an equivalent amount of an appropriate organic halide, then the corresponding N-alkylated acid compounds of formula I are obtained. Examples of these latter compounds are listed as products in Tables IX and X together with the appropriate starting material of formula VII and organic halide used for their preparation. In each case the starting material is noted by the Example in which it is prepared.

TABLE IX

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROPYRANO[3,4-b]-INDOLE-(SUFFIX LISTED BELOW)] PREFIX//SUFFIX |
|---|---|---|---|
| 489 | 1 | $CH_2$=$CHCH_2Br$ | 9-allyl-1-methyl//acetic acid, m.p. 103–105° C. |
| 490 | 1 | $CH_2$=CHBr | 1-methyl-9-vinyl//acetic acid |
| 491 | 1 | CH≡$CCH_2Br$ | 1-methyl-9-propargyl//acetic acid |
| 492 | 2 | n-$C_3H_7I$ | 1-methyl-9-propyl//propionic acid |
| 493 | 2 | $CH_3I$ | 1,9-dimethyl//propionic acid |
| 494 | 2 | 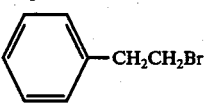 | 1-methyl-9-phenethyl//propionic acid |
| 495 | 2 | 1-(3-chloropropyl)-piperazine | 1-methyl-9-(3-piperidinopropyl)//propionic acid |
| 496 | 4 | 1-(2-chloroethyl)-pyrrolidine | 1-methyl-9-[2-(1-pyrrolidinyl)-ethyl]//carboxylic acid |
| 497 | 6 | CH≡$CCH_2Br$ | 1,3-diisopropyl-6-methyl-propargyl//carboxylic acid |
| 498 | 7 | $CH_3I$ | 6-hydroxy-1,3,3,9-tetramethyl//carboxylic acid |
| 499 | 8 | $CH_3CH$=CHBr | 8-ethyl-9-(1-propenyl)-1-propyl//carboxylic acid |
| 500 | 10 | $C_2H_5Br$ | 1-cyclopentyl-4,4,9-triethyl-3,3-dimethyl//carboxylic acid |
| 501 | 12 | $CH_3I$ | 1-ethyl-9-methyl//acetic acid |
| 502 | 12 | $C_2H_5Cl$ | 1,9-diethyl//acetic acid |
| 503 | 12 | $CH_2$=$CHCH_2Br$ | 9-allyl-1-ethyl//acetic acid |
| 504 | 12 | 2-(dimethylamino)-ethyl chloride | 9-[2-(dimethylamino)ethyl]//acetic acid |
| 505 | 13 | $CH_3I$ | 9-methyl-1-propyl//acetic acid |
| 506 | 13 | n-$C_3H_7Cl$ | 1,9-dipropyl//acetic acid |

TABLE VIII-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO-[3,4-b]INDOLE |
|---|---|---|
| 434 | 252 | 1-[2-(diethylamino)-1-methyl-ethyl]-1-methyl |
| 435 | 253 | 1-cyclohexyl-1-[1,1-dimethyl-2-(methylamino)ethyl] |
| 436 | 254 | 8-methyl-1-[2-(methylamino)ethyl]-1-propyl |
| 437 | 255 | 1-(2-aminoethyl)-6-bromo-1-propyl |
| 438 | 257 | 1-cyclopropyl-1-[1,1-diethyl-2-(hexylamino)ethyl]-3,3-dimethyl-6-ethoxy |
| 439 | 258 | 1-(3-amino-2-propyl-propyl)-1-cyclobutyl-3-methyl-8-nitro |
| 440 | 259 | 1-[3-(dimethylamino)-1,2,2-trimethyl-propyl]-1,4,4-triethyl |
| 441 | 260 | 1-[3-(diethylamino)-2-methyl-propyl]1,3-dipropyl-5-methoxy |
| 442 | 261 | 1-[1-propyl-3-(methylamino)-propyl]-1-propyl-3,3,5-trimethyl |
| 443 | 263 | 1-]4-(dimethylamino)butyl]-1-methyl |
| 444 | 264 | 1-[4-(methylamino)butyl]-1-methyl |
| 445 | 265 | 1-[4-(hexylamino)butyl]-1-methyl |
| 446 | 266 | 1-cyclobutyl-3,3-dimethyl-1-[4-(methylamino)-1,1,2-tripropyl-butyl]-4-propyl |
| 447 | 267 | 7-chloro-4,4-diethyl-1-]4-dimethylamino-1,1,2,2,3-pentaethylbutyl]-1-methyl |
| 448 | 268 | 1-(4-amino-2,3,3-trimethyl-butyl)-5-bromo-1-cyclopentyl |
| 449 | 269 | 1,8-diethyl-1-[3-methyl-4-(methylamino)butyl] |
| 450 | 270 | 1-[1,3-diethyl-4-(diethylamino)-butyl]-1-propyl-3,3,5-trimethyl |
| 451 | 271 | 1-[2,3-diethyl-4-(hexylamino)-butyl]-3,3-dimethyl-1,5-dipropyl |
| 452 | 272 | 1-methyl-1-[2-(1-pyrrolidinyl)-ethyl] |
| 453 | 273 | 1-methyl-1-(2-piperidinoethyl) |
| 454 | 274 | 1-methyl-1-(2-morpholinoethyl) |
| 455 | 275 | 1-methyl-1-(2-piperazinoethyl) |
| 456 | 276 | 1-methyl-1-[2-(4-methyl-1-piperazinyl)ethyl] |
| 457 | 277 | 1-{2-[4-(2-hydroxyethyl)-1-piperazinyl]ethyl}-1-methyl |
| 458 | 278 | 1-methyl-1-[3-(1-pyrrolidinyl)-propyl] |
| 459 | 279 | 1-methyl-1-(3-piperidinopropyl) |
| 460 | 280 | 1-methyl-1-(3-morpholinopropyl) |
| 461 | 281 | 1-methyl-1-(3-piperazinopropyl) |
| 462 | 282 | 1-methyl-1-[3-(4-methyl-1-piperazinyl)propyl] |
| 463 | 283 | 1-{3-[4-(2-hydroxyethyl)-1-piperazinyl]propyl}-1-methyl |
| 464 | 284 | 1-methyl-1-[(1-pyrrolidinyl)-methyl] |
| 465 | 285 | 1-methyl-1-(morpholinomethyl) |
| 466 | 286 | 1-ethyl-3-methyl-1-[(4-ethyl)-1-piperazinyl)methyl] |
| 467 | 287 | 1,4-dimethyl-1-(2-piperidino-ethyl) |
| 468 | 288 | 1-ethyl-1-(2-morpholinoethyl) |
| 469 | 289 | 1-ethyl-1-{2-[4-(3-hydroxy-propyl)-1-piperazinyl]ethyl} |
| 470 | 290 | 1-propyl-1-[2-(1-pyrrolidinyl)ethyl] |
| 471 | 291 | 1-(2-morpholinoethyl)-1-propyl |
| 472 | 292 | 1-isopropyl-1-(2-piperidinoethyl |
| 473 | 293 | 3-methyl-1-(2-piperazinoethyl)-1-propyl |
| 474 | 295 | 1-methyl-1-[1-methyl-2-(4-methyl-1-piperazinyl)ethyl] |
| 475 | 296 | 6-benzyloxy-1-methyl-1-[2-(1-pyrrolidinyl)ethyl] |
| 476 | 297 | 5-methyl-1-(2-piperidinoethyl)-1-propyl |
| 477 | 298 | 1-cyclopropyl-1-(1,1-diethyl-2-morpholinoethyl-3,3-dimethyl-6-ethoxy |
| 478 | 299 | 8-acetoxy-1-ethyl-3,3,4,4-tetramethyl-1-(2-methyl-3-piperazinopropyl) |
| 479 | 300 | 1-cyclopropyl-4,6-dimethyl-1-{3-[4-(2-hydroxyethyl)-1-piperazinyl]-1,1,2,2-tetramethylpropyl} |
| 480 | 301 | 1,3-dimethyl-1-[2,2-dipropyl-3-(1-pyrrolidinyl)propyl] |
| 481 | 302 | 4,4-dimethyl-1-ethyl-1-(1,1- |

TABLE IX-continued

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROPYRANO[3,4-b]-INDOLE-(SUFFIX LISTED BELOW)] PREFIX//SUFFIX |
|---|---|---|---|
| 507 | 13 | $CH_2=CHCH_2Br$ | 9-allyl-1-propyl//acetic acid |
| 508 | 13 | $CH_2=C(CH_3)CH_2Br$ | 9-methallyl-1-propyl//acetic acid |
| 509 | 14 | ⌬-$CH_2Cl$ | 9-benzyl-1-isopropyl//acetic acid |
| 510 | 14 | $CH_2=CHBr$ | 1-isopropyl-9-vinyl//acetic acid |
| 511 | 15 | n-$C_3H_7Cl$ | 1,9-dipropyl-3-methyl//acetic acid |
| 512 | 16 | $CH_2=CHCH_2Br$ | 9-allyl-1,4-diethyl-3-methyl//acetic acid |
| 513 | 17 | $CH_3I$ | α,1,9-trimethyl//acetic acid |
| 514 | 18 | n-$C_3H_7Cl$ | 1-cyclohexyl-α,α-dimethyl-9-propyl//acetic acid |
| 515 | 19 | $CH_2=CHCH_2Br$ | 9-allyl-1-t-butyl//acetic acid |
| 516 | 20 | $CH_2=CHCH_2I$ | 9-allyl-1-butyl//acetic acid |
| 517 | 23 | $CH_3Cl$ | 1,9-dimethyl-6-methoxy//acetic acid, m.p. 129–132° C. |
| 518 | 28 | $CH_2=CHBr$ | 6-nitro-1-propyl-9-vinyl//acetic acid |
| 519 | 32 | $CH\equiv CHCH_2Br$ | α,3-dimethyl-1-ethyl-9-propargyl-4,4,5-tripropyl//acetic acid |
| 520 | 34 | $CH_2CHCH_2Br$ | 9-allyl-1-t-butyl-α,α-diisopropyl-3,3,4,4,5-pentaethyl//acetic acid |
| 521 | 37 | $C_2H_5I$ | 7-hydroxy-1-(propyl)-β,β,9-triethyl//propionic acid |
| 522 | 38 | $CH_3I$ | 1-cyclobutyl-3,9-dimethyl-8-nitro-α-propyl//propionic acid |
| 523 | 41 | $CH_2=C(CH_3)CH_2Cl$ | 1,4,4-triethyl-9-methallyl-α,α,β-3-tetramethyl//propionic acid |
| 524 | 45 | ⌬-$CH_2CH_2Br$ | 1-methyl-6-nitro-α,α,β,β,3-pentaethyl-9-phenethyl//propionic acid |
| 525 | 47 | 1-(3-chloropropyl)piperazine | 1-cyclopropyl-α,β-diethyl-6-ethoxy-9-(3-piperidinopropyl)//propionic acid |
| 526 | 48 | $CH_3I$ | 1,9-dimethyl//butyric acid |
| 527 | 48 | ⌬-$CH_2Cl$ | 9-benzyl-1-methyl//butyric acid |
| 528 | 49 | $C_2H_5Cl$ | 1,9-diethyl-γ,3-dimethyl//butyric acid |
| 529 | 51 | $CH_2=CHBr$ | 1-cyclobutyl-3,3-dimethyl-β,γ,γ,-4-tetrapropyl-9-vinyl//butyric acid |
| 530 | 52 | $CH_2=CHBr$ | 7-chloro-α,β,β,γ,γ,4-heptaethyl-1-methyl-9-vinyl//butyric acid |
| 531 | 58 | $C_2H_5I$ | α-methyl-1,8,9-triethyl//butyric acid |
| 532 | 62 | $CH_3I$ | α,β-diethyl-1,5-dipropyl-3,9-trimethyl//butyric acid |
| 532a | 64a | $CH_3I$ | 1,5,9-trimethyl//acetic acid, m.p. 132–134° C. |
| 532b | 25 | $C_2H_5Br$ | 6-benzyloxy-9-ethyl-1-methyl//acetic acid, nmr ($CDCl_3$) δ 1.73 (s,3H), 5.12 (s,2H) |
| 532c | 64b | $CH_3I$ | 5-chloro-1,9-dimethyl//acetic acid, m.p. 105–110° C |
| 532d | 784 | $CH_3I$ | 6-benzyloxy-1,9-dimethyl//acetic acid, m.p. 167–168° C. |

TABLE X

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROTHIOPYRANO[3,4-b]-INDOLE-(SUFFIX LISTED BELOW)] PREFIX//SUFFIX |
|---|---|---|---|
| 533 | 3 | $CH_2=CHCH_2Br$ | 9-allyl-1-methyl//acetic acid |
| 534 | 3 | $CH_3I$ | 1,9-dimethyl//acetic acid |
| 535 | 3 | 4-(2-chloroethyl)-morpholine | 1-methyl-9-(2-morpholinoethyl)//acetic acid |
| 536 | 96 | n-$C_3H_7I$ | 1-methyl-9-propyl//propionic acid |
| 537 | 96 | $CH_3I$ | 1,9-dimethyl//propionic acid |
| 538 | 96 | $CH\equiv CCH_2Br$ | 1-methyl-9-propargyl//propionic acid |
| 539 | 96 | $CH_2=CHCH_2Cl$ | 9-allyl-1-methyl//propionic acid |
| 540 | 65 | $CH_3I$ | 1,9-dimethyl//carboxylic acid |
| 541 | 65 | 1-(3-chloropropyl)-piperidine | 1-methyl-9-(3-piperidinopropyl)//carboxylic acid |
| 542 | 68 | $CH_3I$ | 6-hydroxy-1-(1-propyl)-3,3,9-trimethyl//carboxylic acid |

TABLE X-continued

| EXAMPLE | NO. OF THE EXAMPLE IN WHICH STARTING MATERIAL IS PREPARED | ORGANIC HALIDE | PRODUCT: [(PREFIX LISTED BELOW)-1,3,4,9-TETRAHYDROTHIOPYRANO[3,4-b]-INDOLE-(SUFFIX LISTED BELOW)] PREFIX//SUFFIX |
|---|---|---|---|
| 543 | 70 | $CH_3CH=CHBr$ | 1-cyclopropyl-4-isopropyl-9-(1-propenyl)//carboxylic acid |
| 544 | 73 | $CH_3I$ | 1-ethyl-9-methyl//acetic acid |
| 545 | 73 | $C_2H_5Cl$ | 1,9-diethyl//acetic acid |
| 546 | 73 | 4-(2-chloroethyl)-morpholine | 1-ethyl-9-(2-morpholinoethyl)//acetic acid |
| 547 | 73 | $CH\equiv CCH_2Br$ | 1-ethyl-9-propargyl//acetic acid |
| 548 | 74 | $CH_3I$ | 9-methyl-1-propyl//acetic acid |
| 549 | 74 | $n-C_3H_7Cl$ | 1,9-dipropyl//acetic acid |
| 550 | 74 | $CH_2=CHCH_2Br$ | 9-allyl-1-propyl//acetic acid |
| 551 | 74 | $CH_2=C(CH_3)CH_2Br$ | 9-methallyl-1-propyl//acetic acid |
| 552 | 75 | $CH_3I$ | 9-methyl-1-isopropyl//acetic acid |
| 553 | 75 | $CH_2=CHBr$ | 1-isopropyl-9-vinyl//acetic acid |
| 554 | 76 | $n-C_3H_7Cl$ | 1,9-dipropyl-3-methyl//acetic acid |
| 555 | 76 | 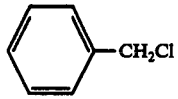 | 9-benzyl-3-methyl-1-propyl//acetic acid |
| 556 | 78 | $CH_3I$ | α,1,9-trimethyl//acetic acid |
| 557 | 79 | $n-C_3H_7Cl$ | 1-cyclohexyl-α,α-dimethyl-9-propyl//acetic acid |
| 558 | 84 | $CH_3Cl$ | 1,9-dimethyl-6-methoxy//acetic acid |
| 559 | 89 | $CH_2=CHBr$ | α,α-diethyl-1-methyl-9-vinyl-8-fluoro//acetic acid |
| 560 | 93 | $C_2H_5Cl$ | α,3-dimethyl-1,9-diethyl-1-phenyl-4,4,5-tripropyl//acetic acid |
| 561 | 95 | $CH_2=CHCH_2Br$ | 9-allyl-1-t-butyl-α,α-diisopropyl-3,3,4,4,5-pentaethyl//acetic acid |
| 562 | 98 | $C_2H_5I$ | 7-hydroxy-1-propyl-β,β,9-triethyl//propionic acid |
| 563 | 99 | $CH_3I$ | 1-cyclobutyl-3,9-dimethyl-8-nitro-α-propyl//propionic acid |
| 564 | 106 | $CH_2=CHCl$ | 1-methyl-6-nitro-α,α,β,β,3-pentaethyl-9-vinyl//propionic acid |
| 565 | 108 | $C_2H_5Cl$ | 1-cyclopropyl-6-ethoxy-α,β,9-triethyl//propionic acid |
| 566 | 109 | $CH_3I$ | 1,9-dimethyl//butyric acid |
| 567 | 109 | $CH_2=CHCH_2Cl$ | 9-allyl-1-methyl//butyric acid |
| 568 | 110 | $C_2H_5Cl$ | 1,9-diethyl-γ,3-dimethyl//butyric acid |
| 569 | 112 | $CH_2=CHBr$ | 1-cyclobutyl-3,3-dimethyl-β,γ,γ,4-tetrapropyl-9-vinyl//butyric acid |
| 570 | 119 | $C_2H_5I$ | α-methyl-1,8,9-triethyl//butyric acid |

EXAMPLE 571

By following the procedure of Example 488 but using as the starting material an equivalent amount of the ester compounds of formula I in which R⁷ is hydrogen, obtained prior to hydrolysis in Examples 1 and 3 to 125, inclusive, instead of 1-methyl-1,3,4,9-tetrahydropyrano[3,4-b]indole-1-acetic acid, and using an equivalent amount of the appropriate organic halide, then the corresponding N-alkylated ester compound of formula I in which R⁷ is lower alkyl, lower alkenyl, propargyl or phenyl(lower)alkyl is obtained.

For example, when following the procedure of Example 488, the replacement of 1-methyl-1,3,4,9-tetrahydropyrano[3,4-b]indole-1-acetic acid by an equivalent amount of its corresponding ethyl ester, described in Example 1, and then use of the same alkyl halide, methyl iodide, affords 1,9-dimethyl-1,3,4,9-tetrahydropyrano[3,4-b]-indole-1-acetic acid ethyl ester.

Similarly, the replacement of 1-methyl-1,3,4,9-tetrahydropyrano[3,4-b]indole-1-acetic acid by an equivalent amount of 1-methyl-1,3,4,9-tetrahydrothiopyrano[3,4-b]indole-1-acetic acid methyl ester, described in Example 3, affords 1,9-dimethyl-1,3,4,9-tetrahydrothiopyrano[3,4-b]indole-1-acetic acid methyl ester.

By following the procedure of Example 126 but using as starting material an equivalent amount of one of the N-alkylated acid compounds of formula I, described in Examples 488 to 570, inclusive, instead of 1-methyl-1,3,4,9-tetrahydropyrano[3,4-b]indole-1-acetic acid, and using an equivalent amount of an appropriate amine such as ammonia or a primary or secondary amine, described in Example 126, then the corresponding amide compound of formula I in which R⁷ is lower alkyl, lower alkenyl, propargyl phenyl(lower)alkyl and amino(lower)alkyl is obtained. Examples of such amides are listed as products in Tables XI, XII, XIII, and XIV together with the appropriate starting material, noted by the example in which it is prepared, and the amine used for the preparation of the amide.

TABLE XI

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 572 | 488 (title compound) | $(CH_3)_2NH$ | N,N,1,9-tetramethyl//acetamide |
| 573 | 488 (title compound) | $CH_3NH_2$ | N,1,9-trimethyl//acetamide, m.p. 136 – 138° C. |
| 574 | 488 (title compound) | $NH_3$ | 1,9-dimethyl//acetamide, m.p. 105 – 106° C. |

TABLE XI-continued

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROPYRANO[3,4-b]-INDOLE-1-(SUFFIX LISTED BELOW)] PREFIX//SUFFIX |
|---|---|---|---|
| 575 | 488 (title compound) | n-$C_6H_{13}NH_2$ | 1,9-dimethyl-N-hexyl//acetamide |
| 576 | 488 (title compound) | $(C_2H_5)_2NH$ | N,N-diethyl-1,9-dimethyl//acetamide |
| 577 | 488 (N-ethyl analog) | $(CH_3)_2NH$ | 9-ethyl-N,N,1-trimethyl//acetamide |
| 578 | 488 (N-ethyl analog) | $CH_3NH_2$ | N,1-dimethyl-9-ethyl//acetamide, m.p. 108 – 109° C. |
| 579 | 488 (N-ethyl analog) | $NH_3$ | 9-ethyl-1-methyl//acetamide, m.p. 130 – 133° C. |
| 580 | 488 (N-propyl analog) | $(CH_3)_2NH$ | 9-propyl-N,N,1-trimethyl//acetamide, m.p. 84 – 87° C. |
| 581 | 488 (N-propyl analog) | $CH_3NH_2$ | N,1-dimethyl-9-propyl//acetamide |
| 582 | 489 | $CH_3NH_2$ | 9-allyl-N,1-dimethylacetamide |
| 583 | 491 | $(CH_3)_2NH$ | 9-propargyl-N,N,1-trimethyl//acetamide |
| 584 | 493 | $(CH_3)_2NH$ | N,N,1,9-tetramethyl//propionamide |
| 585 | 493 | $CH_3NH_2$ | N,1,9-trimethyl//propionamide, m.p. 148 – 150° C. |
| 586 | 493 | $(C_2H_5)_2NH$ | 1,9-dimethyl-N,N-diethyl//propionamide |
| 587 | 495 | $NH_3$ | 1-methyl-9-(3-piperidinopropyl)//propionamide |
| 588 | 495 | $(CH_3)_2NH$ | 9-(3-piperidinopropyl-N,N,1-trimethyl//propionamide |
| 589 | 497 | $CH_3NH_2$ | 1,3-diisopropyl-N,6-dimethyl-9-propargyl//carboxamide |
| 590 | 498 | $(C_2H_5)_2NH$ | N,N-diethyl-6-hydroxy-1,3,3,9-tetramethyl//carboxamide |
| 591 | 501 | $CH_3NH_2$ | N,9-dimethyl-1-ethyl//acetamide |
| 592 | 503 | $(C_2H_5)_2NH$ | 9-allyl-N,N,1-triethyl//acetamide |
| 593 | 504 | $(CH_3)_2NH$ | N,N-dimethyl-9-[2-(dimethylamino)ethyl]-1-ethyl//acetamide |
| 594 | 505 | $CH_3NH_2$ | N,9-dimethyl-1-propyl//acetamide |
| 595 | 507 | $(C_2H_5)_2NH$ | 9-allyl-N,N-diethyl-1-propyl//acetamide |
| 596 | 514 | $CH_3NH_2$ | 1-cyclohexyl-9-propyl-N,$\alpha$,$\alpha$-trimethyl//acetamide |
| 597 | 516 | n-$C_6H_{13}NH_2$ | 9-allyl-1-butyl-N-hexyl//acetamide |
| 598 | 517 | $(CH_3)_2NH$ | 6-methoxy-N,N,1,9-tetramethyl//acetamide, m.p. 118 – 120° C. |
| 599 | 519 | $CH_3NH_2$ | 1-ethyl-9-propargyl-4,4,5-tripropyl-N,$\alpha$,3-trimethyl//acetamide |
| 600 | 524 | $(C_2H_5)_2NH$ | N,N,$\alpha$,$\alpha$,$\beta$,$\beta$,3-heptaethyl-1-methyl-6-nitro-9-phenethyl//propionamide |
| 601 | 525 | $(C_2H_5)_2NH$ | 1-cyclopropyl-6-methoxy-N,N$\alpha$,$\beta$,9-pentaethyl-9-vinyl//propionamide |
| 602 | 526 | $CH_3NH_2$ | N,1,9-trimethyl//butyramide |
| 603 | 527 | $(CH_3)_2NH$ | 9-benzyl-N,N,1-trimetyl//butyramide |
| 604 | 528 | $NH_2$ | 1,9-diethyl-$\gamma$,3-dimethyl//butyramide |
| 605 | 532 | $CH_3NH_2$ | $\alpha$,$\beta$-diethyl-1,5-dipropyl-N,3,3,9-tetramethyl//butyramide |
| 605a | 532a | $(CH_3)_2NH$ | N,N,1,5,9-pentamethyl//acetamide, nmr (CDCl$_3$) $\delta$ 1.75 (s,3H), 2.66 (s,3H), 2.96 (s,3H), 3.08 (s,3H) 3.78 (s,3H) |
| 605b | 532b | $(CH_3)_2NH$ | 6-benzyloxy-9-ethyl-N,N,1-trimethyl//acetamide, $\nu_{max}^{CHCl_3}$. 1650 cm$^{-1}$ |
| 605c | 532c | $(CH_3)_2NH$ | 5-chloro-N,N,1,9-tetramethyl//acetamide, nmr (CDCl$_3$) $\delta$ 1.72 (s,3H), 2.93 (s,3H), 3.80 (s,3H), 3.77 (s,3H) |
| 605d | 532d | $(CH_3)_2NH$ | 6-benzyloxy-N,N,1,9-tetramethyl//acetamide, nmr (CDCl$_3$) $\delta$ 1.73 (s,3H), 2.95 (s,3H), 3.05 (s,3H), 3.75 (s,3H), 5.12 (s,2H) |

TABLE XII

| EXAMPLE | NO. OF THE EXAMPLE IN WHICH STARTING MATERIAL IS PREPARED | AMINE | PRODUCT: (PREFIX LISTED BELOW)-(1,3,4,9-TETRAHYDROPYRANO[3,4-b]-INDOLE-1-YL)-(SUFFIX LISTED BELOW)] PREFIX//SUFFIX |
|---|---|---|---|
| 606 | 488 (title compound) | pyrrolidine | 1-[(1,9-dimethyl//acetyl]pyrrolidine nmr(CDCl$_3$) $\delta$ 1.77(3H), 2.82(2H), 3.78(3H), |
| 607 | 488 (title compound) | piperidine | 1-[(1,9-dimethyl//acetyl]piperidine |
| 608 | 488 (title compound) | morpholine | 1-[(1,9-dimethyl//acetyl]morpholine nmr(CDCl$_3$) $\delta$ 1.73(3H), 3.03(2H), 3.70(3H) |
| 609 | 488 (title compound) | N-methyl-piperazine | 1-methyl-4-[1,9-dimethyl//acetyl]-piperazine, $\nu_{max}^{CHCl_3}$1640 cm$^{-1}$ |
| 610 | 488 (N-ethyl analog) | pyrrolidine | 1-[(9-ethyl-1-methyl//acetyl]-pyrrolidine |
| 611 | 488 (N-ethyl analog) | piperidine | 1-[(9-ethyl-1-methyl//acetyl]-piperidine |
| 612 | 488 (N-propyl analog) | morpholine | 1-[(1-methyl-9-propyl//acetyl]- |

TABLE XII-continued

| EXAMPLE | NO. OF THE EXAMPLE IN WHICH STARTING MATERIAL IS PREPARED | AMINE | PRODUCT: (PREFIX LISTED BELOW)-(1,3,4,9-TETRAHYDROPYRANO[3,4-b]-INDOLE-1-YL)-(SUFFIX LISTED BELOW)] PREFIX//SUFFIX |
|---|---|---|---|
| 613 | 488 (title compound) | N-piperazine-ethanol | 1-(2-hydroxyethyl)-4-[1,9-dimethyl//acetyl]piperazine, $\gamma_{max}^{film}$ 1625 cm$^{-1}$. |
| 614 | 492 | pyrrolidine | 1-[(1-methyl-9-propyl//propionyl]-pyrrolidine |
| 615 | 493 | piperidine | 1-[(1,9-dimethyl//propionyl]-piperidine |
| 616 | 494 | morpholine | 1-[(1-methyl-9-phenethyl//propionyl]morpholine |
| 617 | 495 | piperazine | 1-[1-methyl-9-(3-piperidinopropyl)//propionyl]piperazine |
| 618 | 496 | pyrrolidine | 1-{1-methyl-9-[2-(1-pyrrolidinyl)-ethyl]//carbonyl}pyrrolidine |
| 619 | 501 | morpholine | 1-[(1-ethyl-9-methyl//acetyl]-morpholine |
| 620 | 502 | N-piperazine-propanol | 1-(3-hydroxypropyl)-4-[1,9-diethyl//acetyl]piperazine |
| 621 | 505 | pyrrolidine | 1-[(9-methyl-1-propyl//acetyl]-pyrrolidine |
| 622 | 507 | morpholine | 1-[(9-allyl-1-propyll//acetyl]-morpholine |
| 623 | 509 | piperidine | 1-[(9-benzyl-1-isopropyl//acetyl]-piperidine |
| 624 | 511 | piperazine | 1-[(1,9-dipropyl-3-methyl//acetyl]-piperazine |
| 625 | 513 | N-ethyl-piperazine | 1-ethyl-4-[($\alpha$,1,9-trimethyl-$\alpha$//acetyl]piperazine |
| 626 | 525 | N-propyl-piperazine | 1-propyl-4-[(1-cyclopropyl-$\alpha$,$\beta$-diethyl-6-ethoxy-9-(3-piperidinopropyl//propionyl]piperazine |
| 627 | 566 | pyrrolidine | 1-[(1,9-dimethyl//butyryl]-pyrrolidine |
| 628 | 527 | N-piperazine-methanol | 9-benzyl-1-(hydroxymethyl)-4-[(1-methyl//butyryl]piperazine |
| 629 | 530 | morpholine | 1-[(7-chloro-$\alpha$,$\beta$,$\beta$,$\gamma$,$\gamma$,4,4-heptaethyl-1-methyl-9-vinyl//butyryl]morpholine |

TABLE XIII

| EXAMPLE | NO. OF THE EXAMPLE IN WHICH STARTING MATERIAL IS PREPARED | AMINE | PRODUCT: [(PREFIX LISTED BELOW)-1,3,4,9-TETRAHYDROTHIOPYRANO[3,4-b]-INDOLE-1-(SUFFIX LISTED BELOW)] PREFIX//SUFFIX |
|---|---|---|---|
| 630 | 534 | (CH$_3$)$_2$NH | N,N,1,9-tetramethyl//acetamide |
| 631 | 534 | CH$_3$NH$_2$ | N,1,9-trimethyl//acetamide |
| 632 | 534 | NH$_3$ | 1,9-dimethyl//acetamide |
| 633 | 534 | n-C$_6$H$_{13}$NH$_2$ | 1,9-dimethyl-N-hexyl//acetamide |
| 634 | 534 | (C$_2$H$_5$)$_2$NH | N,N-diethyl-1,9-dimethyl//acetamide |
| 635 | 533 | (CH$_3$)$_2$NH | 9-allyl-N,N,1-trimethyl//acetamide |
| 636 | 537 | CH$_3$NH$_2$ | N,1,9-trimethyl//propionamide |
| 637 | 537 | (C$_2$H$_5$)$_2$NH | 1,9-dimethyl-N,N-diethyl//propionamide |
| 638 | 539 | NH$_3$ | 9-allyl-1-methyl//propionamide |
| 639 | 539 | (CH$_3$)$_2$NH | 9-allyl-N,N,1-trimethyl//propionamide |
| 640 | 541 | CH$_3$NH$_2$ | N,1-dimethyl-9-(3-piperidinopropyl)//carboxamide |
| 641 | 542 | (C$_2$H$_5$)$_2$NH | N,N-diethyl-6-hydroxy-1-propyl-3,3,9-trimethyl//carboxamide |
| 642 | 544 | CH$_3$NH$_2$ | N,9-dimethyl-1-ethyl//acetamide |
| 643 | 546 | (C$_2$H$_5$)$_2$NH | 9-(2-morpholinoethyl)-N,N,1-triethyl//acetamide |
| 644 | 547 | (CH$_3$)$_2$NH | N,N-dimethyl-1-ethyl-9-propargyl//acetamide |
| 645 | 548 | CH$_3$NH$_2$ | N,9-dimethyl-1-propyl//acetamide |
| 646 | 550 | (C$_2$H$_5$)$_2$NH | 9-allyl-N,N-diethyl-1-propyl//acetamide |
| 647 | 557 | CH$_3$NH$_2$ | 1-cyclohexyl-9-propyl-N,$\alpha$,$\alpha$-trimethyl//acetamide |
| 648 | 558 | (CH$_3$)$_2$NH | 6-methoxy-N,N,1,9-tetramethyl//acetamide |
| 649 | 564 | (C$_2$H$_5$)$_2$ | N,N,$\alpha$,$\alpha$,$\beta$,$\beta$,3-heptaethyl-1-methyl-6-nitro-9-vinyl//propionamide |
| 650 | 565 | (C$_2$H$_5$)$_2$NH | 1-cyclopropyl-6-ethoxy-N,N,$\alpha$,$\beta$,9-pentaethyl//propionamide |
| 651 | 566 | CH$_3$NH$_2$ | N,1,9-trimethyl//butyramide |
| 652 | 567 | (CH$_3$)$_2$NH | 9-allyl-N,N,1-trimethyl//butyramide |
| 653 | 568 | NH$_2$ | 1,9-diethyl-$\gamma$,3-dimethyl//butyramide |

TABLE XIV

| EXAMPLE | NO. OF THE EXAMPLE IN WHICH STARTING MATERIAL IS PREPARED | AMINE | PRODUCT: [(PREFIX LISTED BELOW)-1,3-4,9-TETRAHYDROTHIOPYRANO[3,4-b]-INDOLE-1-YL)-(SUFFIX LISTED BELOW)] PREFIX//SUFFIX |
|---|---|---|---|
| 654 | 533 | pyrrolidine | 1-[(9-allyl-1-methyl//acetyl]-pyrrolidine |
| 655 | 534 | piperidine | 1-[(1,9-dimethyl//acetyl]piperidine |
| 656 | 535 | morpholine | 1-[(1-methyl-9-(2-morpholino-ethyl)//acetyl]morpholine |
| 657 | 536 | pyrrolidine | 1-[(1-methyl-9-propyl//propionyl]-pyrrolidine |
| 658 | 537 | piperidine | 1-[(1,9-dimethyl//propionyl]-piperidine |
| 659 | 538 | morpholine | 1-[(1-methyl-9-propargyl//propionyl]morpholine |
| 660 | 539 | piperazine | 1-[9-allyl-1-methyl//propionyl]-piperazine |
| 661 | 539 | N-methyl-piperazine | 1-methyl-4-[9-allyl-1-methyl//propionyl]piperazine |
| 662 | 540 | pyrrolidine | 1-[(1,9-dimethyl//carbonyl]-pyrrolidine |
| 663 | 541 | morpholine | 1-{(1-methyl-9-(3-piperidino-propyl)//carbonyl}morpholine |
| 664 | 544 | morpholine | 1-[(1-ethyl-9-methyl//acetyl]-morpholine |
| 665 | 547 | N-piperazine-propanol | 1-(3-hydroxypropyl)-4-[(1-ethyl-9-propargyl//acetyl]piperazine |
| 666 | 548 | pyrrolidine | 1-[(9-methyl-1-propyl//acetyl]-pyrrolidine |
| 667 | 549 | morpholine | 1-[(1,9-dipropyl//acetyl]-morpholine |
| 668 | 552 | piperidine | 1-[(1-isopropyl-9-methyl//acetyl]piperidine |
| 669 | 555 | piperazine | 1-[9-benzyl-3-methyl-1-propyl//acetyl]piperazine |
| 670 | 556 | N-ethyl-piperazine | 1-ethyl-4-[α,1,9-trimethyl//acetyl]piperazine |
| 671 | 565 | N-propyl-pyrazine | 1-propyl-4-[(1-cyclopropyl-6-ethoxy-α,β,9-triethyl//propionyl]-piperazine |
| 672 | 566 | pyrrolidine | 1-[(1,9-dimethyl//butyryl]-pyrrolidine |
| 673 | 567 | N-piperazine-methanol | 1-(hydroxymethyl)-4-[(9-allyl-1-methyl//butyryl]piperazine |

EXAMPLE 674

1,9-Dimethyl-1-[2-(dimethylamino)ethyl]-1,3,4,9-tetrahydropyrano3,4-b]indole[I; $R^1 = CH_3$, $R^2$, $R^3$, $R^4$, $R^5$, and $R^6$ = H, $R^7 = CH_3$, X = O and Y = $CH_2CH_2N(CH_3)_2$]

A solution of N,N,1,9-tetramethyl-1,3,4,9-tetrahydropyrano[3,4-b]indole-1-acetamide (12.0 g), described in Example 572, in dry tetrahydrofuran (100 ml.) is added dropwise to a mechanically stirred mixture of lithium aluminium hydride (5 g) in dry tetrahydrofuran (THF) (100 ml.). The mixture is heated at reflux for twenty hours under nitrogen. Water-THF (1:1, 50 ml.) is added to destroy the excess hydride. The mixture is filtered through celite, diluted with water (300 ml.) and extracted three times with ether. The organic phase is dried over sodium sulfate, filtered and evaporated to dryness under reduced pressure to yield the title compound, nmr (CDCl₃) δ1.66 (3H), 2.70 (6H), 3,83 (3H).

The corresponding hydrochloric acid addition salt, 1,9-dimethyl-1-[2-(dimethylamino)ethyl]-1,3,4,9-tetrahydropyrano-[3,4-b]indole hydrochloride, has m.p. 229°-230° C. after crystallization from methylene dichloride-benzene.

The title compound is resolved by the use of d- and l-di-p-toluoyl-tartaric acid into the optical isomer, (—)-1,9-dimethyl-1-[2-(dimethylamino)ethyl]-1,3,4,9-tetrahydropyrano[3,4-b]indole, $[α]_D^{CHCl_3}$ = −41.5° and its corresponding (+) antipode having $[α]_D^{CHCl_3}$ 34.6°.

By following the procedure of Example 674 but using as starting material an equivalent amount of one of the N-alkylated amide compounds of formula VII, described in Examples 573 to 673 instead of N,N,1,9-tetramethyl-1,3,4,9-tetrahydro[3,4-b]indole-1-acetamide then the corresponding N-alkylated amine compound of formula I is obtained. Examples of such compounds are listed as products in Tables XV and XVI together with the appropriate starting material. In each case the starting material is noted by the example in which it is prepared.

TABLE XV

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| 675 | 573 | 1,9-dimethyl-1-[2-(methylamino)ethyl] nmr(CDCl₃) δ 1.10(1H), 1.66(S, 3H), 2.33 (S, 3H), corresponding hydrobromic acid addition salt has m.p. 223-225° C. |
| 676 | 574 | 1-(2-aminoethyl)-1,9-dimethyl,$v_{max}^{CHCl_3}$ 3369, 1570 cm⁻¹ |
| 677 | 575 | 1,9-dimethyl-1-[2-(hexylamino)ethyl] |
| 678 | 576 | 1-[2-(diethylamino)ethyl]-1,9-dimethyl, nmr (CDCl₃) δ 0.94 (t, 6H), 1.06 (S, 3H), 2.50 (m, 10H). |
| 679 | 577 | 1-[2-(dimethylamino)ethyl]-9-ethyl-1- |

TABLE XV-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| | | methyl, nmr (CDCl$_3$) δ 1.39 (3H), 1.70 (3H), 2.73 (m, 12H), corresponding hydrochloric acid addition salt has m.p. 202–205° C. |
| 680 | 578 | 9-ethyl-1-methyl-1-[2-(methylamino)ethyl] |
| 681 | 579 | 1-(2-aminoethyl)-9-ethyl-1-methyl |
| 682 | 580 | 1-[2-(dimethylamino)ethyl]-1-methyl-9-propyl, nmr (CDCl$_3$), δ 1.00 (t, 3H), 1.65 (S, 3H), corresponding maleic acid addition salt has m.p. 125–126° C. |
| 683 | 581 | 1-methyl-1-[2-(methylamino)ethyl]-9-propyl |
| 684 | 582 | 9-allyl-1-methyl-1-[2-(methylamino)ethyl] |
| 685 | 583 | 1-[2-(dimethylamino)ethyl]-1-methyl-9-propargyl |
| 686 | 584 | 1,9-dimethyl-1-[3-(dimethylamino)propyl], nmr (CDCl$_3$) δ 1.60 (3H), 2.68 (6H), corresponding maleic acid addition salt has m.p. 115–118° C. |
| 687 | 585 | 1,9-dimethyl-1-[3-(methylamino)propyl], nmr (CDCl$_3$) δ 1.6 (3H), 2.9 (3H), 3.6 (3H), corresponding hydrochloric acid addition salt has m.p. 194–196° C. |
| 688 | 586 | 1-[3-(diethylamino)propyl]-1,9-dimethyl |
| 689 | 587 | 1-(3-aminopropyl)-1-methyl-9-(3-piperidinopropyl) |
| 690 | 588 | 1-[3-(dimethylamino)propyl]-1-methyl-9-(3-piperidinopropyl) |
| 691 | 589 | 1,3-diisopropyl-1-methyl-1-(methylamino)methyl-9-propargyl |
| 692 | 590 | 1-(diethylamino)methyl-6-hydroxy-1,3,3,9-tetramethyl |
| 693 | 591 | 1-ethyl-9-methyl-1-[2-(methylamino)ethyl] |
| 694 | 592 | 9-allyl-1-[2-(diethylamino)ethyl]-1-ethyl |
| 695 | 593 | 1,9-bis-[2-(dimethylamino)ethyl]-1-ethyl |
| 696 | 594 | 9-methyl-1-[2-(methylamino)ethyl]-1-propyl |
| 697 | 595 | 9-allyl-1-[2-(diethylamino)ethyl]-1-propyl |
| 698 | 596 | 1-cyclohexyl-1-[1,1-dimethyl-2-(methylamino)ethyl]-9-propyl |
| 699 | 597 | 9-allyl-1-butyl-1-[2-(hexylamino)ethyl] |
| 700 | 598 | 1,9-dimethyl-1-[2-(dimethylamino)ethyl]-6-methoxy, nmr (CDCl$_3$) δ 2.60 (S, 3H), 3.85 (S, 3H), corresponding maleic acid addition salt has m.p. 109–111° C. |
| 701 | 599 | 1-ethyl-3-methyl-1-[1-methyl-2-(methylamino)ethyl]-9-propargyl-4,4,5-tripropyl |
| 702 | 600 | 1-[3-(diethylamino)-1,1,2,2-tetraethylpropyl]-3-ethyl-1-methyl-6-nitro-9-phenethyl |
| 703 | 601 | 1-cyclopropyl-1-[1,2-diethyl-3-(diethylamino)propyl]-6-methoxy-9-vinyl |
| 704 | 602 | 1,9-dimethyl-1-[4-(methylamino)butyl] |
| 705 | 603 | 9-benzyl-1-[4-(dimethylamino)butyl]-1-methyl |
| 706 | 604 | 1,9-diethyl-1-(4-amino-1-methylbutyl) |
| 707 | 605 | 1-[2,3-diethyl-4-(methylamino)butyl]-1,5-dipropyl-3,3,9-trimethyl |
| 708 | 606 | 1,9-dimethyl-1-[2-(1-pyrrolidinyl)ethyl], nmr (CDCl$_3$) δ 1.62 (s, 3H), 3.74 (s, 3H), m.p. of corresponding hydrochloric acid addition salt, 230–231° C. |
| 709 | 607 | 1,9-dimethyl-1-(2-piperidinoethyl), nmr (CDCl$_3$) δ 1.61 (s, 3H), 2.32 (m, 6H), 9.81 (m, 2H), m.p. of corresponding hydrochloric acid addition salt, 233–235° C. |
| 710 | 608 | 1,9-dimethyl-1-(2-morpholinoethyl) nmr (CDCl$_3$) δ 1.62 (3H), 2.77 (2H), 3.72 (3H), hydrochloric acid addition salt has m.p. 230–231° C. |
| 711 | 609 | 1,9-dimethyl-1-[2-(4-methyl-1-piperazinyl)ethyl], nmr (CDCl$_3$) δ 1.56 (s, 3H), 2.22 (s, 3H), 2.3 (m, 8H), dimaleate addition salt has m.p. 194–195° C. |
| 712 | 610 | 9-ethyl-1-methyl-1-[2-(1-pyrrolidinyl)ethyl] |
| 713 | 611 | 9-ethyl-1-methyl-1-(2-piperidinoethyl) |
| 714 | 612 | 1-methyl-1-(2-morpholinoethyl)-9-propyl |
| 715 | 613 | 1,9-dimethyl-1-{2-[4-(2-hydroxyethyl)-1-piperazinyl]ethyl}, nmr (CDCl$_3$) δ 1.60 (s, 3H), 3.70 (s, 3H), m.p. of corresponding dihydrochloride salt, m.p. 219–220° C. |
| 716 | 614 | 1-methyl-9-propyl-1-[3-(1-pyrrolidinyl)propyl] |
| 717 | 615 | 1,9-dimethyl-1-(3-piperidinopropyl) |
| 718 | 616 | 1-methyl-1-(3-morpholinopropyl)-9-phenethyl |
| 719 | 617 | 1,9-bis-(3-piperazinopropyl)-1-methyl |
| 720 | 618 | 1-methyl-1-[(1-piperazinyl)methyl]-9-[2-(1-pyrrolidinyl)ethyl] |
| 721 | 619 | 1-ethyl-9-methyl-1-(2-morpholinoethyl) |
| 722 | 620 | 1,9-diethyl-1-{2-[4-(3-hydroxypropyl)-1-piperazinyl]ethyl} |
| 723 | 621 | 9-methyl-1-propyl-1-[2-(1-pyrrolidinyl)ethyl] |
| 724 | 622 | 9-allyl-1-(2-morpholinoethyl)-1-propyl |

TABLE XV-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROPYRANO[3,4-b]INDOLE |
|---|---|---|
| 725 | 623 | 9-benzyl-1-isopropyl-1-(2-piperidinoethyl) |
| 726 | 624 | 1,9-dipropyl-3-methyl-1-(2-piperazinoethyl) |
| 727 | 625 | 1,9-dimethyl-1-[1-methyl-2-(4-methyl-1-piperazinyl)ethyl] |
| 728 | 626 | 1-cyclopropyl-1-{1,2-diethyl-3-(4-propyl-1-piperazinyl)propyl}-6-ethoxy-9-(3-piperidinopropyl) |
| 729 | 627 | 1,9-dimethyl-1-[4-(1-pyrrolidinyl)butyl] |
| 730 | 628 | 9-benzyl-1-{4-[4-(hydroxymethyl)-1-piperazinyl]butyl}-1-methyl |
| 731 | 629 | 7-chloro-4,4-diethyl-1-methyl-1-(4-morpholino-1,1,2,2,3-pentaethylbutyl)-9-vinyl |
| 731a | 605a | 1-[2-(dimethylamino)ethyl]-1,5,9-trimethyl, nmr (CDCl$_3$) δ 1.63 (s, 3H), 2.20 (s, 6H), 2.67 (s, 3H), 3.74 (s, 3H), maleate salt has m.p. 144–145° C. |
| 731b | 605b | 6-benzyloxy-1-[2-(dimethylamino)ethyl]-9-ethyl-1-methyl, nmr (CDCl$_3$) δ 1.38 (t, J=7, 3H), 1.62 (s, 3H), 2.18 (s, 6H), hydrochloride salt has m.p. 216–217° C. |
| 731c | 605c | 5-chloro-1-[2-(dimethylamino)ethyl]-1,9-dimethyl, nmr (CDCl$_3$) δ 1.63 (s, 3H), 2.18 (s, 6H), 3.72 (s, 3H), maleate salt has m.p. 148–151° C. |
| 731d | 605d | 6-benzyloxy-1,9-dimethyl-1-[2-(dimethylamino)ethyl], nmr (CDCl$_3$) δ 1.60 (s, 3H), 2.17 (s, 6H), 3.68 (s, 3H), 5.12 (s, 2H), hydrochloride salt has m.p. 238–239° C. |

TABLE XVI

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO[3,4-b]INDOLE |
|---|---|---|
| 732 | 630 | 1,9-dimethyl-1-[2-(dimethylamino)ethyl], nmr (CDCl$_3$) δ 3.72 (s, 6H), 6.40 (s, 3H); the hydrochloric acid addition salt has m.p. 254–256° C. |
| 733 | 631 | 1,9-dimethyl-1-[2-(methylamino)ethyl] |
| 734 | 632 | 1-(2-aminoethyl)-1,9-dimethyl |
| 735 | 633 | 1,9-dimethyl-1-[2-(hexylamino)ethyl] |
| 736 | 634 | 1-[2-(diethylamino)ethyl]-1,9-dimethyl |
| 737 | 635 | 9-allyl-1-[2-(dimethylamino)ethyl]-1-methyl, nmr (CDCl$_3$) δ 1.79 (s, 3H), 2.18 (s, 6H), 3.02 (m, 4H), 4.90 (m, 2H), 5.17 (m, 2H), 5.95 (m, 1H); corresponding hydrochloric acid addition salt has m.p. 228–230° C after crystallization from ethanol. |
| 738 | 636 | 1,9-dimethyl-1-[3-(methylamino)propyl] |
| 739 | 637 | 1-[3-(diethylamino)propyl]-1,9-dimethyl |
| 740 | 638 | 9-allyl-1-(3-aminopropyl)-1-methyl |
| 741 | 639 | 9-allyl-1-[3-(dimethylamino)propyl]-1-methyl |
| 742 | 640 | 1-methyl-1-[(methylamino)methyl]-9-(3-piperidinopropyl) |
| 743 | 641 | 1-[(diethylamino)methyl]-6-hydroxy-1-propyl-3,3,9-trimethyl |
| 744 | 642 | 1-ethyl-9-methyl-1-[2-(methylamino)ethyl] |
| 745 | 643 | 1-[2-(diethylamino)ethyl]-1-ethyl-9-(2-morpholinoethyl) |
| 746 | 644 | 1-[2-(dimethylamino)ethyl]-1-ethyl-9-propargyl |
| 747 | 645 | 9-methyl-1-[2-(methylamino)ethyl]-1-propyl |
| 748 | 646 | 9-allyl-1-[2-(diethylamino)ethyl]-1-propyl |
| 749 | 647 | 1-cyclohexyl-1-[1,1-dimethyl-2-(methylamino)ethyl]-9-propyl |
| 750 | 648 | 1,9-dimethyl-1-[2-(dimethylamino)ethyl]-6-methoxy |
| 751 | 649 | 1-[3-(diethylamino)-1,1,2,2-tetramethylpropyl]-3-ethyl-6-nitro-9-vinyl |
| 752 | 650 | 1-cyclopropyl-1-[1,2-diethyl-3-(diethylamino)propyl]-6-ethoxy-9-ethyl |
| 753 | 651 | 1,9-dimethyl-1-[4-(methylamino)butyl] |
| 754 | 652 | 9-allyl-1-[4-(dimethylamino)butyl]-1-methyl |
| 755 | 653 | 1-[4-amino-(1-methylbutyl)-1,9-diethyl]-3-methyl |
| 756 | 654 | 9-allyl-1-methyl-1-[2-(1-pyrrolidinyl)ethyl] |
| 757 | 655 | 1,9-dimethyl-1-(2-piperidinoethyl) |
| 758 | 656 | 1-methyl-1,9-bis(2-morpholinoethyl) |
| 759 | 657 | 1-methyl-9-propyl-1-[3-(1-pyrrolidinyl)propyl] |
| 760 | 658 | 1,9-dimethyl-1-(3-piperidinopropyl) |
| 761 | 659 | 1-methyl-1-(3-morpholinopropyl)-9- |

TABLE XVI-continued

| EXAMPLE | NO. OF THE EXAMPLE IN WHICH STARTING MATERIAL IS PREPARED | PRODUCT: (PREFIX LISTED BELOW)-1,3,4,9-TETRAHYDROTHIOPYRANO[3,4-b]INDOLE |
|---|---|---|
| 762 | 660 | propargyl 9-allyl-1-methyl-(3-piperazinopropyl) |
| 763 | 661 | 9-allyl-1-methyl-1-[3-(4-methyl-1-piperazinyl)propyl] |
| 764 | 662 | 1,9-dimethyl-1-[1-pyrrolidinyl)methyl] |
| 765 | 663 | 1-methyl-1-(morpholinomethyl)-9-(3-piperidinopropyl) |
| 766 | 664 | 1-ethyl-9-methyl-1-(2-morpholinoethyl) |
| 767 | 665 | 1-ethyl-1-{2-[4-(3-hydroxypropyl)-1-piperazinyl]ethyl-}-9-propargyl |
| 768 | 666 | 9-methyl-1-propyl-1-[2-(1-pyrrolidinyl)ethyl] |
| 769 | 667 | 1,9-dipropyl-1-(2-morpholinoethyl) |
| 770 | 668 | 1-isopropyl-9-methyl-1-(2-piperidinoethyl) |
| 771 | 669 | 9-benzyl-3-methyl-1-(2-piperazinoethyl)-1-propyl |
| 772 | 670 | 1,9-dimethyl-1-[1-methyl-2-(4-methyl-1-piperazinyl)ethyl |
| 773 | 671 | 1-cyclopropyl-6-ethoxy-9-ethyl-1-[1,2-diethyl-3-(4-propyl-1-piperazinyl)propyl] |
| 774 | 672 | 1,9-dimethyl-1-[4-(1-pyrrolidinyl)butyl] |
| 775 | 673 | 9-allyl-1-{4-[4-(hydroxymethyl)-1-piperazinyl]butyl}1-methyl |

EXAMPLE 776

1-Methyl-1,3,4,9-tetrahydropyrano[3,4-b]indole-1-carboxamide(VII, $R^1 = CH_3$, $R^2,R^3,R^4,R^5$, $R^6$ and $R^7 = H$, $X = O$, and $Z = CONH_2$)

By following the procedure of Example 1 but using boron trifluoride-etherate as the acid catalyst and an equivalent amount of pyruvamide instead of ethyl acetoacetate, 1-methyl-1,3,4,9-tetrahydropyrano[3,4-b]indole-1-carboxamide, m.p. 188° –189° C. after recrystallization from benzene-hexane, identical with the product of Example 133, is obtained.

In the same manner but using an equivalent amount of the appropriate starting material of formula II together with the appropriate α-,β-, γ- or δ-ketoamide, the products listed in Tables III and IV are obtained. For example, by using tryptophol (II; $R^2$, $R^3$, $R^4,R^5,R^6 = H$ and $X^1 = OH$) and the β-ketoamide, N,N-dimethylacetoacetamide, in the procedure of this Example, N,N,1-trimethyl-1,3,4,9-tetrahydropyrano[3,4-b]indole-1-acetamide, identical with the product of Example 126, is obtained.

EXAMPLE 777

1-Methyl-1,3,4,9-tetrahydropyrano[3,4-b]indole-1-carboxaldehyde

A mixture of the starting material, tryptophol (32.2 g, 0.2 mole), acetonyl acetate (23.2 g, 0.2 mole) and 3.2 g of p-toluenesulfonic acid in 500 ml of benzene is refluxed for 1 ½ hr. in the presence of a Dean-Stark water trap. The benzene solution is washed with 5% sodium bicarbonate, water, dried and evaporated to afford an oil. The oil is subjected to chromatography on a silica gel column using 10% ethyl acetate in benzene as eluent. The acetate 1-methyl-1,3,4,9-tetrahydroprano[3,4-b]indole-1-methanol acetate is obtained as an oil, nmr (CDCl$_3$) δ1.52 (S,3H), 2.08(S,3H), 4.35(2H).

This acetate is dissolved in 250 ml of methanol and stirred at room temperature. To this solution is added dropwise 20 ml of 10N NaOH. Hydrolysis is immediate. Most of the methanol is removed under reduced pressure, and water is added. The mixture is rendered neutral and extracted with chloroform. The chloroform extract is dried and evaporated to afford the primary alcohol, 1-methyl-1,3,4,9-tetrahydropyrano-[3,4-b]indole-1-methanol, m.p. 145 ° – 147° C., nmr(CDCl$_3$) δ1.43 (s, 3H), 2.68 (t, J = 5.5 cps, 2H), 3.65 (d, J = 6 cps, 2H), 3.86 (t, J = 5.5 cps, 2H), after crystallization from benzene-petroleum ether.

N,N-dicyclohexylcarbodiimide (17.36 g, 0.084 mole) is added to a cooled, stirred solution of the above primary alcohol (6.09 g, 0.028 mole) in 63 ml of dimethyl sulfoxidebenzene (2:1) containing trifluoroacetic acid (1.12 ml, 0.014 mole) and pyridine (2.24 ml, 0.028 mole). The reaction is stirred at room temperature under nitrogen for 5 hr. The reaction mixture is now diluted with 600 ml of ether, followed by the dropwise addition of a solution of oxalic acid (7.56 g) in 21 ml of methanol. After thirty minutes, water (600 ml) is added and the insoluble material is collected. The organic phase is washed with water (2X), 5% aqueous sodium bicarbonate (2X) and water (2X). After drying (MgSO$_4$) the organic phase is evaporated to yield an oil. The oil is purified by chromatography on silica gel. Elution with 10% ether in benzene affords the title compound as eluate, nmr (CDCl$_3$) δ1.59 (s,3H), 2.84 (t, J = 5.5 cps, 2H), 4.15 (t, J = 5.5 cps, 2H).

EXAMPLE 778

1-Methyl-1,3,4,9-tetrahydropyrano[3,4-b]indole-1-carboxaldehyde, described in Example 777, is treated with an excess of dimethylamine according to the method of K. N. Campbell, et al., J. Amer. Chem. Soc., 70, 3868 (1948), to yield the corresponding Schiff base. Reduction of the latter compound with sodium borohydride according to the procedure described by E. Schenker, Angew Chem., 73, 81 (1961), affords 1-[(dimethylamino)methyl]1-methyl-1,3,4,9-tetrahydropyrano[3,4-b] indole, identical to the product of Example 317.

By following the procedures of Examples 777 and 778 in sequence, but using as starting material in Example 777 an equivalent amount of the appropriate starting material of formula II, for example, those described in Examples 1 to 125, inclusive, and using an equivalent amount of the appropriate ketoalcohol lower alkyl ester of formula VI, described above, and in the procedure of Example 778 using an appropriate amine of formula HNR$^8$R$^9$ in which R$^8$ and R$^9$ are as defined in the first instance, then the respective compounds of formula I, for example, those described in Example 309 (other than the title company) to 487, inclusive, are obtained.

More specifically exemplified, the use of indole-3-ethanethiol, acetonyl acetate and n-hexylamine in the manner just described for the starting material of formula II, the appropriate ketoalcohol lower alkyl ester and amine, respectively, yields 1-[2-(hexylamino)ethyl]-1-methyl-1,3,4,9-tetrahydrothiopyrano-[3,4-b]indole.

EXAMPLE 779

Oxidation of 1-methyl-1,3,4,9-tetrahydropyrano[3,4-b]-indole-1-carboxaldehyde, described in Example 777, with silver oxide according to the method of Delepine and Bonnet, cited above, affords 1-methyl-1,3,4,9-tetrahydropyrano[3,4-b]indole-1-carboxylic acid, nmr (CDCl$_3$) δ1.79 (s, 3H), 2.83 (t, 2H), 4.17 (t, 2H), 9.20 (1H), identical to the product obtained in Example 4.

By following the procedures of Examples 777 and 779, in sequence, but using as starting material an equivalent amount of the appropriate starting material of formula II, for example, those described in Examples 1 to 125, inclusive, instead of tryptophol, and using an equivalent amount of the appropriate ketoalcohol lower alkyl ester of formula VI, in which R$^1$ is as defined in the first instance and Z is CH$_2$OCOR$^{20}$ or Alk$^1$CH$_2$OCOR$^{20}$ wherein R$^{20}$ and Alk$^1$ are as defined in the first instance, then the acid compound of formula I in which R$^7$ is hydrogen and Y is COOH or Alk$^1$COOH wherein Alk$^1$ is as defined above, for example, the respective products of Examples 1 to 125, inclusive, are obtained.

More specifically exemplified, according to the procedures of Examples 777 and 779, the use of tryptophol and 6-acetoxy-2-hexanne, affords 1-methyl-1,3,4,9-tetrahydrothiopyrano-[3,4-b]indole-1-butyric acid, identical to the product of Example 48. Similarly, the use of tryptophol and 5-acetoxypentan-2-one affords 1-methyl-1,3,4,9-tetrahydropyrano[3,4-b]indole-1-propionic acid, identical to the product of Example 2.

EXAMPLE 780

1-(Aminomethyl)-1-methyl-1,3,4,9-tetrahydropyrano[3,4-b]indole (I, R$^1$ = CH$_3$, R$^2$, R$^3$, R$^4$, R$^5$, R$^6$ and R$^7$ = H, X = O and Y = CH$_2$NH$_2$)

A solution of 1-methyl-1,3,4,9-tetrahydropyrano[3,4-b]-indole-1-carboxaldehyde (547 mg), described in Example 777, aqueous hydroxylamine hydrochloride (2.5 ml of 5N) and aqueous sodium acetate (2.5 ml of 5N) and methanol (5 ml) is heated at 50° – 60° C. for 5 min. and then kept at 4° C. for 16 hr. The precipitate is collected and recrystallized from ethanol water to afford 1-methyl-1,3,4,9-tetrahydropyrano[3,4-b]indole-1-carboxaldehyde oxime, m.p. 176° – 178° C.

The latter compound (230 mg) in dry THF (10 ml) is added dropwise to a stirred mixture of lithium aluminum hydride (200 mg) in 15 ml. of THF at ice bath temperature. The mixture is stirred for 1 hr., during which time it is allowed to come to room temperature. Excess lithium aluminum hydride is destroyed by the careful addition of H$_2$O/THF(1:1). Insoluble material is collected on a filter and the filtrate is concentrated. The concentrate is taken up in ether. The ether solution is dried (MgSO$_4$), filtered and concentrated to afford the title compound, identical with the compound of the same name described in Example 316.

EXAMPLE 781

1-Methyl-1-[3-(1-pyrrolidinyl)propyl]-1,3,4,9-tetrahydropyrano[3,4-b]indole[I, R$^1$ = CH$_3$, R$^2$, R$^3$, R$^4$, R$^5$, R$^6$ and R$^7$ = H, X = O and Y =

(CH$_2$)$_3$—N (CH$_2$)$_4$]

To a solution of tryptophol (15 g, 0.09 M) in 150 ml of benzene, 5-chloro-2-pentanone (12 g, 0.10 M) is added. The mixture is heated in the presence of 200 mg of p-toluene sulfonic acid and hydrated alkali-aluminum silicate (Molecular Sieves No.4). After 1 hr. of refluxing, 400 mg more of acid is added. After a total of 2 hr. the reaction is cooled, filtered and washed with 5% sodium bicarbonate, water and dried over sodium sulfate. Evaporation under reduced pressure affords an oil. This oil is purified by chromatography on silica gel. Elution with benzene and concentration of the eluent gives 1-(3-chloropropyl)-1-methyl-1,3,4,9-tetrahydropyrano-[3,4-b]indole, nmr (CDCl$_3$) δ1.33 (3H); 1.93 (4H), 2.75 (2H).

A solution of the latter compound (250 mg, 0.9 millimoles) in 10 ml of THF and 1.5 ml of pyrrolidine is heated at reflux for 16 hr. The mixture is concentrated under reduced pressure and the residue partitioned between 5% sodium carbonate and chloroform. The organic phase is washed with water, dried (Na$_2$SO$_4$), filtered and evaporated under reduced pressure to give the title compound, identical with the product of Example 365.

By following the procedure of Example 781 but using as starting material an equivalent amount of the appropriate starting material of formula II, for example, those described in Examples 1 to 125, inclusive, instead of tryptophol, and using an equivalent amount of the appropriate β-, γ-, or δ- haloketone of formula VI, described above, and the appropriate amine of formula HNR$^8$R$^9$, described above, then the respective compounds of formula I, for example those described in Examples 309 to 487, inclusive, are obtained.

EXAMPLE 782

1-[(Ethylamino)methyl]-1-methyl-1,3,4,9-tetrahydropyrano[3,4-b]indole(I, R$^1$ = CH$_3$, R$^2$, R$^3$, R$^4$, R$^5$, R$^6$ AND R$^7$ = H, X = O AND Y = CH$_2$NHCH$_3$) and A mixture of tryptophol (3.86 g; II, R$^2$, R$^3$, R$^4$, R$^5$, R$^6$ = H and X$^1$=OH) and acetamidoacetone (3.0 g), see R. H. Wileg and O. H. Borum, J. Amer. Chem. Soc., 70, 2005 (1948), in 300 ml of dry benzene is stirred and heated to reflux. Water is collected in a Dean-Stark trap. After removal of the water five drops of boron trifluoride-etherate is added and the mixture refluxed 30 min. using the water-separator again. After stirring at room temperature overnight, the reaction mixture is evaporated to dryness. The solid residue is dissolved in chloroform and washed successively with 10% aqueous sodium bicarbonate, water, and brine. The chloroform solution is dried over magnesium sulfate, filtered, and evaporated. The residue is crystallized from benzene to yield 1-(acetamidomethyl)-1-methyl-1,3,4,9-tetrahydropyrano[3,4-b]indole, m.p. 100° – 102° C. This product is dried under reduced pressure at 27° C. Spectroscopic and analytical data show that the compound is solvated with one mole of benzene which can be removed completely only be melting. $R_f$ values of the amide and tryptophol are equal.

The latter product (2.4 g) is dissolved in 80 ml of dry THF and added to a suspension of lithium aluminum hydride in 200 ml of THF.

The resultant slurry is stirred and heated to reflux for 2 hr. cooled and 2.4 g of lithium aluminum hydride is added. The mixture is then refluxed with stirring overnight. The reaction mixture is decomposed with 22.4 ml of water added dropwise over 3 hr. upon stirring and cooling. Stirring is continued for 1 hr. the precipitate is separated by filtration and the filtrate is dried ($MgSO_4$). Removed of the solvent by evaporation yield the title compound, nmr (DMSO-$d_6$) δ1.18 (t, 3H), 1.62 (s, 3H), 2.80 (t, 2H), identical to the product of Example 319.

The corresponding hydrochloric acid addition salt, 1-[(ethylamino)methyl]-1-methyl-1,3,4,9-tetrahydropyrano[3,4-b]indole hydrochloride, has m.p. 242° - 243° C., after recrystallization from isopropanol-ether.

By following the procedure of Example 782 but using as starting material an equivalent amount of the appropriate starting material of formula II, for example, those described in Examples 1 to 125, and using an equivalent amount of an appropriate ketoamide of formula

described above, then the respective secondary amine compounds of formula I are obtained.

EXAMPLE 783

1-Methyl-1-nitromethyl-1,3,4,9-tetrahydropyrano-[3,4-b]indole (VII; $R^1$ = $CH_3$, $R^2$, $R^3$, $R^4$, $R^5$, $R^6$ and $R^7$ = H, X = O AND Z = $CH_2NO_2$)

To a solution of 322 mg of tryptophol (II, $R^2$, $R^3$, $R^4$, $R^5$, $R^6$ = H and $X^1$=OH) and 248 mg of the nitroketone, nitro-2-propanone, in 100 ml of benzene is added five drops of boron trifluoride etherate and three drops of trifluoroacetic acid. The reaction mixture is stirred and heated at reflux under water-separator for 18 hr. The benzene solution is cooled, washed with 10% sodium bicarbonate solution, water, saturated brine solution, and dried over magnesium sulfate. The solvent is removed and the residue is subjected to chromatography on silica gel. Elution with chloroform gives the title compound, $\nu_{max}^{CHCl_3}$ 3450, 1550cm$^{-1}$, nmr (CDCl$_3$) δ1.68 (s, 3H), 2.84 (t, 2H), 4.10 (t, 2H).

Reduction of the latter compound with lithium aluminum hydrode according to the procedure of Example 309 affords 1-(aminomethyl)-1-methyl-1,3,4,9-tetrahydropyrano-[3,4-b]indole, identical with the product of Example 316.

By following the procedure of Example 783 but using as starting material an equivalent amount of the appropriate starting material of formula II, for example, those described in Examples 1 to 125, and using an equivalent amount of an appropriate nitroketone of formula

described above, then the respective primary amine compounds of formula I are obtained.

EXAMPLE 784

6-Hydroxy-1-methyl-1,3,4,9-tetrahydropyrano[3,4-b]indole-1-acetic acid(VIII $R^1$ = $CH_3$, $R^2$, $R^3$, $R^4$, $R^5$ and $R^7$ = H, $R^6$ = 6—OH, X = O, and Z = $CH_2COOH$)

A mixture of 6-benzyloxy-1-methyl-1,3,4,9-tetrahydropyrano[3,4-b]indole-1-acetic acid (5.3 g., 0.015 mole), prepared as described in Example 25, in 250 ml. of anhydrous ethanol, and 1.1 g. of 10% palladium on carbon is stirred at room temperature under a hydrogen atmosphere until no more hydrogen is being taken up by the reaction mixture. The catalyst is removed by filtration through diatomaceous earth (Celite) and the filtrate concentrated. The residue is recrystallized from ethanol-benzene to afford the title compound, m.p. 170° - 171° C.

The corresponding benzylamine salt is prepared by the mixing of equimolar ethereal solutions of benzylamine and the above product. The resulting solid is recrystallized from acetonitrile to afford 6-hydroxy-1-methyl-1,3,4,9-tetrahydropyrano[3,4-b]indole-1-acetic acid benzylamine salt, m.p. 191° - 193° C. The corresponding acetate is prepared by allowing a mixture of the title compound and a five molar excess of acetic anhydride in pyridine solution to stand for 24 hr. Dilution of the mixture with water extraction with ether and recrystallization of the extract residue from benzene-petroleum ether, affords 6-acetoxy-1-methyl-1,3,4,9-tetrahydropyrano[3,4-b]indole-1-acetic acid, identical with the product of Example 24.

By following the procedure of this example but replacing 6-benzyloxy-1-methyl-1,3,4,9-tetrahydropyrano[3,4-b]indole-1-acetic acid with an equivalent amount of 6-benzyloxy-1-[2-(dimethylamino)ethyl]-9-ethyl-1-methyl-1,3,4,9-tetrahydropyrano[3,4-b]indole hydrochloride, described in Example 731b, then 1-[2-(dimethylamino)ethyl]-9-ethyl-1-methyl-1,3,4,9-tetrahydropyrano[3,4-b]indole-6-ol hydrochloride, is obtained m.p. 213° - 214° C; the corresponding free base of the latter compound has nmr (CDCl$_3$) δ 1.36 (t, J = 7 cps, 3H) 1.6 (s,3H), 2.18 (s,6H). Likewise, replacement with 6-benzyloxy-1,9-dimethyl-1-[2-(dimethylamino)ethyl]-1,3,4,9-tetrahydropyrano[3,4-]indole hydrochloride described in Example 731d, gives 1,9-dimethyl-1-[2-(dimethylamino)ethyl]-1,3,4,9-tetrahydropyrano[3,4-b]indol-6-ol hydrochloride, m.p. 242°-244° C., corresponding free base has nmr (CDCl$_3$) δ 1.6 (s,3H), 2.2 (s,6H), 3.7 (s,3H).

EXAMPLE 785

1,1-Dimethyl1,3,4,9-tetrahydropyrano-[3,4-b]indole (VII; $R^1$ = $CH_3$, $R^2$, $R^3$, $R^4$, $R^5$, $R^6$, and $R^7$ = H and Z = $CH_3$)

A solution of tryptophol (8 g, 0.05M), acetone (5 g) and p-toluenesulfonic acid (100 mg) in 100 ml of benzene containing hydrated alkali-aluminium silicate (Molecular Sieves No. 4) is heated to reflux for 1 hr. More p-toluenesulfonic acid (100 mg) and the ketone, acetone (3 g), is added and the reflux continued for a further 1.5 hr.

The mixture is filtered and the filtrate is washed with 5% sodium bicarbonate and water. After drying over sodium sulfate the benzene is evaporated under reduced pressure affording a solid. Chromatography of this solid on silica gel using 30% ethyl acetate in benzene as eluant gives a white product which is recrystallized once from benzene-petroleum ether to give the title compound, m.p. 142° – 144° C., nmr (CDCl₃) δ2.76 (t, J = 5.5 cps, 2H), 4.03 (t, J = 5.5 cps, 2H).

The procedure of Example 785 is followed to prepare other compounds of formula VII in which R¹, R², R³, R⁴, R⁵, R⁶ are as defined in the first instance, R⁷ is hydrogen and Z is lower alkyl or phenyl(lower)alkyl. Examples of such compounds are listed in Tables XVII and XVIII. In each example an equivalent amount of the starting material of formula II listed therein is used instead of the starting material of formula II described in Example 785, together with the appropriate ketone.

TABLE XVII

| EXAMPLE | STARTING MATERIAL OF FORMULA II | | | | | X | KETONE OF FORMULA R¹—C(=O)—Z | | PRODUCT: (PREFIX LISTED BELOW)-1,3,4,9-TETRAHYDROPYRANO[3,4,-b]-INDOLE |
|---|---|---|---|---|---|---|---|---|---|
| | R² | R³ | R⁴ | R⁵ | R⁶ | | R¹ | Z | |
| 786 | H | H | H | H | H | O | C₂H₅ | n-C₃H₇ | 1-ethyl-1-propyl |
| 787 | H | H | H | H | H | O | CH₃ | n-C₃H₇ | 1-methyl-1-propyl, m.p. 91–93° C. |
| 788 | H | H | H | H | H | O | C₂H₅ |  —(CH₂)₂ | 1-ethyl-1-phenethyl |
| 789 | H | H | H | H | H | O | CH₃ |  —CH₂ | 1-benzyl-1-methyl, m.p. 141–145° C |
| 790 | CH₃ | H | H | H | H | O | CH₃ | CH₃ | 1,1,3-trimethyl |
| 791 | n-C₃H₇ | H | H | H | H | O | CH₃ | n-C₃H₇ | 1,3-dipropyl-1-methyl |
| 792 | CH₃ | CH₃ | H | H | H | O | ▷ | CH₃ | 1-cyclopropyl-1,3,3-trimethyl |
| 793 | C₂H₅ | H | C₂H₅ | H | H | O |  | n-C₃H₇ | 1-cyclohexyl-3,4-diethyl-1-propyl |
| 794 | H | H | CH₃ | n-C₃H₇ | H | O | CH₃ | n-C₃H₇ | 1,4-dimethyl-1,4-dipropyl |
| 795 | CH₃ | CH₃ | CH₃ | CH₃ | H | O | CH₃ |  —CH₂ | 1-benzyl-1,3,3,4,4-pentamethyl |
| 796 | H | H | H | H | 4-CH₃ | O | △ | CH₃ | 1-cyclopropyl-1,5-dimethyl |
| 797 | H | H | H | H | 5-C₂H₅ | O | ⬠ | | 1-cyclopentyl-6-ethyl |
| 798 | C₂H₅ | H | H | H | 6-OCH₃ | O | C₂H₅ | C₂H₅ | 7-methoxy-1,1,3-triethyl |
| 799 | CH₃ | CH₃ | H | H | 7-OC₂H₅ | O | CH₃ | CH₃ | 8-ethoxy-1,1,3,3-tetramethyl |
| 800 | C₂H₅ | H | H | H | 5-NO₂ | O | C₂H₅ |  —(CH₂)₃ | 1,3-diethyl-6-nitro-1-(3-phenylpropyl) |
| 801 | H | H | H | H | 7-NO₂ | O | CH₃ | CH₃ | 1,1-dimethyl-8-nitro |
| 802 | H | H | H | CH₃ | 6-CH₃COO | O | C₂H₅ | CH₃ | 7-acetoxy-1,4-dimethyl-1-ethyl |
| 803 | n-C₃H₇ | n-C₃H₇ | H | H | 5-C₂H₅COO | O | △ |  —CH₂ | 1-benzyl-1-cyclopropyl-3,3-dipropyl-6-propionyloxy |
| 804 | H | H | H | H | 4-Cl | O | △ | CH₃ | 5-chloro-1-cyclopropyl-methyl |
| 805 | CH₃ | H | H | H | 6-Cl | O |  |  —CH₂ | 1-benzyl-7-chloro-1-cyclohexyl-3-methyl |
| 806 | C₂H₅ | H | H | H | 5-Br | O | C₂H₅ | C₂H₅ | 6-bromo-1,1,3-triethyl |
| 807 | H | H | n-C₃H₇ | n-C₃H₇ | 7-Br | O | n-C₃H₇ | CH₃ | 8-bromo-1-methyl-1,4,4-tripropyl |
| 808 | CH₃ | CH₃ | CH₃ | CH₃ | 4-F | O | CH₃ | CH₃ | 5-fluoro-1,1,3,3,4,4-hexamethyl |
| 809 | H | H | H | H | 6-F | O | △ | n-C₃H₇ | 1-cyclopropyl-7-fluoro-1-propyl |
| 810 | CH₃ | H | CH₃ | H | 7-I | O | CH₃ |  —(CH₂) | 8-iodo-1-phenethyl-1,3,4-trimethyl |
| 811 | H | H | H | H | 5-I | O | CH₃ | CH₃ | 1,1-dimethyl-6-iodo |

TABLE XVIII

| EX. | STARTING MATERIAL OF FORMULA II | | | | | X | KETONE OF FORMULA R¹—C(=O)—Z | | PRODUCT: (PREFIX LISTED BELOW)-1,3,4,9-TETRAHYDROTHIOPYRANO-[3,4-b]INDOLE |
|---|---|---|---|---|---|---|---|---|---|
| | R² | R³ | R⁴ | R⁵ | R⁶ | | R¹ | Z | |
| 812 | H | H | H | H | H | S | CH₃ | CH₃ | 1,1-dimethyl |
| 813 | H | H | H | H | H | S | CH₃ | n-C₃H₇ | 1-methyl-1-propyl |
| 814 | H | H | H | H | H | S | C₂H₅ |  —(CH₂)₂ | 1-ethyl-1-phenethyl |
| 815 | H | H | H | H | H | S | CH₃ |  —CH₂ | 1-benzyl-1-methyl |
| 816 | CH₃ | H | H | H | H | S | CH₃ | CH₃ | 1,1,3-trimethyl |
| 817 | n-C₃H₇ | H | H | H | H | S | CH₃ | n-C₃H₇ | 1,3-dipropyl-1-methyl |
| 818 | CH₃ | H | H | H | H | S | △ | CH₃ | 1-cyclopropyl-1,3,3,-trimethyl |

TABLE XVIII-continued

| EX. | STARTING MATERIAL OF FORMULA II R² | R³ | R⁴ | R⁵ | R⁶ | X | KETONE OF FORMULA R¹—C(=O)—Z R¹ | Z | PRODUCT: (PREFIX LISTED BELOW)-1,3,4,9-TETRAHYDROTHIOPYRANO-[3,4-b]INDOLE |
|---|---|---|---|---|---|---|---|---|---|
| 819 | C₂H₅ | H | C₂H₅ | H | H | S |  | n-C₃H₇ | 1-cyclohexyl-3,4-diethyl-1-propyl |
| 820 | H | H | CH₃ | n-C₃H₇ | H | S | CH₃ | n-C₃H₇ | 1,4-dimethyl-1,4-dipropyl |
| 821 | CH₃ | CH₃ | CH₃ | CH₃ | H | S | CH₃ |  | 1-benzylmethyl-1,3,3,4,4-pentamethyl |
| 822 | H | H | H | H | 4-CH₃ | S |  | CH₃ | 1-cyclopropyl-1,5-dimethyl |
| 823 | H | H | H | H | 5-C₂H₅ | S |  | | 1-cyclopentyl-6-ethyl |
| 824 | C₂H₅ | H | H | H | 6-OCH₃ | S | C₂H₅ | C₂H₅ | 7-methoxy-1,1,3-triethyl |
| 825 | CH₃ | CH₃ | H | H | 7-OC₂H₅ | S | CH₃ | CH₃ | 8-ethoxy-1,1,3,3-tetramethyl |
| 826 | C₂H₅ | H | H | H | 5-NO₂ | S | C₂H₅ |  | 1,3-diethyl-6-nitro-1-(3-phenylpropyl) |
| 827 | H | H | H | H | 7-NO₂ | S | CH₃ | CH₃ | 1,1-dimethyl-8-nitro |
| 828 | H | H | H | CH₃ | 6-CH₃COO | S | C₂H₅ | CH₃ | 7-acetoxy-1,4-dimethyl-1-ethyl |
| 829 | n-C₃H₇ | n-C₃H₇ | H | H | 5-C₂H₅COO | S |  |  | 1-benzyl-1-cyclopropyl-3,3-dipropyl-6-propionyloxy |
| 830 | H | H | H | H | 4-Cl | S |  | CH₃ | 5-chloro-1-cyclopropyl-1-methyl |
| 831 | CH₃ | H | H | H | 6-Cl | S |  |  | 1-benzyl-7-chloro-1-cyclohexyl-3-methyl |
| 832 | C₂H₅ | H | H | H | 5-Br | S | C₂H₅ | C₂H₅ | 6-bromo-1,1,3-triethyl |
| 833 | H | H | n-C₃H₇ | n-C₃H₇ | 7-Br | S | n-C₃H₇ | CH₃ | 8-bromo-1-methyl-1,4,4-tripropyl |
| 834 | CH₃ | CH₃ | CH₃ | CH₃ | 4-F | S | CH₃ | CH₃ | 5-fluoro-1,1,3,3,4,4-hexamethyl |
| 835 | H | H | H | H | 6-F | S |  | n-C₃H₇ | 1-cyclopropyl-7-fluoro-1-propyl |
| 836 | CH₃ | H | CH₃ | H | 7-I | S | CH₃ |  | 8-iodo-1-phenethyl-1,3,4-trimethyl |
| 837 | H | H | H | H | 5-I | S | CH₃ | CH₃ | 1,1-dimethyl-6-iodo |

EXAMPLE 838

1,1-Dimethyl-9-[2-(dimethylamino)ethyl]-1,3,4,9-tetrahydropyrano[3,4-b]indole [I; R¹ and Y = CH₃, R², R³, R⁴, R⁵ and R⁶ = H, AND R⁷ = CH₂CH₂N(CH₃)₂]

To 4.2 g. of a 50% dispersion of sodium hydride in 20 ml. of dimethylformamide is added a solution of 7 g. of 1,1-dimethyl-1,3,4,9-tetrahydropyrano[3,4-b]indole, described in Example 785, in 20 ml. of dimethylformamide. The addition is made dropwise at room temperature while stirring vigorously. The mixture is heated for 1 hr. at 40° C. Then an excess of the organic halide, dimethylaminoethyl chloride (free base obtained from 15 g. of the hydrochloride) is added and stirring continued at 40° C. overnight.

The reaction mixture is poured into ice-water, acidified with 6NHCl and washed with ether. The aqueous phase is rendered alkaline with 10% NaOH and extracted with benzene. The organic phase is washed with water, dried over sodium sulfate, and evaporated under reduced pressure to yield the title compound, nmr (CDCl₃) δ1.63 (6H), 2.36 (6H), 2.79 (m, 4H), 4.10 (m, 4H), 7.18 (m, 4H).

The corresponding hydrochloric acid addition salt, 1,1-dimethyl-9-[(2-dimethylamino)ethyl]-1,3,4,9-tetrahydropyrano-[3,4-b]indole hydrochloride, has m.p. 198° – 200° C., after crystallization from methanol-ether.

The procedure of Example 838 is followed to prepare other compounds of formula I in which R¹, R², R³, R⁴, R⁵, R⁶ and X are as defined in the first instance, R⁷ is aminoalkyl as defined above and Y is lower alkyl or phenyl(lower)alkyl. Examples of such compounds are listed in Tables XIX and XX. In each example an equivalent amount of the appropriate starting material of formula VII in which R¹, R², R³, R⁴, R⁵, R⁶ are as defined in the first instance, R⁷ is hydrogen and Z is lower alkyl or phenyl(lower)alkyl, described in Examples 785 to 837, is used in place of 1,1-dimethyl-1,3,4,9-tetrahydropyrano[3,4-b]indole if required. In each case the starting material of formula VII is noted by the example in which it is prepared.

TABLE XIX

| EXAMPLE | NO. OF THE EXAMPLE IN WHICH STARTING MATERIAL IS PREPARED | ORGANIC HALIDE | PRODUCT: (PREFIX LISTED BELOW)-1,3,4,9-TETRAHYDROPYRANO-[3,4-b]INDOLE |
|---|---|---|---|
| 839 | 785 | (CH₃)₂N(CH₂)₃Cl | 1,1-dimethyl-9-[3-(dimethylamino)propyl], nmr (CDCl₃) δ 1.62 (6H), 2.00 (m, 2H), 2.25 (6H), corresponding hydrochloric acid addition salt has m.p. 201–203° C. |

TABLE XIX-continued

| EXAMPLE | NO. OF THE EXAMPLE IN WHICH STARTING MATERIAL IS PREPARED | ORGANIC HALIDE | PRODUCT: (PREFIX LISTED BELOW)-1,3,4,9-TETRAHYDROPYRANO-[3,4-b]INDOLE |
|---|---|---|---|
| 840 | 785 | $CH_3NH(CH_2)_2Cl$ | 1,1-dimethyl-9-[2-(methylamino)-ethyl] |
| 841 | 785 | $i\text{-}C_3H_7NH(C_2)_2Cl$ | 1,1-dimethyl-9-[2-(isopropyl-amino)ethyl] |
| 842 | 786 | $NH_2CH_2C(CH_3)_2CH_2Br$ | 9-(3-amino-2,2-dimethylethyl)-1-ethyl-1-propyl |
| 843 | 787 | $(CH_3)_2N(CH_2)_2Cl$ | 9-[2-(dimethylamino)ethyl]-1-methyl-1-propyl, $\nu_{max}^{CHCl_3}$ 2960, 1470, 1085 cm$^{-1}$, maleate salt has m.p. 144–147° C. |
| 844 | 788 | $C_2H_5NH(CH_2)_3Cl$ | 1-ethyl-9-[3-(ethylamino)propyl]-1-phenethyl |
| 845 | 789 | $(CH_3)_2N(CH_2)_2Cl$ | 1-benzyl-9-[2-(dimethylamino)-ethyl]-1-methyl, nmr (CDCl$_3$) δ 1.55 (s, 3H), 2.92 (6H), 3.95 (2H), corresponding hydrochloric acid addition salt has m.p. 218–220° C. |
| 846 | 789 | $CH_3NH(CH_2)_2Cl$ | 1-benzyl-1-methyl-9-[2-(methyl-amino)ethyl] |
| 847 | 789 | $NH_2(CH_2)_3Cl$ | 9-(4-aminobutyl)-1-benzyl-1-methyl |
| 848 | 790 | $(CH_3)_2NCH_2[CH(CH_3)]_2Cl$ | 9-[1,2-dimethyl-3-(dimethyl-amino)propyl]-1,1,3-trimethyl |
| 849 | 791 | $(C_2H_5)_2NCH(C_2H_5)CH_2Cl$ | 9-[2-(diethylamino)-2-ethylethyl]-1,3-dipropyl-1-methyl |
| 850 | 792 | $CH_3NH(CH_2)_3Cl$ | 1-cyclopropyl-9-[3-(methyl-amino)propyl]-1,3,3-trimethyl |
| 851 | 793 | $(CH_3)_2N(CH_2)_2Cl$ | 1-cyclohexyl-3,4-diethyl-9-[2-(dimethylamino)ethyl]-1-propyl |
| 852 | 794 | $(n\text{-}C_3H_7)_2N(CH_2)_3Cl$ | 1,4-dimethyl-1,4-dipropyl-9-[3-(dipropylamino)propyl] |
| 853 | 795 | $(CH_3)_2NCH(n\text{-}C_3H_7)CH_2Cl$ | 1-benzyl-9-[2-(dimethylamino)-2-propylethyl]-1,3,3,4,4-pentamethyl |
| 854 | 796 | $(CH_3)_2N[CH(n\text{-}C_3H_7)]_3CH_2Cl$ | 1-cyclopropyl-1,5-dimethyl-9-[4-(dimethylamino)-2,3,4-tripropylbutyl] |
| 855 | 797 | $(C_2H_5)_2N(CH_2)_2Cl$ | 1-cyclopentyl-9-[2-(diethyl-amino)ethyl]-6-ethyl |
| 856 | 798 | $CH_3NH(CH_2)_3Cl$ | 7-methoxy-9-[3-(methylamino)-propyl]-1,1,3-triethyl |
| 857 | 799 | $n\text{-}C_3H_7NH(CH_2)_2Cl$ | 8-ethoxy-9-[2-(propylamino)-ethyl]-1,1,3,3-tetramethyl |
| 858 | 800 | $i\text{-}C_3H_7NH(CH_2)_2Cl$ | 1,3-diethyl-9-[2-(isopropyl-amino)ethyl]-6-nitro-1-(3-phenylpropyl) |
| 859 | 801 | $(CH_3)_2N(CH_2)_2Cl$ | 1,1-dimethyl-9-[2-(dimethyl-amino)ethyl]-8-nitro |
| 860 | 802 | $C_2H_5NH(CH_2)_3Cl$ | 7-acetoxy-1,4-dimethyl-1-ethyl-9-[3-(ethylamino)propyl] |
| 861 | 803 | $(CH_3)_2N(CH_2)_2Cl$ | 1-benzyl-1-cyclopropyl-9-[2-(dimethylamino)ethyl-3,3-dipropyl-6-propionyloxy] |
| 862 | 804 | $n\text{-}C_3H_7NH(CH_2)_3Cl$ | 5-chloro-1-cyclopropyl-1-methyl-9-[3-(propylamino)-propyl] |
| 863 | 805 | 1-(3-chloropropyl)-pyrrolidine | 1-benzyl-7-chloro-1-cyclohexyl-3-methyl-9-[3-(pyrrolidinyl)-propyl] |
| 864 | 806 | 1-(2-chloroethyl)-piperidine | 6-bromo-9-(2-piperidinoethyl)-1,1,3-triethyl |
| 865 | 807 | 4-(2-chloroethyl)-morpoline | 8-bromo-1-methyl-9-(2-morpholino-ethyl)-1,4,4-tripropyl |
| 866 | 808 | 1-(3-chloropropyl)-piperazine | 5-fluoro-1,1,3,3,4,4-hexamethyl-9-(piperazinopropyl) |
| 867 | 809 | 1-(3-chloroethyl)-4-methylpiperazine | 1-cyclopropyl-7-fluoro-9-[2-(4-methyl-1-piperazinyl)-ethyl]-1-propyl |
| 868 | 810 | 1-(2-chloroethyl)-4-(hydroxyethyl)piperazine | 9-{2-[4-(hydroxyethyl)-1-piperazinyl]ethyl}-8-iodo-1-phenethyl-1,3,4-trimethyl |
| 869 | 811 | 1-(2-chloroethyl)-pyrrolidine | 1,1-dimethyl-6-iodo-9-[2-(1-pyrrolidinyl)ethyl] |
| 870 | 785 | 1-(3-chloropropyl)-piperidine | 1,1-dimethyl-9-(3-piperidino-propyl) |
| 871 | 785 | 4-(4-chlorobutyl)-morpholine | 1,1-dimethyl-9-(4-morpholino-butyl) |
| 872 | 789 | 1-(4-chlorobutyl)-4-methylpiperazine | 9-[4-(4-methyl-1-piperazinyl)-butyl] |
| 873 | 789 | 1-(2-chloroethyl)-4-(3-hydroxypropyl)-piperazine | 1-benzyl-9-{2-[4-(hydroxypropyl)-1-piperazinyl]ethyl}-1-methyl |

TABLE XX

| EXAMPLE | NO. OF EXAMPLE IN WHICH STARTING MATERIAL IS PREPARED | ORGANIC HALIDE | PRODUCT: (PREFIX LISTED BELOW)-1,3,4,9-TETRAHYDROTHIOPYRANO[3,4-b]INDOLE |
|---|---|---|---|
| 874 | 812 | (CH₃)₂N(CH₂)₃Cl | 1,1-dimethyl-9-[3-(dimethylamino)propyl] |
| 875 | 812 | CH₃NH(CH₂)₂Cl | 1,1-dimethyl-9-[2-(methylamino)ethyl] |
| 876 | 812 | i-C₃H₇NH(CH₂)₂Cl | 1,1-dimethyl-9-[2-(isopropylamino)ethyl] |
| 877 | 812 | NH₂CH₂C(CH₃)₂CH₂Br | 9-(3-amino-2,2-dimethylethyl)-1,1-dimethyl |
| 878 | 813 | (CH₃)₂N(CH₂)₂Cl | 9-[2-(dimethylamino)ethyl]-1-methyl-1-propyl |
| 879 | 814 | C₂H₅NH(CH₂)₃Cl | 1-ethyl-9-[3-(ethylamino)propyl]1-phenethyl |
| 880 | 815 | (CH₃)₂N(CH₂)₂Cl | 1-benzyl-9-[2-(dimethylamino)ethyl]-1-methyl |
| 881 | 815 | CH₃NH(CH₂)₂Cl | 1-benzyl-1-methyl-9-[2-(methylamino)ethyl] |
| 882 | 815 | NH₂(CH₂)₃Cl | 9-(4-aminobutyl)-1-benzyl-1-methyl |
| 883 | 816 | (CH₃)₂NCH₂[CH(CH₃)]₂Cl | 9-[1,2-dimethyl-3-(dimethylamino)propyl]-1,1,3-trimethyl |
| 884 | 817 | (C₂H₅)₂NCH(C₂H₅)CH₂Cl | 9-[2-(diethylamino)-2-ethylethyl]1,3-dipropyl-1-methyl |
| 885 | 818 | CH₃NH(CH₂)₃Cl | 1-cyclopropyl-9-[3-(methylamino)propyl]-1,3,3-trimethyl |
| 886 | 819 | (CH₃)₂N(CH₂)₂Cl | 1-cyclohexyl-3,4-diethyl-9-[2-(dimethylamino)ethyl]-1-propyl |
| 887 | 820 | (n-C₃H₇)₂N(CH₂)₃Cl | 1,4-dimethyl-1,4-dipropyl-9-[3-(dipropylamino)propyl] |
| 888 | 821 | (CH₃)₂NCH(n-C₃H₇)CH₂Cl | 1-benzyl-9-[2-(dimethylamino)-2-propylethyl]-1,3,3,4,4-pentamethyl |
| 889 | 822 | (CH₃)₂N[CH(n-C₃H₇)]₃CH₂Cl | 1-cyclopropyl-1,5-dimethyl-9-[4-(dimethylamino)-2,3,4-tripropylbutyl] |
| 890 | 823 | (C₂H₅)₂N(CH₂)₂Cl | 1-cyclopentyl-9-[2-(diethylamino)ethyl]-6-ethyl |
| 891 | 824 | CH₃NH(CH₂)₃Cl | 7-methoxy-9-[3-(methylamino)propyl]-1,1,3-triethyl |
| 892 | 825 | n-C₃H₇NH(CH₂)₂Cl | 8-ethoxy-9-[2-(propylamino)ethyl]-1,1,3,3-tetramethyl |
| 893 | 826 | i-C₃H₇NH(CH₂)₂Cl | 1,3-diethyl-9-[2-(isopropylamino)ethyl]-6-nitro-1-(3-phenylpropyl) |
| 894 | 827 | (CH₃)₂N(CH₂)₂Cl | 1,1-dimethyl-9-[2-(dimethylamino)ethyl]-8-nitro |
| 895 | 828 | C₂H₅NH(CH₂)₃Cl | 7-acetoxy-1,4-dimethyl-1-ethyl-9-[3-(ethylamino)propyl] |
| 896 | 829 | (CH₃)₂N(CH₂)₂Cl | 1-benzyl-1-cyclopropyl-9-[2-(dimethylamino)ethyl]-3,3-dipropyl-6-propionyloxy |
| 897 | 830 | n-C₃H₇NH(CH₂)₃Cl | 5-chloro-1-cyclopropyl-1-methyl-9-[3-(propylamino)propyl] |
| 898 | 831 | 1-(3-chloropropyl)-pyrrolidine | 1-benzyl-7-chloro-1-cyclohexyl-3-methyl-9-[3-(1-pyrrolidinyl)propyl] |
| 899 | 832 | 1-(2-chloroethyl)-piperidine | 6-bromo-9-(2-piperidinoethyl)-1,1,3-triethyl |
| 900 | 833 | 4-(2-chloroethyl)-morpholine | 8-bromo-1-methyl-9-(2-morpholinoethyl)-1,4,4-tripropyl |
| 901 | 834 | 1-(3-chloropropyl)-piperazine | 5-fluoro-1,1,3,3,4,4-hexamethyl-9-(piperazinopropyl) |
| 902 | 835 | 1-(3-chloroethyl)-4-methylpiperazine | 1-cyclopropyl-7-fluoro-9-[2-(4-methyl-1-piperazinyl)-ethyl]-1-propyl |
| 903 | 836 | 1-(2-chloroethyl)-4-(hydroxyethyl)-piperazine | 9-{2-[4-(hydroxyethyl)-1-piperazinyl]ethyl}-8-iodo-1-phenethyl-1,3,4-trimethyl |
| 904 | 837 | 1-(2-chloroethyl)-pyrrolidine | 1,1-dimethyl-6-iodo-9-[2-(1-pyrrolidinyl)ethyl] |
| 905 | 812 | 1-(3-chloropropyl)-piperidine | 1,1-dimethyl-9-(3-piperidinopropyl) |
| 906 | 812 | 4-(4-chlorobutyl)-morpholine | 1,1-dimethyl-9-(4-morpholinobutyl) |
| 907 | 815 | 1-(4-chlorobutyl)-4-methylpiperazine | 1-benzyl-1-methyl-9-[4-(4-methyl-1-piperazinyl)butyl] |
| 908 | 815 | 1-(2-chloroethyl)-4-(3-hydroxypropyl)-piperazine | 1-benzyl-9-{2-[4-(hydroxypropyl-1-piperazinyl]ethyl}-1-methyl |

EXAMPLE 909

1,1-Dimethyl-9-[2-(dimethylamino)ethyl]-1,3,4,9-tetrahydropyrano[3,4-b]indole-6-OL [I. $R^1$ and $Y = CH_3$, $R^2$, $R^3$, $R^4$ and $R^5 = H$, $R^6 = OH$ and $R^7 = CH_2CH_2N(CH_3)_2$]

5-Benzyloxy-3-tryptophol (II; $R^2$, $R^3$, $R^4$ and $R^5 = H$, $R^6 = $ 5-benzyloxy and $X^1 = OH$), m.p. 93° – 95° C., is prepared by lithium aluminum hydride reduction of ethyl 5-benzyloxy-3-indoleglyoxalate (British Pat. No. 778,823) according to the procedure of Example 309. Subsequent treatment of 5-benzyloxy-3-tryptophol with the ketone, acetone, according to the procedure of Example 785 affords 6-benzyloxy-1,1-dimethyl-1,3,4,9-tetrahydropyrano[3,4-b]indcole (VII; $R^1$ M $CH_3$), nmr ($CDCl_3$) δ1.53 (6H), 2.73 (t, 2H), 4.03 (t, 2H), 5.10 (2H), 6.67 – 7.83 (9H). The latter compound is then N-alkylated with the organic halide, dimethylaminoethyl chloride, according to the procedure of Example 838 to afford 6-benzyloxy-1,1-dimethyl-9-[2-(dimethylamino)ethyl]-1,3,4,9-tetrahydropyrano[3,4-b]indole, which on treatment with hydrochloric acid gives the corresponding hydrochloric acid addition salt thereof, m.p. 209° C.

The latter compound, 6-benzyloxy-1,1-dimethyl-9-[2-(dimethylamino)ethyl]-1,3,4,9-tetrahydropyrano[3,4-b]indole hydrochloride (11.5 g., 0.028M) in 600 ml. of absolute ethanol and 600 mg of 10% palladium on carbon is stirred at room temperature under a hydrogen atmosphere for 22 hr. until no more hydrogen is taken up by the reaction. The catalyst is collected on celite and the filtrate concentrated to afford the corresponding hydrochloric acid addition salt of the title compound, m.p. 225° – 228° C., after recrystallization from ethanol-ether.

The title compound [free base, nmr ($CDCl_3$) δ1.61 (6H), 2.57 (t, J = 5 cps, 2H), 3.86 (t, J = 5 cps, 2H)] is obtained by decomposing the hydrochloric acid addition salt, for example, by washing a chloroform solution of the salt with 10% sodium hydroxide solution and evaporating the solvent.

By replacing 5-benzyloxy-3-tryptophol with an equivalent amount of 7-benzyloxy-3-tryptophol in the procedure of this example, 1,1-dimethyl-9-[2-(dimethylamino)ethyl]-1,3,4,9-tetrahydropyrano[3,4-b]indole-8-ol is obtained.

EXAMPLE 910

1-(2-Aminoethyl)-1-methyl-1,3,4,9-tetrahydropyrano[3,4-b]indole (I; $R^1 = CH_3$, $R^2$, $R^3$, $R^4$, $R^5$, $R^6$ and $R^7 = H$, $X = O$ and $Y = CH_2NH_2$)

1-Methyl-1,3,4,9-tetrahydropyrano[3,4-b]indole-1-acetamide (20.0 g., 0.817 mole), described in Example 126, is dissolved in dry methylene chloride (400 ml) and freshly prepared triethyloxonium fluoroborate (17.00 g., 0.894 mole) is added in one portion to the solution. The reaction mixture is stirred at room temperature for 2 hr.. The methylene chloride solution is washed with cold 30% aqueous potassium carbonate followed by brine and the dried organic layer is concentrated under reduced pressure. The residue is dissolved in ether (150 ml.). The solution is filtered and crystallization proceeds at room temperature to afford ethyl-1-methyl-1,3,4,9-tetrahydropyrano[3,4-b]indole-1-acetimidate, m.p. 139.5 ° – 141° C.

The latter compound (4.79 g., 0.0176 mole) dissolved in dry THF (100 ml.) is added dropwise to a stirred and ice-cooled suspension of lithium aluminum hydride (1.75 g., 0.046 mole) in THF (50 ml.). The reaction mixture is stirred overnight at room temperature and then dilute sodium hydroxide is added dropwise to decompose excess hydride. The precepitate is collected by filtration and the filtrate is concentrated under reduced pressure thus affording a residue which is extracted with methylene chloride. The organic layers are washed with brine, dried ($MgSO_4$) and concentration of the solvent and crystallization from ether affords the title compound, m.p. 80° – 84° C., $\nu_{max}^{CHCl_3}$ 3455, 3280 cm$^{-1}$, identical with the compound of the same name described in Example 309.

EXAMPLE 911

1-[2-(Dimethylamino)ethyl]-9-ethyl-1-methyl-1,3,4,9-tetrahydrothiopyrano[3,4-b]indole [I; $R^1 = CH_3$, $R^2$, $R^3$, $R^4$, $R^5$, and $R^6 = H$, $R^7 = C_2H_5$, $X = S$ and $Y = CH_2CH_2N(CH_3)_2$]

The compound of formula I in which $R^7 = H$ and $Y = $ amino(lower)alkyl, 1-[2-(dimethylamino)ethyl]-1-methyl-1,3,4,9-tetrahydrothiopyrano[3,4-b]indole (822 mg), described in Example 398, is dissolved in 15 ml of DMF and 15 ml of benzene. To remove all possible traces of water, a portion of this benzene is distilled. After cooling to 0° C, 140 mg of sodium hydride (54% suspension in mineral oil) is added, and the mixture stirred for 15 min. Alkylation is accomplished by addition of 350 mg of ethyl bromide and stirring the reaction mixture at 0° C for 20 min. The resulting suspension is poured onto cracked ice, extracted with chloroform, the organic layer washed repeatedly with water and evaporated. Chromatography of the residue on silica gel (20 g) using chloroform-methanol (0–10%) affords the title compound, which after crystallization from ether hexane has m.p. 86° – 88° C., $\nu_{max}^{CHCl_3}$ 2820, 2765, 1600, 1568, 1537 cm$^{-1}$, nmr ($CDCl_3$) δ2.20 (s, 6H), 2.30 (m, 4H).

The corresponding hydrochloric acid addition salt of the title compound, 1-[2-(dimethylamino)ethyl]-9-ethyl-1-methyl-1,3,4,9-tetrahydrothiopyrano[3,4-b]indole hydrochloride, has m.p. 220° – 222° C.

By following the procedure of Example 911 and using an appropriate compound of formula I in which $R^7$ is hydrogen and Y is an amino(lower)alkyl, for instance those described in Examples 309 to 487, together with the appropriate organic halide, then other compounds of formula I in which $R^7$ is lower alkyl, lower alkenyl, propargyl, phenyl(lower)alkyl or amino(lower)alkyl are obtained.

For example, the use of the same compound of formula I as described in Example 911 with an equivalent amount of methyl bromide, instead of ethyl bromide, in the procedure of Example 911 gives 1,9-dimethyl-1-[2-(dimethylamino)ethyl]-1,3,4,9-tetrahydrothiopyrano[3,4-b]indole, nmr ($CHCl_3$) δ3.72 (s, 6H), 6.40 (s, 3H), identical to the product of Example 732. The corresponding hydrochloric acid addition salt of this latter compound, 1,9-dimethyl-1-[2-(dimethylamino)ethyl]-1,3,4,9-tetrahydrothiopyrano[3,4-b]indole hydrochloride has m.p. 244° – 246° C.

Likewise, the use of the same compound of formula I as described in Example 911 with an equivalent amount of propyl bromide, instead of ethyl bromide, gives 1-[2-(dimethylamino)ethyl]-1-methyl-9-propyl-1,3,4,9-tetrahydrothiopyrano[3,4-b]-indole, nmr($CHCl_3$) δ1.03(t, 3H), 1.83(S,3H), 2.22(S,6H), 4.14(m, 2H), 7.22(m, 4H);

corresponding hydrochloric acid addition salt has m.p. 243°–245° C.

EXAMPLE 912

1-[(2-Dimethylamino)ethyl]-1-methyl-1,3,4,9-tetrahydropyrano[3,4-b]indole [1; $R^1 = CH_3$, $R^2$, $R^3$, $R^4$, $R^5$, $R^6$ and $R^7 = H$, $X = O$ and $Y = CH_2CH_2(N(CH_3)_2]$ To a solution of p-toluenesulfonic acid (2.28 g) in toluene (40 ml), the starting material of formula 11, tryptophol (1.61 g), and the aminoketone, 4-(dimethylamino)-2-butanone (1.27 g) are added. The mixture is evaporated under reduced pressure and the residue stirred under nitrogen at 130° C (bath temperature) for 45 min.. The mixture is cooled, water (20 ml) added and the mixture extracted with toluene. The toluene extract is washed with 5% sulfuric acid (5 ml) and with water (5 ml). The aqueous layer containing a dark heavy oil is combined with the aqueous washes. Conc. $NH_4OH$ (10 ml) is added and the mixture extracted with toluene (10 ml and 2 × 5 ml). The combined toluene solution is washed with water (2 × 5 ml), dried ($Na_2SO_4$), treated with charcoal and evaporated under reduced pressure. The residue is recrystallized from ether to afford the pure title compound, identical to the product of the same name described in Example 309.

EXAMPLE 913

1,9-Dimethyl-1-[2-(dimethylamino)ethyl]-1,3,4,9-tetrahydropyrano[3,4-b]indole [1; $R^1$ and $R^7 = CH_3$, $R^2$, $R^3$, $R^4$, $R^5$, and $R^6 = H$, $X = O$ and $Y = CH_2CH_2N(CH_3)_2$]

To a mixture of the starting material of formula 11, N-methyltryptophol (0.50 g), and the aminoketone, 4-dimethylamino-2-butanone (0.363 g), p-toluenesulfonic acid (0.650 g) is added in portions and the mixture stirred under nitrogen at 130° C for 1 ½ hr. After cooling water is added (10 ml) and the mixture is extracted with toluene (2 × 5 ml). The combined toluene solution is backwashed with water and discarded. The aqueous phase, containing a heavy brown oil, is make alkaline with conc. ammonium hydroxide (10 ml) and extracted with benzene (3 × 10 ml). The combined benzene extract is washed with water (2 × 10 ml), dried ($Na_2SO_4$), treated with charcoal and evaporated under reduced pressure to yield the title compound, identical to the product of the same name described in Example 674.

EXAMPLE 914

1,9-Dimethyl-1-[2-(dimethylamino)ethyl]-1,3,4,9-tetrahydrothiopyrano[3,4-b]indole [1; $R^1$ and $R^7 = CH_3$, $R^2$, $R^3$, $R^4$, $R^5$ and $R^6 = H$, $X = S$ and $Y = CH_2CH_2N(CH_3)_2$]

A mixture of the starting material of formula II, 1-methylindole-3-ethanethiol (0.75 g), 4-dimethylamino-2-butanone hydrochloride (0.72 g), toluene (ca. 1 ml) and p-toluenesulfonic acid (1.00 g), is stirred under nitrogen at 125° C for ½ hr. After cooling, water (20 ml) and conc. hydrochloric acid (0.5 ml) are added and the mixture is then extracted with toluene (3 × 10 ml). The combined toluene solution is backwashed with water. The aqueous phase containing a brown oil is rendered alkaline with conc. $NH_4OH$ and extracted with toluene (3 × 15 ml). The combined toluene solution is washed with water, dried ($Na_2SO_4$), treated with charcoal and evaporated under reduced pressure to yield the title compound, identical to the product of the same name described in Example 732.

EXAMPLE 915

1-[2-(Dimethylamine)ethyl] 9-ethyl : methyl-1,3,4,9-tetrahydrothiopyrano[3,4-b]indole [1; $R^1 = CH_3$, $R^2$, $R^3$, $R^4$, $R^5$, and $R^6 = H$, $R^7 = C_2H_5$, $X = S$ and $Y = CH_2CH_2N(CH_3)_2$]

To a stirred solution of p-toluenesulfonic acid monohydrate (57.0 g) in toluene (400 ml) at 80° C. under nitrogen, the aminoketone, 4-(dimethylamino)-2-butanone (13.8 g), is added. Thereafter, the starting material of formula II, sodium 1-ethylindole-3-ethyl thiosulfate (30.7 g), prepared from 1-ethylindole-3-ethanol according to the procedure of Suvorov and Buyanov, cited above, is added portionwise over a pericd of 5 minutes. The mixture is maintained at 80° C. for 1 ¼ hr. with stirring then cooled and diluted with 20% sodium hydroxide (66 ml) followed by water (100 ml) and extracted with toluene. The toluene extract is washed with 20% sulfuric acid (5 × 30 ml) and with water (5 × 30 ml). The combined aqueous phases plus solid precipitating therefrom are rendered alkaline with 20% sodium hydroxide and then extracted with toluene (4 × 50 ml). The combined toluene solution is washed with water, dried ($Na_2SO_4$), and evaporated. The residue is recrystallized from ether-hexane to give the title compound, identical to the product of Example 911. The corresponding hydrochloric acid addition salt of the title compound has m.p, 225°–227° C. after recrystallization from isopropanol.

In the same manner but using an equivalent amount of potassium 1-ethylindole-3-ethyl thiosulfate the title compound is also obtained.

By following the procedure of Examples 912, 913, 914 or 915 and using an appropriate starting material of formula ii together with the appropriate aminoketone, then other compounds of formula I, for example, those described in Examples 309 –487 and 675 – 775, are obtained.

EXAMPLE 916

4'-Chloro-2-{methyl[2-(1,3,4,9-tetrahydro-1,9-dimethylpyrano[3,4-b]indole-1-yl)ethyl]amino}-acetophenone[I, $R^1$ and $R^7 = CH_3$, $R^2$, $R^3$, $R^4$, $R^5$ and $R^6 = H$, $X=O$ and $Y=CH_2CH_2N(CH_3)(p\text{-chlorophenacyl})$]

1,9-Dimethyl-1-[2-(methylamino)ethyl]-1,3,4,9-tetrahydropyrano-[3,4-b]indole hydrobromide (2.0 g), described in Example 675, and 2-bromo-4'-chloroacetophenone (1.37 g) are dissolved in benzene (10 ml). A solution of sodium hydrogen carbonate (1.2 g) and sodium sulfite (0.06 g) in water (5 ml) are added. The reaction mixture is stirred at room temperature for 3 hr. The aqueous phase is separated and discarded. The organic phase is washed with 0.5 ml or 2N HCl, with water and dried ($Na_2SO_4$). After filtration, 2.6 ml of a 2.3 M solution of hydrogen chloride in ether is added. The resulting gummy material is crystallized from methanol and ether to afford the hydrochloric acid addition salt of the title compound, mp. 199° – 205° C (dec.).

Conversion of the latter salt to its free base is achieved washing a chloroform solution of the salt with 5% NaOH solution. Subsequent concentration of the chloroform gives the title compound as the free base, nmr $(CDCl_3)\delta$ 1.6(s,3H), 2.3 (s,3H), 3.65 (s,2H), 3.7 (s,3H).

By replacing 1,9-dimethyl-1-[2-(methylamino)ethyl]-1,3,4,9-tetrahydropyrano[3,4-b]indole hydrobromide with 9-ethyl-1-methyl-1-[2-(methylamino(ethyl]-1,3,4,9-tetrahydrothiopyrano[3,4-b]indole hydrochloride, described in Example 917, 4′-chloro-2-{[2-(9-ethyl-1-methyl-1,3,4,9-tetrahydropyrano[3,4-b]indole-1-yl)ethyl]methylamino}acetophenone, nmr (CDCl$_3$) δ 1.40 (t, J = 7.5 Hz, 3H), 1.80 (s, 3H), 2.35 (s, 3H) is obtained; the hydrochloride addition salt of the latter compound has m.p. 175°–177° C.

EXAMPLE 917

9-Ethyl-1-methyl-1-[2-(methylamiono)ethyl]-1,3,4,9-tetrahydrothiopyrano [3,4-b]indole (I; R$^1$=CH$_3$, R$^2$, R$^3$, R$^4$, R$^5$ and R$^6$=H, R$^7$= C$_2$H$_5$, X=S and Y=CH$_2$CH$_2$NHCH$_3$)

A mixture of sodium 2-[(1-ethyl-indol-3-yl)ethyl]-thisoulfate (12 g) 4-(formylamino)-2-butanone (6 g), described by H. Bredereck, et al., Chem. Ber., 2423 (1960), toluene (30 ml) and boron trifluoride-etherate (20 ml) is heated at 80° for 4 hr. After cooling, 150 ml of chloroform and 100 ml of saturated sodium bicarbonate are added. The resultant mixture is stirred until the precipitated solids dissolve. The organic phase is separated, washed with water, and concentrated. The residue is purified by chromatography on silica gel, using chloroform and chloroform-methanol (100 : 3) as elements. Combination of major fractions gives the N-formyl derivative, 9-ethyl-1-methyl-1-[2-(formylamino)ethyl]-1,3,4,9-tetrahydrothipyrano [3,4-b]indole, $\nu_{max}^{CHCl_3}$ 3410, 1680 cm$^{-1}$, nmr (CDCl$_3$) δ1.38 (t, J=7, 3H), 1.82 (s, 3H), 2.20 (m, 2H), 3.00 (m,6H), 4.31 (q, J=7, 2H), 6.00 (broad, 1H), 7.22 (m, 4H), 7.98 (d, J=2, 1H).

The latter compound (3 g) in 40 ml of dry ether is added to a stirred suspension of lithium aluminium hydride (0.7 g) in 40 ml of the same solvent. The reaction mixture is heated at reflux for 3 hr., decomposed with 4 ml of 30% aqueous solution of sodium-potassium tartrate, and filtered. The filter cake is washed with tetrahydrofuran and the filtrate dried (MgSO$_4$). Usual work-up afforded the title compound as an oil, nmr (DMSO-d$_6$) 1.32 (t, J=7, 3H), 1.78 (s, 3H), 7.2 (m,3H).

The hydrochloric acid addition salt of the title compound has mp 259°–261° C after recrystallization from isopropanol-methanol (9 : 1).

This example is a specific embodiment of preparation and conversion of intermediates of formula VII (2=Alk NR$^8$COR$^{21}$), see also Example 782.

EXAMPLE 918

9-Ethyl-1-methyl-1-(2-aminoethyl)-1,3,4,9-tetrahydrothiopyrano[3,4-b]indole (I; R$^1$=CH$_3$, R$^2$, R$^3$, R$^4$, R$^5$ and R$^6$=H, R$^7$=C$_2$H$_5$, X=S and Y=CH$_2$CH$_2$NH$_2$)

The N-formyl compound described in Example 917 is hydrolyzed by boiling the compound (1.0 g) in 10 ml of conc. HCl in 10 ml of methanol for 24 hr. The reaction mixture is concentrated under reduced pressure. The aqueous residue is washed with ether, and then rendered basic with 10% NaOH. Extraction with ether affords 9-ethyl-1-methyl-1-(2-aminoethyl)-1,3,4,9-tetrahydrothiopyrano [3,4-b]indole. nmr (CDCl$_3$) δ 1.40 (t,J=7, 3H), 1.82 (s,3H), 1.90 (s, exchangeable, 2H), 4.31 (q,J=7, 2H). Basic hydrolysis (10% NaOH in methanol) of the above N-formyl compound gave product identical with the preceeding product.

The hydrochloric acid addition salt of the latter compound has mp. 257°–258° C after recrystallization from isopropanol ether.

In the same manner as described in the preceding Examples 1 to 784 inclusive and 910 to 918 but replacing the starting material of formula II with the corresponding starting material of formula IIa, the pyrano-[4,3-b]indole and thiopyrano [4,3-b]indole derivatives of formula Ia, corresponding to the pyrano [3,4-b]indole and thiopyrano [3,4-b]indole derivatives of formula I, described in these preceding examples, are obtained. This latter aspect of this invention is illustrated further in the following Examples 919 to 921.

EXAMPLE 919

1,5-Dimethyl-1,3,4,5-tetrahydropyrano[4,3-b]indole-1-acetic acid (VIIa; R$^1$ and R$^7$=C$_3$, R$^2$, R$^3$, R$^4$, R$^5$ and R$^6$ = H, X=O and Z=CH$_2$COOH)

The compound of formula VI, ethyl acetoacetate (6.5 g), is added to a stirred suspension of aluminum chloride (2.0 g) in anhydrous toluene (60 ml) at 60°. The mixture is stirred until solution is complete (c.a. 10 min.). 2-(1-Methylindole)ethanol (IIa, R$^2$, R$^3$, R$^4$, R$^5$ and R$^6$=CH$_3$ and X$^1$=OH, 8.7 g) in toluene (60 ml) is added dropwise during 40 min. The mixture is stirred for 1 hr at 60° and then cooled to 10° C and treated with water (60 ml). The toluene layer is washed with water, dried and evaporated to dryness, the residue is crystallized from ethanol to give the pure ethyl ester of the title compound, m.p. 136° –138° C.

The ester is hydrolyzed with aqueous ethanol-sodium hydroxide to give the crude acid which crystallized from toluene to give the pure title product, m.p. 181°–112° C.

1Methylindole-2-ethanyl[nmr(CDCl$_3$)δ2.63, 2.88, 3.55, and 6.12] used in this example is prepared by the method of Julia et al., cited above.

By following the procedure of this example and using the appropriate starting material of formula IIa, together with the appropriate compound of formula VI, other intermediates of formula VIIa are obtained.

EXAMPLE 920

1-[2-(Dimethylamino)ethyl]-1,5-dimethyl-1,3,4,5-tetrahydropyrano[4,3-b]indole [Ia, R$^1$ and R$^7$ = CH$_3$, R$^2$, R$^3$, R$^4$, R$^5$ and R$^6$ = H, X = O and Y = CH$_2$CH$_2$N(CH$_3$)$_2$]

A solution of 1,5-dimethyl-1,3,4,5-tetrahydropyrano[4,3-b]indole-1-acetic acid ethyl ester (17.0 g), described in Example 916, in tetrahydrofuran (200 ml) is added dropwise to a suspension of lithium aluminium hydride (5.0 g) in tetrahydrofuran (150 ml). The mixture is heated at reflux for 2.5 hr. and then cooled and treated with a mixture of water-tetrahydrofuran (30 ml – 150 ml). The mixture is filtered through celite and the filtrate is evaporated. The residue is purified by chromatography on silica gel. Elution with chloroform gives 1,5-dimethyl-1,3,4,5-tetrahydropyrano[4,3-b]indole-1-ethanol.

A solution of the latter compound (6.5 g) in 75 ml of pyridine, cooled to 0° C, is treated with 10.0 g of p-toluenesulfonyl chloride. The resulting solution is kept at 3° C overnight; thereafter, it is poured into ice water. The mixture is extracted with ether. The extract is washed with water, dried and evaporated at low temperature to give the corresponding tosylate. This material is dissolved in dimethylformamide (DMF, 80 ml) and dimethylamine (16 ml) is added. The mixture is heated under reflux for 1.5 hr. The DMF is evaporated and the residue is dissolved in chloroform. The chloroform solution is washed with water and then evaporated to give the title compound, nmr (CDCl₃) δ 1.62, 2.15 and 4.12, is obtained; the corresponding oxalic acid addition salt thereof having m.p. 139° -140° C., after crystallization from isopropanol.

By following the same procedure but replacing dimethylamine with an equivalent amount of diethylamine, 1-[2-(diethylaminoethyl]-1,5-dimethyl-1,3,4,5-tetrahydropyrano[4,3-b]indole, nmr (CDCl₃) δ 1.63, 3.65 and 4.05, is obtained; the oxalic acid addition salt thereof having m.p. 122° -124° C., after crystallization from isopropanol.

By following the procedure of this example and using the appropriate ester of formula VIIa (Z = COOR¹⁹ and Alk¹—COOR¹⁹), together with the appropriate amine of formula HNR⁸R⁹ in which R⁸ and R⁹ are as defined in the first instance then other compounds of formula Ia are obtained.

EXAMPLE 921

5-Ethyl-1-methyl-1-[2-(dimethylamino)ethyl]-1,3,4,5-tetrahydrothiopyrano[4,3-b]indole (Ia, R¹ = CH₃, R², R³, R⁴, R⁵ and R⁶ = H, R⁷ = C₂H₅, X = S and Y = CH₂CH₂N(CH₃)₂]

A mixture of sodium 2-[(1-ethyl-indol-2-yl)ethyl]thiosulfate (6 g), derived from 1-ethylindole-2-ethanol having nmr (CDCl₃) δ 1.26, 1.99, 2.91, 3.86, 4.08, 6.27, 4-dimethylamino-2-butanone (3 g), toluene (10 ml) and boron trifluoride etherate (10 ml) is heated at 80° for 4 hr. After cooling the reaction mixture is processed in the same manner as described for the work-up of the N-formyl derivative in Example 919 to afford the title compound, nmr (CDCl₃) δ 1.3 (t, J = 7, 3H), 1.7 (s, 3H), 2.15 (s, 6H), 4.3 (q, J = 7, 2H).

EXAMPLE 922

(+)- or
(−)-1-[2-(Dimethylamino)ethyl]-9-ethyl-1-methyl-1,3,4,9-tetrahydrothiopyrano[3,4-b]indole Racemic 1-[2-(Dimethylamino)ethyl]-9-ethyl-1-methyl-1,3,4,9-tetrahydrothiopyrano[3,4-b]indole, described in Example 915, is separated into its enatiomers by using either (+)- or (−)-mandelic acid. When the racemate is treated with (−)-mandelic acid a mixture of diastereomeric salts is obtained. Upon trituration of the mixture with water, the water-insoluble (−)-mandelate, $[\alpha]_D^{25}$ = 137° (MeOH), m.p. 110° - 113° C, separates from the water-soluble (+)-mandelate, $[\alpha]_D^{25}$ = + 36.2° C (MeOH). Subsequent decomposition with dilute sodium hydroxide yields the corresponding (+) or (−) free bases, i.e. the title compounds. The (+) base has $[\alpha]_D^{25}$ = + 43.1° (MeOH) and the (−) base has $[\alpha]_D^{25}$ = − 44.5° (MeOH). Corresponding hydrochloric acid addition salts have m.p. 224° -226° C, $[\alpha]_D^{25}$ = + 10.1° (MeOH) and m.p. 222° -224° C, $[\alpha]_D^{25}$ = − 11.1° (MeOH), respectively.

We claim:
1. A method of preventing and treating ulcers in warm blooded animals which comprises:
   administering to said mammal an effective dose of from about 0.1 milligram to about 50 milligrams per kilogram of mammal weight per day of a compound selected from those of the formulae I and Ia

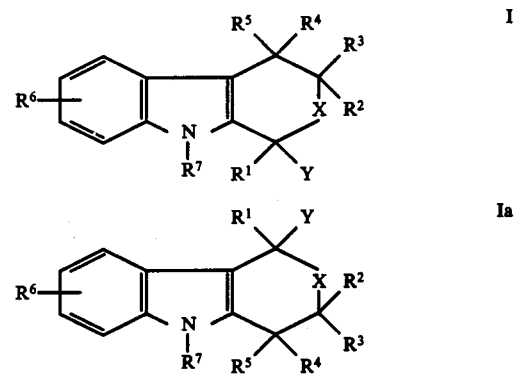

in which R¹ is lower alkyl or lower cycloalkyl; R², R³, R⁴ and R⁵ are the same or different selected from the group consisting of hydrogen and lower alkyl; R⁶ is hydrogen, lower alkyl, hydroxy, lower alkoxy, lower alkanoyloxy, nitro or halo; R⁷ is hydrogen, lower alkyl, lower alkenyl, propargyl, phenyl(lower)alkyl or an amino(lower)alkyl radical of formula —Alk-NR⁸R⁹ wherein Alk is an alkylene selected from the group consisting of CR¹⁰R¹¹CR¹²R¹³, CR¹⁰R¹¹CR¹²R¹³CR¹⁴R¹⁵, and CR¹⁰R¹¹CR¹²R¹³CR¹⁴R¹⁵CR¹⁶R¹⁷ wherein R¹⁰, R¹¹, R¹², R¹³, R¹⁴, R¹⁵, R¹⁶ and R¹⁷ are hydrogen or lower alkyl and R⁸ and R⁹ are either the same or different selected from the group consisting of hydrogen and lower alkyl, or R⁸ is lower alkyl and R⁹ is p-chlorophenacyl, or R⁸ and R⁹ together with the nitrogen atom to which they are joined form a heterocyclic amine radical selected from the group consisting of 1-pyrrolidinyl, piperidino, morpholino, 1 piperazinyl, 4-(lower alloyl) 1-piperazinyl and 4-[hydroxy(lower)alkyl]-1-piperazinyl; X is oxy: and Y is lower alkyl, phenyl(lower)alkyl or an amino(lower)alkyl radical of formula —Alk-NR⁸R⁹ wherein Alk is an alkylene selected from the group consisting of CR¹⁰R¹¹,CR¹⁰R¹¹CR¹²R¹³, CR¹⁰R¹¹CR¹²R¹³CR¹⁴R¹⁵and CR¹⁰R¹¹CR¹²R¹³CR¹⁴R¹⁵CR¹⁶R¹⁷ wherein R¹⁰, R¹¹, R¹², R¹³, R¹⁴, R¹⁵, R¹⁶ and R¹⁷ are hydrogen or lower alkyl and R⁸ and R⁹ are as defined herein; with the proviso that at least one of R⁷ and Y is —Alk-NR⁸R⁹ and that in the compounds of formula Ia, Y is —Alk NR⁸R⁹ as defined herein; and the corresponding acid addition salt with a pharmaceutically acceptable acid.

2. The method of claim 1 in which the compound of formula I is 1-[2-(dimethylamino)ethyl]-1-methyl-1,3,4,9-tetrahydropyrano[3,4-b]indole, or a pharmaceutically acceptable acid addition salt thereof.

3. The method of claim 1 in which the compound of formula I is 1-[2-(dimethylamino)ethyl]-9-ethyl-1-methyl-1,3,4,9-tetrahydropyrano[3,4-b]indole, or a pharmaceutically acceptable acid addition salt thereof.

4. The method of claim 1 in which the compound of formula I is 1,9-dimethyl-1-[2-(dimethylamino)ethyl]-1,3,4,9-tetrahydropyrano[3,4-b]indole, or a pharmaceutically acceptable acid addition salt thereof.

* * * * *

UNITED STATES PATENT AND TRADEMARK OFFICE
CERTIFICATE OF CORRECTION

PATENT NO. : 4,066,780
DATED : January 3, 1978
INVENTOR(S) : Christopher A. Demerson et al It is certified that error appears in the above-identified patent and that said Letters Patent are hereby corrected as shown below:

Column 2, line 17, "form" should read -- from --;

Column 3, line 21, "contamplates" should read -- contemplates --;

Column 21, Table I, Example 6, second column and eighth column, "n-$C_3H_7$" should read -- i-$C_3H_7$ --;

Column 21, Table I, Example 16, fifth column, "$CH_3$" should read -- H --;

Column 25, Table II, Example 77, fifth column, "$CH_3$" should read -- H --;

Column 32, Table III, Example 164, third column, "$NH_2$" should read -- $NH_3$ --;

Column 32, Table III, Example 168, third column, "$NH_2$" should read -- $NH_3$ --;

Column 32, Table III, Example 174, third column, "$NH_2$" should read -- $NH_3$ --;

Column 32, Table III, Example 178, third column, "$NH_2$" should read -- $NH_3$" --;

Column 35, Table V, Example 255, third column, "$NH_2$" should read -- $NH_3$ --;

Column 35, Table V, Example 258, third column, "$NH_2$" should read -- $NH_3$ --;

UNITED STATES PATENT AND TRADEMARK OFFICE
CERTIFICATE OF CORRECTION

PATENT NO. : 4,066,780

DATED : January 3, 1978

INVENTOR(S) : Christopher A. Demerson et al

It is certified that error appears in the above-identified patent and that said Letters Patent are hereby corrected as shown below:

Column 35, Table V, Example 268, third column, "$NH_2$" should read -- $NH_3$ --;

Column 35, Table VI, Example 286, second line of fourth column "carbonyl)piperzine" should read -- carbonyl)piperazine --;

Column 40, Table VII, Example 319, fifth line of third column, "245" should read -- 242 --;

Column 41, Table VII, Example 352, second line of third column, after "triethyl" add -- -3-methyl --;

Column 41, Table VII, Example 354, second line of third column, "trimethyl" should read -- triethyl --;

Column 45, Table VIII, Example 440, second line of third column, after "triethyl" add -- -3-methyl --;

Column 45, Table VIII, Example 442, second line of third column, "trimethyl" should read -- triethyl --;

In the heading for Table IX and X appearing in column 48, column 50 twice and column 52, the third line of the fourth heading, "INDOLE-(SUFFIX" should read -- INDOLE-1-(SUFFIX --;

Column 49, Table IX, Example 525, second line of third column, "propyl)piperazine" should read -- propyl)piperidine --;

Column 50, Table IX, Example 525, fourth column, first line, "6" should read -- 7 --;

UNITED STATES PATENT AND TRADEMARK OFFICE
CERTIFICATE OF CORRECTION

PATENT NO. : 4,066,780

DATED : January 3, 1978

INVENTOR(S) : Christopher A. Demerson et al

It is certified that error appears in the above-identified patent and that said Letters Patent are hereby corrected as shown below:

Column 52, Table X, Example 565, fourth column, first line, "6" should read -- 7 --;

Column 52, line 53, after "propargyl" insert a -- comma --;

Column 54, Table XI, Example 601, fourth column, the product should read -- 1-cyclopropyl-7-ethoxy-N,N,$\alpha$, $\beta$-tetraethyl-9-(3-piperidinopropyl) // propionamide --;

Column 53, Table XI, Example 604, third column, "$NH_2$" should read -- $NH_3$ --;

Column 56, Table XII, Example 626, second line of fourth column, "6" should read -- 7 --;

Column 56, Table XIII, Example 649, third column, "$(C_2H_5)_2$" should read -- $(C_2H_5)_2NH$ --;

Column 56, Table XIII, Example 650, first line of fourth column, "6" should read -- 7 --;

Column 56, Table XIII, Example 653, third column, "$NH_2$" should read -- $NH_3$ --;

Column 57, Table XIV, Example 671, second line of third column, "pyrazine" should read -- piperazine --;

Column 57, Table XIV, Example 671, first line of fourth column, "6" should read -- 7 --;

UNITED STATES PATENT AND TRADEMARK OFFICE
CERTIFICATE OF CORRECTION

PATENT NO. : 4,066,780

DATED : January 3, 1978

INVENTOR(S) : Christopher A. Demerson et al

It is certified that error appears in the above-identified patent and that said Letters Patent are hereby corrected as shown below:

Column 60, Table XV, Example 703, second line of third column, "6-methoxy-9-vinyl" should read - - 7-ethoxy-9-(3-piperidinopropyl) - -;

Column 62, Table XVI, Example 752, second line of third column, "6" should read - - 7 - -;

Column 64, Table XVI, Example 773, first line of third column, "6" should read - - 7 - - ;

Column 66, line 50, "$CH_2NHCH_3$" should read - - $CH_2NHC_2H_5$ - -;

Column 68, line 27, after "water" insert a - - comma - - ;

Column 70, Table XVII, Example 810, ninth column, under Z, the symbol should read

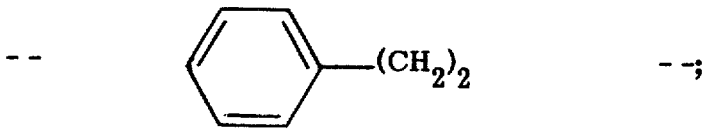

Column 72, Table XVIII, Example 821, first line of last column, "benzylmethyl" should read - - benzyl - - ;

Column 72, Table XVIII, Example 836, ninth column, under Z, the symbol should read

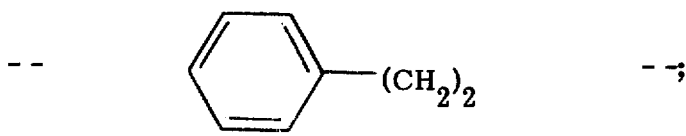

UNITED STATES PATENT AND TRADEMARK OFFICE
CERTIFICATE OF CORRECTION

PATENT NO. : 4,066,780

DATED : January 3, 1978

INVENTOR(S) : Christopher A. Demerson et al

It is certified that error appears in the above-identified patent and that said Letters Patent are hereby corrected as shown below:

Column 77, line 15, delete "M" and insert -- = --;

Column 77, line 51, "$CH_2NH_2$" should read -- $CH_2CH_2N_2$ --;

Column 78, line 4, "precepitate" should read -- precipitate --;

Column 79, line 7, "$CH_2CH_2(N(CH_3)_2$" should read -- $CH_2CH_2N(CH_3)_2$ --;

Column 80, line 3, ")9-ethyl:" should read -- )-9-ethyl-1- --;

Column 81, line 25, "elements" should read -- eluants --;

Column 81, line 47, "2" should read -- Z --;

Column 82, line 32, "112" should read -- 182 --;

Column 82, line 33, "1Methylindole-2-ethanyl" should read -- 1-Methyl-indole-2-ethanol --;

Column 82, line 48, "916" should read -- 919 --;

Claim 1, column 84, line 37, "alloyl) 1" should read -- alkyl)-1 --;

Signed and Sealed this

Sixth Day of November 1979

[SEAL]

Attest:

RUTH C. MASON
*Attesting Officer*

LUTRELLE F. PARKER
*Acting Commissioner of Patents and Trademarks*